US012758096B1

(12) United States Patent
Nudd et al.

(10) Patent No.: US 12,758,096 B1
(45) **Date of Patent: *Oct. 13, 2026**

(54) AUTOMATIC IN-HOME SENIOR CARE SYSTEM AUGMENTED WITH INTERNET OF THINGS TECHNOLOGIES

(71) Applicant: ClearCare, Inc., San Francisco, CA (US)

(72) Inventors: Geoffrey Howard Nudd, Atherton, CA (US); David Cristman, San Francisco, CA (US); Jonathan J. Hull, San Carlos, CA (US); Bala Krishna Nakshatrala, Los Angeles, CA (US)

(73) Assignee: ClearCare, Inc., San Francisco, CA (US)

( * ) Notice: Subject to any disclaimer, the term of this patent is extended or adjusted under 35 U.S.C. 154(b) by 105 days.

This patent is subject to a terminal disclaimer.

(21) Appl. No.: 18/774,197

(22) Filed: Jul. 16, 2024

Related U.S. Application Data

(63) Continuation of application No. 18/304,669, filed on Apr. 21, 2023, now Pat. No. 12,076,108, which is a
(Continued)

(51) Int. Cl.
*G10L 15/00* (2013.01)
*A61B 5/00* (2006.01)
(Continued)

(52) U.S. Cl.
CPC ............ *A61B 5/0022* (2013.01); *A61B 5/165* (2013.01); *G06F 9/542* (2013.01); *G06F 17/18* (2013.01);
(Continued)

(58) Field of Classification Search
CPC ....... G10L 15/16; G10L 19/005; G10L 19/00; G10L 25/27; G10L 25/30; G10L 17/18;
(Continued)

(56) References Cited

U.S. PATENT DOCUMENTS 6,598,020 B1 7/2003 Kleindienst
8,374,865 B1 2/2013 Biadsy
(Continued)

FOREIGN PATENT DOCUMENTS

AU 2009202262 A1 12/2009
WO 2005059681 A2 6/2006
(Continued)

OTHER PUBLICATIONS

ASA TRY AN, "4 Disorders That May Thrive on Loneliness," Jul. 23, 2015, retrieved online from https://www.psychologytoday.com/us/blog/the-art-closeness/201507/4-disorders-may-thrive-loneliness, on Apr. 8, 2019, 5 pgs.
(Continued)

*Primary Examiner* — Vu B Hang
(74) *Attorney, Agent, or Firm* — Patent Law Works, LLP

(57) ABSTRACT

The in-home care of seniors is augmented using Internet of Things (IOT) technologies. In-home sensors monitor a senior and their caregiver. Physical conditions and psychological conditions may be monitored. In some implementations, a machine learning system has a classifier trained to detect a specified condition, such as depression. The system may perform various transformations of raw sensor data into a format indicative of a particular condition. In one implementation, a psychological or medical condition has symptoms in which each symptom has one or more measurable events. Mappings between symptoms, events, sensor data, and sensor transformation functions may be supported.

24 Claims, 39 Drawing Sheets

Related U.S. Application Data continuation of application No. 16/536,588, filed on Aug. 9, 2019, now Pat. No. 11,633,103, which is a continuation-in-part of application No. 16/386,002, filed on Apr. 16, 2019, now abandoned, and a continuation-in-part of application No. 16/272,037, filed on Feb. 11, 2019, now Pat. No. 11,120,226.

(60) Provisional application No. 62/769,220, filed on Nov. 19, 2018, provisional application No. 62/726,883, filed on Sep. 4, 2018, provisional application No. 62/717,650, filed on Aug. 10, 2018.

(51) Int. Cl.

| | |
|---|---|
| ***A61B 5/16*** | (2006.01) |
| ***G06F 9/54*** | (2006.01) |
| ***G06F 17/18*** | (2006.01) |
| ***G06N 20/10*** | (2019.01) |
| ***G08B 21/04*** | (2006.01) |
| ***G10L 15/16*** | (2006.01) |
| ***G10L 25/30*** | (2013.01) |
| *G10L 19/00* | (2013.01) |

(52) U.S. Cl.

CPC ......... *G06N 20/10* (2019.01); *G08B 21/0423* (2013.01); *G10L 15/16* (2013.01); *G10L 25/30* (2013.01); *G10L 19/00* (2013.01)

(58) Field of Classification Search

CPC ....... G10L 15/02; G10L 15/063; G10L 15/12; G10L 15/07; G10L 15/08; G10L 15/20; G10L 15/22; G10L 15/26; G10L 15/30; G10L 15/1822; G10L 15/183; G10L 15/19; G10L 15/193; G06F 9/542; G06F 17/18; A61B 5/022; A61B 5/165; G06N 20/10; G08B 21/0423

See application file for complete search history.

(56) References Cited

U.S. PATENT DOCUMENTS

| | | | | |
|---|---|---|---|---|
| 9,723,149 | B2 | 8/2017 | Meng | |
| 9,798,343 | B2 | 10/2017 | Kaufman | |
| 9,934,780 | B2 | 4/2018 | Tzirkel-Hancock | |
| 10,235,990 | B2 | 3/2019 | Corelli | |
| 10,311,869 | B2 | 6/2019 | Weng | |
| 10,311,980 | B2 | 6/2019 | Kim | |
| 10,319,477 | B1 | 6/2019 | Bill | |
| 10,329,784 | B1 | 6/2019 | Corwin | |
| 10,543,137 | B2 | 1/2020 | Hayes | |
| 11,633,103 | B1 | 4/2023 | Nudd | |
| 12,057,112 | B1 | 8/2024 | Nudd | |
| 12,076,108 | B1 * | 9/2024 | Nudd | G06N 20/00 |
| 2003/0114736 | A1 | 6/2003 | Reed | |
| 2003/0200142 | A1 | 10/2003 | Hicks | |
| 2008/0235018 | A1 | 9/2008 | Eggen | |
| 2009/0256710 | A1 | 10/2009 | Duckert | |
| 2009/0307025 | A1 | 12/2009 | Menon | |
| 2011/0125844 | A1 | 5/2011 | Collier | |
| 2011/0151418 | A1 | 6/2011 | Delespaul | |
| 2012/0265024 | A1 | 10/2012 | Shrivastav | |
| 2014/0067730 | A1 | 3/2014 | Kozloski | |
| 2014/0163337 | A1 | 6/2014 | Horseman | |
| 2014/0377727 | A1 | 12/2014 | Yom-Tov | |
| 2016/0198047 | A1 | 7/2016 | Mccormack | |
| 2016/0287166 | A1 | 10/2016 | Tran | |
| 2018/0075763 | A1 | 3/2018 | Wainfan | |
| 2018/0226076 | A1 | 8/2018 | Kotti | |
| 2018/0294059 | A1 | 10/2018 | Savant | |
| 2018/0308487 | A1 | 10/2018 | Goel | |
| 2018/0357286 | A1 | 12/2018 | Wang | |
| 2019/0008583 | A1 | 1/2019 | Gallagher | |
| 2019/0130243 | A1 | 5/2019 | Penubothula | |
| 2019/0189253 | A1 | 6/2019 | Kartoun | |

FOREIGN PATENT DOCUMENTS

| | | | |
|---|---|---|---|
| WO | 2009120707 | A1 | 10/2009 |
| WO | 2013033655 | A1 | 3/2013 |

OTHER PUBLICATIONS

Austin et al., "A Smart-Home System to Unobtrusively and Continuously Assess Loneliness in Older Adults," IEEE Journal of Translational Engineering in Health and Medicine, Jun. 10, 2016, vol. 4, 11 pgs.

Aylaz et al., "Relationship Between Depression and Loneliness in Elderly and Examination of Influential Factors," Abstract only, Arch. Gerontol. Geriatr., US National Library of Medicine National Institutes of Health, Nov.-Dec. 2012, vol. 55, No. 3, pp. 548-554, abstract retrieved online from https://www.ncbi.nlm.nih.gov/pubmed/22487148, 1 pg.

Baez et al., "Personalized Persuasion for Social Interactions in Nursing Homes," Proceedings of the Personalization in Persuasive Technology Workshop, Persuasive Technology 2016, Salzburg, Austria, http://ceur-ws.org/Vol-1582/11Baez.pdf, May 4, 2016, 6 pgs.

Bansal, "Beginners Guide to Topic Modeling in Python," Analytics Vidhya, Aug. 24, 2016, retrieved online from https://www.analyticsvidhya.com/blog/2016/08/beginners-guide-to-topic-modeling-in-python/ on Apr. 8, 2019, 8 pgs.

Bird et al., "Natural Language Processing with Python—Analyzing Text with the Natural Language Toolkit: Chapter 5 Categorizing and Tagging Words," retrieved online from https://www.nltk.org/book/ch05.html on Apr. 8, 2019, 29 pgs.

Buchman et al., "Loneliness and the rate of motor decline in old age: the rush memory and aging project, a community-based cohort study," BMC Geriatrics, 2010, vol. 10, No. 77, 8 pgs.

Chen et al., "Gunrock: Building a Human-Like Social Bot by Leveraging," 2nd Proceedings of Alexa Prize (Alexa Prize 2018), Department of Computer Science, University of California, Davis, https://s3.amazonaws.com/dex-microsites-prod/alexaprize/2018/papers/Gunrock.pdf, 2018, 19 pgs.

Chiu et al., "Named Entity Recognition with Bidirectional LSTM-CNNs," Transactions of the Association for Computational Linguistics, vol. 4, Jul. 2016, pp. 357-370.

Fetzer Institute, "UCLA Loneliness Scale," Self Report Measures for Love and Compassion Research: Loneliness and Interpersonal Problems, at least as early as Feb. 16, 2019, 2 pgs.

Hawkley et al., "Loneliness Predicts Reduced Physical Activity: Cross-Sectional & Longitudinal Analyses," Health Psycho!., May 2009, vol. 28, No. 3, pp. 354-363.

Hayes et al., "Unobtrusive assessment of activity patterns associated with mild cognitive impairment," Alzheimers Dement., Nov. 2008, vol. 4, No. 6, pp. 395-405.

Hughes et al., "A Short Scale for Measuring Loneliness in Large Surveys: Results From Two Population-Based Studies," Res. Aging, 2004, vol. 26, No. 6, pp. 655,672.

Kaye et al., "Unobtrusive measurement of daily computer use to detect mild cognitive impairment," Alzheimers Dement., Jan. 2014, vol. 10, No. 1, 15 pgs.

Lardieri, "Study: Many Americans Report Feeling Lonely, Younger Generations More So," US News & World Report, May 1, 2018, retrieved from https://www.usnews.com/news/health-care-news/articles/2018-05-01 /study-many-americans-report-feeling-lonely-younger-generations-more-so on Apr. 8, 2019, 6 pgs.

Lowe et al., "The Ubuntu Dialogue Corpus: A Large Dataset for Research in Unstructured Multi-Turn Dialogue Systems," School of Computer Science, McGill University, Montreal, Canada, Feb. 4, 2016, retrieved from https://arxiv. org/abs/1506.08909, 10 pgs.

Machine Learning Plus, "Topic Modeling with Gensim (Python)," 2018, retrieved online from https://www.machinelearningplus.com/nlp/topic-modeling-gensim-python/, 43 pgs.

(56) References Cited

OTHER PUBLICATIONS

Manning et al., "The Stanford CoreNLP Natural Language Processing Toolkit," Proceedings of 52nd Annual Meeting of the Association for Computational Linguistics: System Demonstrations, Jun. 23-24, 2014, pp. 55-60.
Nemecek, "Cigna's U.S. Loneliness Index," May 2018, retrieved from https://www.multivu.com/players/English/8294451-cigna-us-loneliness-survey/, 61 pgs.
Petersen et al., "Phone behaviour and its relationship to loneliness in older adults," Aging Ment. Health, Oct. 2016, vol. 20, No. 10, pp. 1084-1091.
Petersen et al., "SVM to Detect the Presence of Visitors in a Smart Home Environment," Conf. Proc. IEEE Eng. Med. Biol. Soc., 2012, 9 pgs.
Petersen et al., "Unobtrusive in-home detection of time spent out-of-home with applications to loneliness and physical activity," IEEE J Biomed Health Inform, Sep. 2014, vol. 18, No. 5, pp. 1590-1596.
Reddit u/Stuck_In_the_Matrix, "I have every publicly available Reddit comment for research.—1.7 billion comments @250 GB compressed. Any interest in this?" ca. 2015, retrieved from https://www.reddit.com/r/datasets/comments/3bxlg7/i_have_every_publicly_available_reddit_comment/ on May 16, 2019, 5 pgs.
Relational Agents Group, "An Always on Relational Agent for Social Support," Relational Agents Group, Jan. 9, 2019, retrieved online from http://www.relationalagents.com/projects/15.html on Apr. 8, 2019, 1 pg.
Ring et al., "Addressing Loneliness and Isolation in Older Adults: Proactive Affective Agents Provide Better Support," 2013 Humaine Association Conference on Affective Computing and Intelligent Interaction, Geneva, retrieved from https ://ieeexplore. ieee. org/docu ment/6681408/ citations?tabFi lter=papers#citations, 6 pgs.
Russell, "UCLA Loneliness Scale (Version 3): Reliability, Validity, and Factor Structure," Journal of Personality Assessment, 1996, vol. 66, No. 1, pp. 20-40.
Shao et al., "Generating High-Quality and Informative Conversation Responses," EMNLP, arXiv: 1701.03185, Jul. 31, 2017, 11 pgs.
Unknown, "Language-Independent Named Entity Recognition (II)," 2003, retrieved online from https://www.clips.uantwerpen.be/conill2003/ner/, Apr. 8, 2019, 7 pgs.
Vargheese et al., "Persuasive Dialogue for Older Adults," CHI 2013 Changing Perspectives, Paris, France, Apr. 27-May 2, 2013, 6 pgs.
Vargheese et al., "Persuasive Strategies for Encouraging Social Interaction for Older Adults," International Journal of Human-Computer Interaction, vol. 32, No. 3, Jan. 4, 2016, retrieved from https://www.tandfonline.com/doi/full/10.1080/10447318.2016.1136176 on May 16, 2019, 6 pgs.
Glascock et al., The Impact of Behavioral Monitoring Technology on the Provision of Health Care in the Home, 2006, Journal of Universal Computer Science, vol. 12, No. 1 (2006), 59-79 (Year: 2006).
I\n Always on Relational Agent for Social Support, Relational Agents Group, Jan. 9, 2019, 1 pg.
Language-Independent Named Entity Recognition {II), hllps://www.clips.uantwerpen.be/coni112003/ner/, 2003, 7 pgs.
Topic Modeling with Gensim (Python), https://www.machineleamingplus.com/nlp/topic-modeling-gensim-python/, • 018, 43 pgs.
Tropic Modeling with Gensim (Python), https://www.machineleamingplus.com/nlp/topic-modeling-gensim-python/, • 018, 43 pgs.

* cited by examiner

| subject | row num. | condition | required sensors | install cost | costs and benefits | | | | | |
|---|---|---|---|---|---|---|---|---|---|---|
| | | | | | 1 year | | 2 years | | 3 years | |
| P | 1 | mild depression | $S_1$ | $IC_1$ | $MC_{1,1}$ | $B_{1,1}$ | $MC_{1,2}$ | $B_{1,2}$ | $MC_{1,3}$ | $B_{1,3}$ |
| P | 2 | stage 4 lung cancer | $S_2$ | $IC_2$ | $MC_{2,1}$ | $B_{2,1}$ | $MC_{2,2}$ | $B_{2,2}$ | $MC_{2,3}$ | $B_{2,3}$ |
| P | 3 | dementia | $S_3$ | $IC_3$ | $MC_{3,1}$ | $B_{3,1}$ | $MC_{3,2}$ | $B_{3,2}$ | $MC_{3,3}$ | $B_{3,3}$ |
| ... | ... | ... | ... | ... | ... | ... | ... | ... | ... | ... |
| C | n | job performance | $S_n$ | $IC_n$ | $MC_{n,1}$ | $B_{n,1}$ | $MC_{n,2}$ | $B_{n,2}$ | $MC_{n,3}$ | $B_{n,3}$ |

Subject P=patient, C=caregiver.

| no. | sensor | loc. |
|---|---|---|
| 1 | IR motion | B |
| 2 | ultrasonic motion | B |
| 3 | radar | B |
| 4 | smart speaker | B |
| 5 | video camera facing couch | L |
| 6 | smart speaker | L |
| 7 | smart speaker | K |
| 8 | video camera | K |
| 9 | ultrasonic motion | K |
| 10 | IR motion | BA |
| 11 | blood pressure | B |
| 12 | smart phone | P |
| 13 | smart watch | P |
| 14 | pedometer | P |
| 15 | smart phone | C |

(a) Sensor floor plan

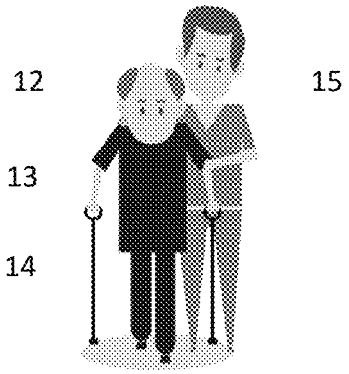

c personal

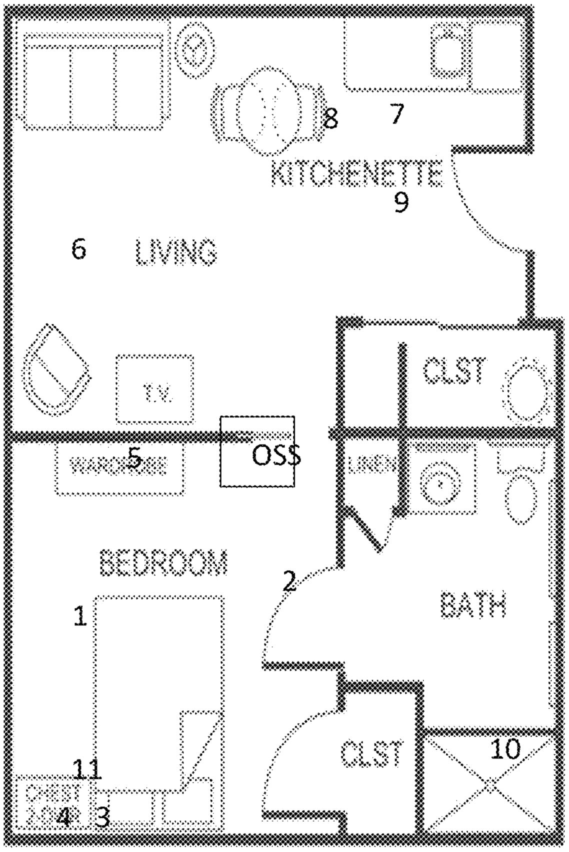

(b) floor plan

Locations B=bedroom, L=living room, K=kitchen, BA=bathroom, P=on patient, C=on caregiver.

Fig. 19

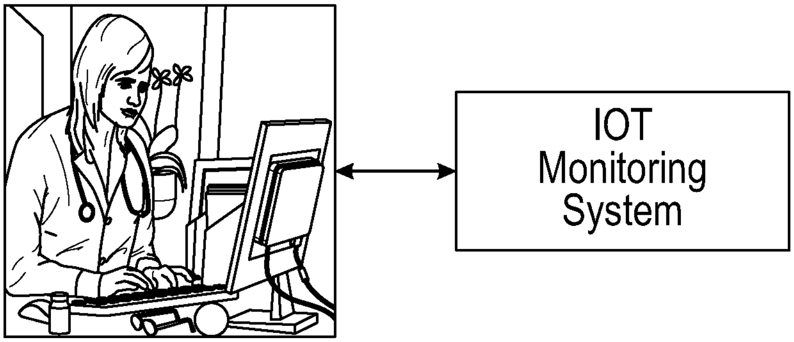
(a)
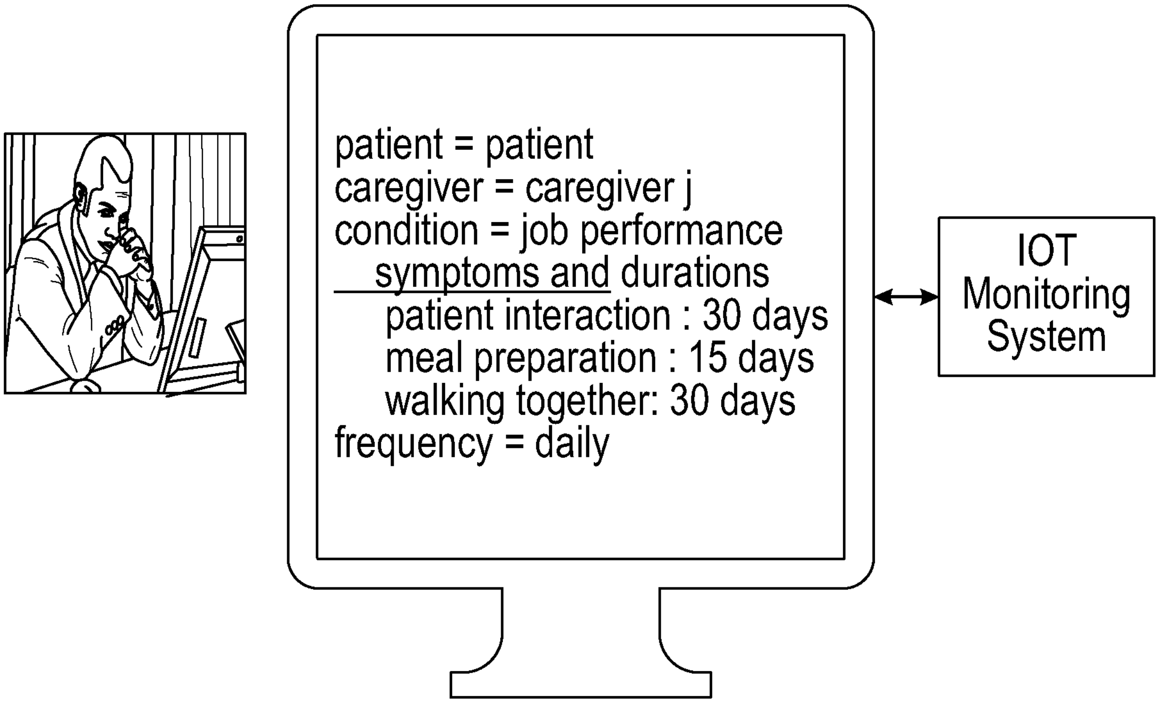
(b)
Configuration user Interface Examples for Monitoring Mild Depression in Patients (a) and Caregiver job Performance (b)
FIG. 20

| Condition | Symptom | Event | Location | Duration | Daily sampling rate |
|---|---|---|---|---|---|
| **Mild depression** | Sleep quality | Motion | B | 30 days | 4 |
| | | Respiration | B | 30 days | 4 |
| | | Heart rate | B | 30 days | 4 |
| | Mobility | Step count | A | 90 days | 4 |
| | | Stairs climbed | A | 90 days | 4 |
| | TV time | Minutes watched | A | 15 days | 2 |
| **Caregiver performance** | Patient Interaction | Conversation frequency | A | 30 days | 4 |
| | | Co-location | A | 30 days | 4 |
| | Meal preparation | Kitchen sounds | K | 15 days | 4 |
| | | Motion | K | 15 days | 4 |
| | Walking together | Step counts | A | 60days | 2 |
| | | Co-location | A | 60 days | 4 |

Symptom event (SE) table. Location B=bedroom, A=all locations, K=kitchen.

Fig. 22

| Event | Sensor | Detection rate | Event | Sensor | Detection rate |
|---|---|---|---|---|---|
| **Motion** | IR motion detector | 1 minute | **Step count** | Smart watch | 5 minutes |
| | Ultrasonic motion detector | 2 minutes | | Smart phone | 1 minute |
| | Radar motion detector | 2minutes | | Pedometer | 1 minute |
| | Smart watch pedometer | 5 minutes | **Stairs climbed** | Smart phone | 1 minute |
| | Smart phone pedometer | 1 minute | | Pedometer | 1 minute |
| | Video camera | 3 minutes | **TVtime** | Smart TV | 10minutes |
| **Respiration** | Smartwatch | 5 minutes | | Video analysis | 5 minutes |
| | Radar | 2 minutes | **Weight** | Smart scale | daily |
| | Smartspeaker | 1minute | **Speech pattern** | Smart speaker | 5 minutes |
| **Heart rate** | Smart watch | 5 minutes | | Smart phone | 1 minute |
| | Radar | 2minutes | **Conversation frequency** | Smart speaker | 5 minutes |
| | Blood pressure | 2 minutes | | Smart phone | 1 minute |
| **Co-location** | Smart phones 1 and 2 | 1 minute | **Kitchen sounds** | Smart speaker | 1 minute |

Event-sensor (ES) mapping table

Fig. 23

| Sensor | Install cost (IC) | Yearly mtce ·cost (MC) | Transform. function | Parameters |
|---|---|---|---|---|
| IR motion detector | 10 | 25 | downsample | detection rate, interval width (5) |
| ultrasonic motion detector | 20 | 25 | downsample | detection rate, interval width (5) |
| radar motion detector | 55 | 45 | downsample | detection rate, interval width (5) |
| video camera | 45 | 25 | video_motion | frame_rate sampling_window (1) intervalwidth (5), pct_diff (15) |
| smart watch pedometer | 450 | 35 | downsample | detection rate, interval width (20) |
| smart watch respiration rate | 450 | 35 | downsample | detection rate, interval width (30) |
| radar respiration rate | 55 | 45 | downsample | detection rate, interval width (30) |
| smart speaker respiration rate | 55 | 25 | downsample | detection rate, interval width (30) |
| Smart watch heart rate | 450 | 35 | downsample | detection rate, interval width (10) |
| radar heart rate | 55 | 45 | downsample | detection rate, interval width (10) |

Example sensor transformation (ST) function table

Fig. 24A

| Sensor | Install cost | Yearly mtcecost | Transformation function | Parameters |
|---|---|---|---|---|
| blood pressure cuff heart rate | 35 | 10 | null | None |
| Pedometer (stand alone) | 10 | 15 | downsample | detection rate, interval width (20) |
| smart phone stair counter | 450 | 35 | downsample | detection rate, interval width (30 |
| pedometer stair counter | 10 | 15 | downsample | detection rate interval width (30) |
| smart TV video camera | 68 | 35 | motion_detect | video frame rate interval width (5) |
| smart scale | 120 | 35 | null | None |
| Smart speaker speech pattern | 55 | 25 | speech_analysis | prior recorded speech |
| Smart phone speech pattern | 450 | 35 | speech_analysis | prior recorded speech |
| smart speaker conversation freq. | 55 | 85 | conversation_analysis | speech samples for known people |
| smart phone conversation freq. | 450 | 85 | conversation _analysis | speech samples for known people |
| smart phone colocation | 900 | 70 | combine and downsample | detection rate, interval width (5) |

Example sensor transformation (ST) function table.

Fig. 24B

Machine learning system to identify condition c in patient i and/or caregiver j.

| | | | | |
|---|---|---|---|---|
| $e_1$ | $v_{i,1}$ | $v_{i,2}$ | ... | $v_{n1,d1}$ |
| $e_2$ | ... | ... | ... | ... |
| ... | ... | ... | ... | ... |
| $e_n$ | $v_{n,1}$ | $v_{n,2}$ | ... | $v_{nn,dn}$ |

Normalized feature vector construction

| | patient with mild depression | | | | patient without mild depression | | | |
|---|---|---|---|---|---|---|---|---|
| events | Midnight - 6AM | 6 AM - noon | Noon - 6PM | 6 PM - midnight | Midnigh t - 6AM | 6 AM - noon | Noon - 6PM | 6 PM - midnigh t |
| motion | 435 | 12 | 33 | 50 | 35 | 870 | 960 | 430 |
| respiration | 22 | 21 | 18 | 19 | 14 | 25 | 22 | 32 |
| heart rate | 65 | 67 | 63 | 62 | 50 | 75 | 80 | 85 |
| step count | 120 | 110 | 105 | 130 | 0 | 450 | 1100 | 620 |
| stairs climbed | 0 | 0 | 0 | 0 | 0 | 25 | 18 | 0 |
| TV time | 360 | | 720 | | 20 | | 30 | |

Example normalized feature vectors for patients with and without mild depression

Fig. 27

| | caregiver with good job performance | | | | caregiver with poor job performance | | | |
|---|---|---|---|---|---|---|---|---|
| events | midnight – 6AM | 6 AM – noon | noon –6PM | 6PM – midnight | midnight – 6AM | 6AM – noon | noon –6PM | 6PM – midnight |
| conversation frequency | 35 | 2 | 126 | 150 | 2 | 0 | 4 | 7 |
| Co-location | 56 | 256 | 204 | 122 | 10 | 166 | 88 | 12 |
| kitchen sounds | 23 | 35 | 43 | 12 | 15 | 23 | 34 | 0 |
| motion (in kitchen) | 145 | 224 | 207 | 154 | 43 | 54 | 62 | 0 |
| step count | 360 | | 720 | | 20 | | 30 | |

Example normalized feature vectors for a caregivers with and without good job performance

Fig. 28

Learn decision thresholds for logistic regression and Green, Yellow, Red (GYR) classifier.

Train the LR classifier (a) and adjust thresholds (b) for GYR levels.

Learn decision thresholds for logistic regression and Green, Yellow, Red (GYR) classifier.
Train the LR classifier (a) and adjust thresholds (b) for GYR levels.

Example user interface for agency owner or manager

AUTOMATIC IN-HOME SENIOR CARE SYSTEM AUGMENTED WITH INTERNET OF THINGS TECHNOLOGIES

CROSS-REFERENCE TO RELATED APPLICATIONS

This application is a continuation of U.S. patent application Ser. No. 18/304,669, entitled "Automatic In-Home Senior Care System Augmented With Internet of Things Technologies", filed Apr. 21, 2023, which is a continuation of U.S. patent application Ser. No. 16/536,588, entitled "Automatic In-Home Senior Care System Augmented With Internet of Things Technologies", filed Aug. 9, 2019, and is a continuation-in-part of U.S. patent application Ser. No. 16/386,002, entitled "LONELINESS DETECTION AND MONITORING SYSTEM," filed Apr. 16, 2019, and is a continuation-in-part of U.S. patent application Ser. No. 16/272,037, entitled "CONVERSATION FACILITATION SYSTEM FOR MITIGATING LONELINESS," filed Feb. 11, 2019, and claims priority under 35 USC § 119 (e) to U.S. Provisional Patent Application No. 62/769,220, filed Nov. 19, 2018, entitled "SENIOR CARE SOCIALIZATION AND MONITORING SYSTEM," and to U.S. Provisional Patent Application No. 62/726,883, filed Sep. 4, 2018, entitled "CONVERSATION-BASED SYSTEM FOR MITIGATING LONELINESS," and to U.S. Provisional Patent Application No. 62.717,650 62/717,650, entitled "AUTOMATIC IN-HOME SENIOR CARE SYSTEM AUGMENTED WITH INTERNET OF THINGS TECHNOLOGIES," filed Aug. 10, 2018, the entirety of which are herein incorporated by reference.

TECHNICAL FIELD

Embodiments of the disclosure relate to supporting assisted living care at home through technology assisted monitoring. More particularly, embodiments of the disclosure are related to monitoring aspects of a living space and using the collected information to improve the assisting living care. An exemplary application is for monitoring signs of the symptoms of a psychological or medication condition, such as monitoring for signs of depression or other conditions.

BACKGROUND

Assisted care living is an increasingly common option for taking care of people in their home. For example, a senior citizen may require assistance at home several days a week.

A variety of different parties are part of an assisted care living scenario. For example, the client may, for example, be a senior citizen (a "senior" who is also a "patient" of a doctor or health care system and a "client" of home care) requiring in-home care. Seniors are one example of clients needing home assistance, although of course there are other examples of people needing home care assistance, such as people with severe disabilities, chronic conditions, functional limitations, social determinants of health, behavioral factors, etc. The caregivers may be associated with an agency that provides home care. Other parties that may be involved in different ways include families, payees (e.g., insurance companies or government health programs), and health care providers (e.g., doctors, medical clinics, etc.).

However, there is increasing pressure to improve the quality and cost of providing in-home care.

Embodiments of this disclosure were developed in view of these considerations.

SUMMARY

An apparatus, system, method, computer program product, and machine learning system is disclosed to augment in-home care of seniors. In one embodiment, sensors in internet of things (IOT) devices and other user devices are monitored. Information on the senior and their caregiver is monitored and analyzed. This information may be used to detect a medical or psychological condition of the senior.

In one embodiment, a machine learning subsystem is configured to monitor the sensor outputs from a senior's living area, map the sensor outputs to events associated with features of symptoms of a selected psychological or medical condition, and apply a machine learning model trained to determine a likelihood that the senior has the psychological or medical condition based on the sensor outputs. In one embodiment, a classifier is trained to determined thresholds for identifying a psychological or medical condition.

In one embodiment, the system identifies a first relationship between symptoms of the psychological or medical condition and events, wherein the events are physical or mental features associated with at least one of the symptoms; identifies a second relationship between the events and the sensor outputs based at least in part on the locations of each sensor and a sensor type of each sensor; and identifies a third relationship of sensor transformations required to transform raw sensor data into a format indicative of events.

In one embodiment, the system also identifies a set of sensors, sensor types, and sensor locations to detect a selected condition for a caregiver or a patient. In one implementation, a cost-benefit analysis is generated.

In one embodiment the sensor data is selected from: a voice assistant appliance; a video assistant appliance; a smart phone; a tablet computer; a smart watch; a smart appliance; a personal computer; or a home monitoring system.

BRIEF DESCRIPTION OF THE DRAWINGS

FIG. 19 illustrates an example of a sensor configuration in a senior's living space in accordance with an embodiment.

FIG. 20 illustrates an example of configuration user interface in accordance with an embodiment.

FIG. 22 illustrates a symptom-event (SE) table in accordance with an embodiment.

FIG. 23 illustrates an event-sensor mapping table in accordance with an embodiment.

FIGS. 24A and 24B illustrate different portions of a sensor transformation (ST) function table in accordance with an embodiment.

FIG. 27 illustrates an example of normalized feature vectors for patients in accordance with an embodiment.

FIG. 28 illustrates an example of normalized feature vectors for caregivers in accordance with an embodiment.

DETAILED DESCRIPTION

Augmenting Home Care with IOT Technologies

The present disclosure describes systems and methods for facilitating in-home care of seniors. In the following descriptions, for purpose of explanation, numerous specific details are set forth in order to provide a thorough understanding of the present disclosure. However, it should be noted that the present disclosure might be practiced without these specific details.

Figure 1A:
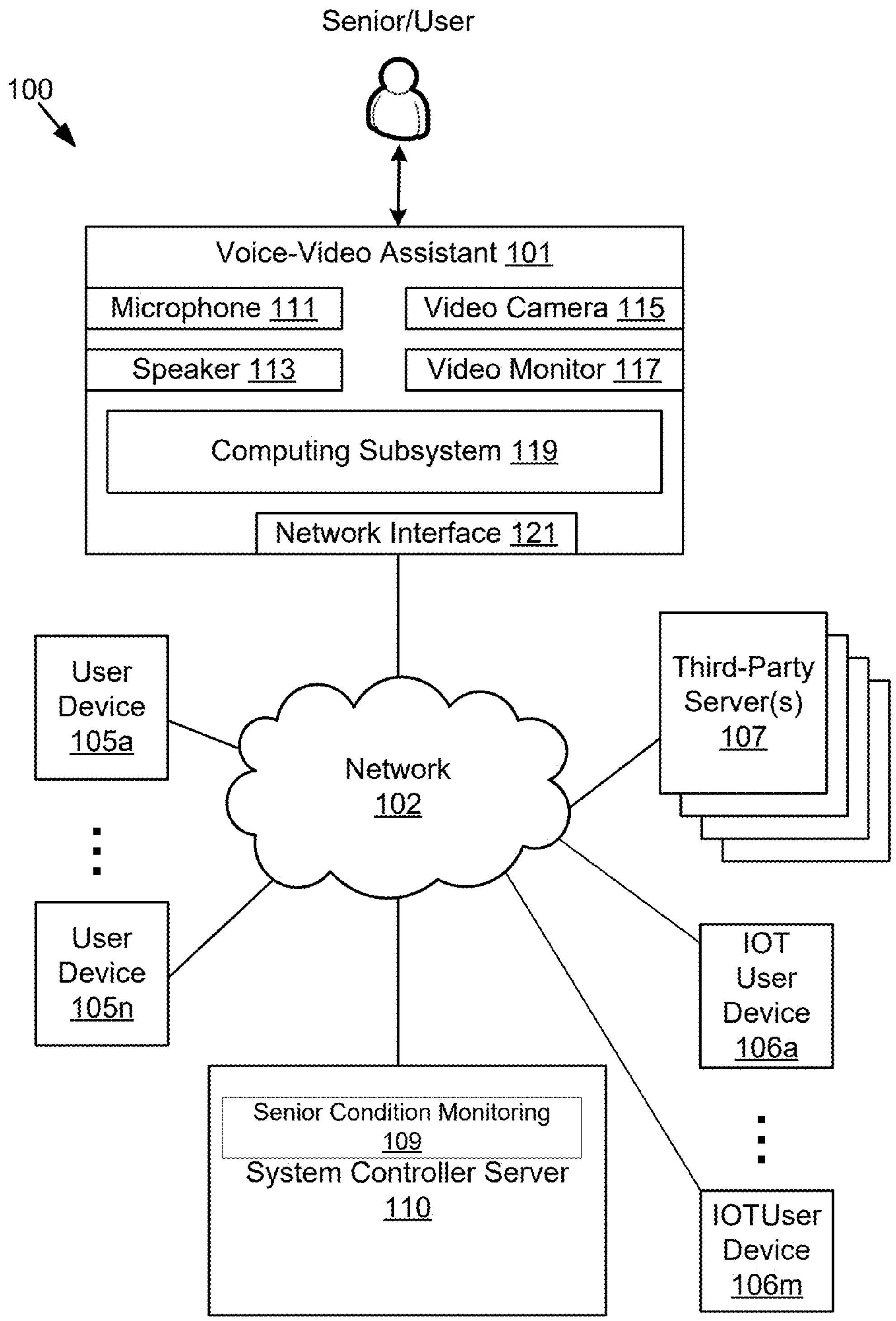
FIGS. 1A-1G illustrates a system architecture for augmenting in-home care with IOT devices in accordance with an embodiment.
Figure 1B:
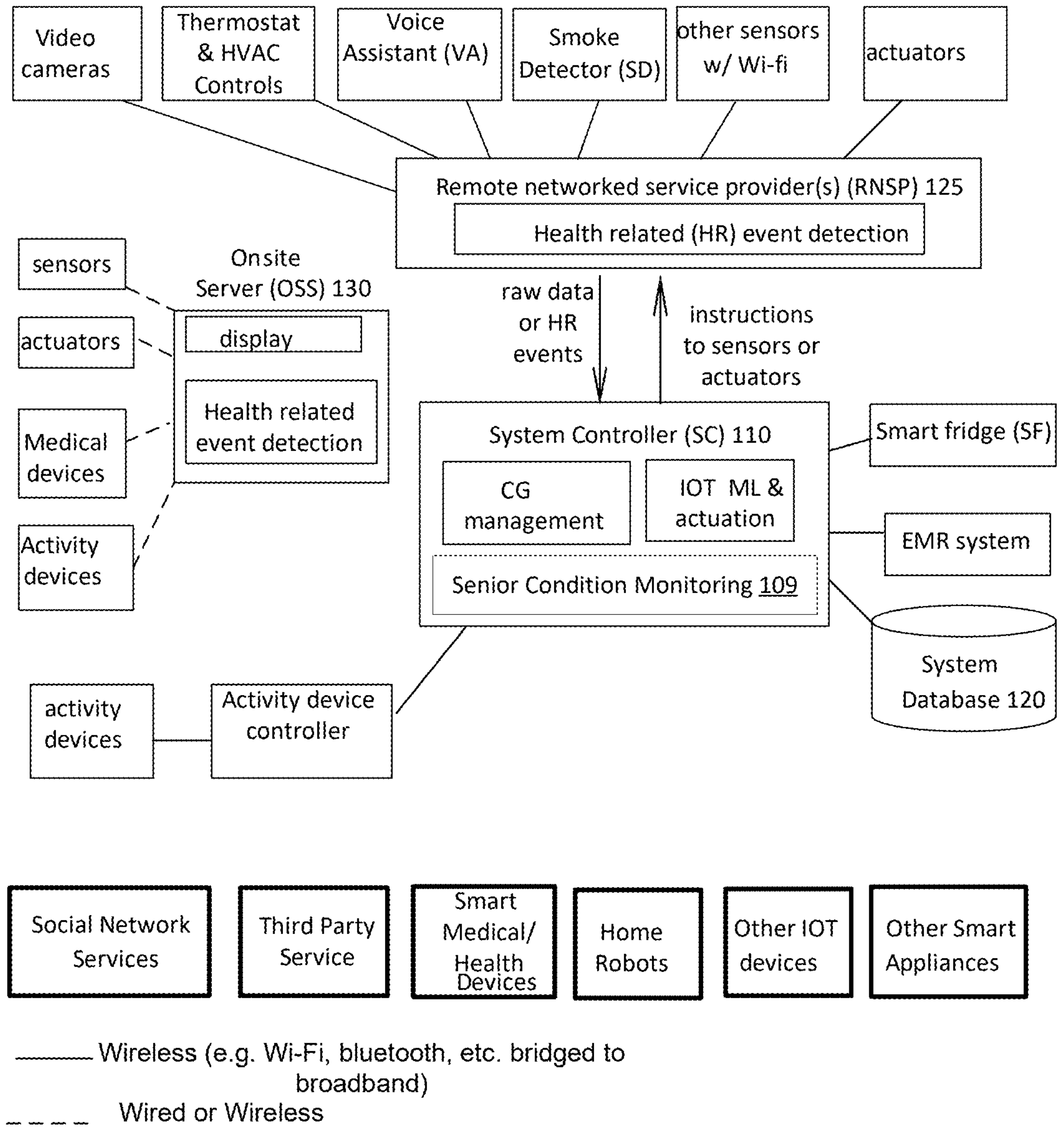

FIG. 1A is a block diagram illustrating an example system 100 for facilitating care of seniors. As illustrated, the system 100 may include a voice-video assistant (VVA) 101, a server 110, one or more user devices 105*a* . . . 105*n*, one or more user Internet of Thing (IOT) devices 106*a* . . . 106*m*, and one or more third-party servers 107, which connect with each other via a network 102.

The voice-video assistant (VVA) 101 includes hardware, software, and/or firmware for allowing a participant to join and conduct a conversation with other participants. In some embodiments, the VVA 101 may include a microphone 111, a speaker 113, a video camera 115, a video monitor 117, a computing subsystem 119, and a network interface 121. The VVA 101 receives, processes, and outputs audio data through the microphone 111 and the speaker 113. The VVA 101 may also use the optional video camera 115 and video monitor 117 to receive, process, and display video data. The video monitor 117 may be associated with a touchscreen and clickable button(s) to facilitate interactions with a user. The computing subsystem 119 of the VVA 101 includes other components, such as a processor, memory, storage, required for the VVA 101 to perform its function described herein. The network interface 121, which may also be part of the computing subsystem 119, communicates the VVA 101 to other entities of the conversation facilitation system 100 through a wire connection or a wireless connection.

As a networked device used by a participant to join and conduct a conversation, typically, the VVA 101 is a "smart speaker" such as the Amazon® Alexa, Google® Home, or Apple® Home Pod. In the scenario that the VVA 101 also handles video input and output, the example VVA devices with such video processing functionality may be the Amazon® Echo Show, Lenovo® Smart Display, and Harman® JBL Link View. Additionally, the VVA 101 may be a smart computing device (e.g., smartphone) equipped with an appropriate software application for providing the functionality of allowing a participant to join and conduct a conversation with other participants.

The server 110, which in some embodiments is a system controller, includes hardware, software, and/or firmware that manages and facilitates implementing a care plan for a senior/user. In some embodiments, the server 110 includes an interface to receive sensor data from user devices 105 and IOT devices 106. As discussed below in more detail, a wide variety of wired and wireless network communication techniques may be employed for the server 110 to receive the sensor data.

In one embodiment, the server 110 includes a senior monitoring module 109 to monitor a psychological or medication condition based on the outputs of sensors in the seniors living area associated with the user devices 105 and IOT devices 106.

The third-party server 107 includes one or more computing devices or systems for providing various computing functionalities, services, and/or resources to other entities included or not included in the system 100. In some embodiments, the third-party server 107 hosts a network-based software application operable to provide computing functionalities, services and/or resources or functionalities, and to send data to and receive data from the other entities.

The user devices 105*a* . . . 105*n* or collectively referred hereafter as user device 105 is a computing device including a processor, a memory, applications, a database, and network communication capabilities. For example, the user device 105 can be a laptop computer, a desktop computer, a tablet computer, a mobile telephone, a personal digital assistant (PDA), a mobile email device, a television with one or more processors embedded therein or coupled thereto or any other electronic device capable of accessing the network 102 and communicating with other entities of the system 100.

The Internet of Thing (IOT) devices 106*a* . . . 106*m* may include IOT devices having a processor, memory, a sensor or actuator, and a network communication capability. The IOT devices 106 may comprise IOT devices such as home appliances and other items embedded with electronics, software, sensors, actuators, and network connectivity that permits these things to connect and exchange data. Other examples of IOT devices are described below in more detail.

The network 102 includes hardware, software, and/or firmware that provide communications between the VVA 101, the system controller 110, the user devices 105*a* . . . 105*n*, and the one or more third-party servers 107. In some embodiments, the network 102 may be a conventional type, wired and/or wireless, and may have numerous different configurations including a star configuration, token ring configuration, or other configurations. For instance, the network 102 may include one or more local area networks (LAN), wide area networks (WAN) (e.g., the Internet), satellite networks, telephone or cable networks, cellular networks, public networks, private networks, virtual networks, peer-to-peer networks, wireless networks implemented using a wireless protocol such as WiFi® or WiMax®, and/or any other interconnected data paths across which multiple devices may communicate. Although FIG. 1 illustrates a single block for the network 102, it should be understood that the network 102 may in practice comprise any number of combinations of networks, as noted above.

Internet of things (IOT or IoT) technologies are used in embodiments of this disclosure to augment in-home care. The IOT technologies support monitoring the home environment of a patient (also described as a "senior"). This data may be utilized to monitor aspects of the care of the patient in some embodiments. In some embodiments this also permits new ways of interacting with the patient as part of their care. Other embodiments including monitoring aspects of the caregiver and how they interact with the client.

Additional technical details of the IOT system are described in other patent applications of the assignee. This application incorporates by reference U.S. patent application Ser. No. 16/386,002 LONELINESS DETECTION AND MONITORING SYSTEM, filed on Apr. 16, 2019. This application also incorporates by reference U.S. patent application Ser. No. 16/272,037 CONVERSATION FACILITATION SYSTEM FOR MITIGATING LONELINESS, filed on Feb. 11, 2019. This application also incorporates by reference U.S. Prov. App. No. 62/726,993, filed on Sep. 4, 2018.

As the IOT evolves, there are more and more examples of the IOT implemented in home residences including, for example, a variety of home residence sensors, actuators, smart appliances, and home assistants. As will be described in greater detail below, the IOT may be used to augment in-home care in different ways.

As a non-exclusive set of examples, NEST Labs™ has home automation products that include programmable, self-learning, sensor-driven and networked thermostats, smoke detectors, security cameras, and security systems including smart video doorbells/door openers with facial recognition. Support is provided for third party devices to communicate with NEST™ products.

A variety of voice-controlled intelligent personal assistants are available such as Amazon Echo's Alexa™. Alexa can control smart devices and act as a home automation hub. These voice-controlled intelligent personal assistants can also be upgraded with additional skills. For example, Echo™ devices support third-party developed voice experiences to be added to an Alexa™ enabled device (such as the Echo) to add skills such as setting an alarm, getting an Uber ride, etc. Additionally, the Alexa Skills Kit™ includes APIs for developers to add skills to teach Alexa™ to control cloud-controlled lighting and thermostat devices. Google Home™ is another example of a voice controlled intelligent personal assistant. Google Home™ provides support for integrated home automation, including control of NEST™ products and a variety of smart devices.

Additionally, a variety of smart home appliances are available. These include, for example, smart refrigerators, smart home health care appliances, etc. These smart home appliances are also aspects of a smart home.

Moreover, a variety of consumer devices are capable of interacting with IOT devices. For example, many types of smart watches and smartphones may interact with IOT devices.

In one embodiment, a suite of IOT devices and services are integrated together to augment in-home care of an in-home care system. This may be implemented in different ways, such as by providing a remote server to facilitate communication between home-based IOT devices, apps for wireless smartphones or computers, a system supporting in-home health care, and integration with care providers. Apps for family members to receive information may also be provided. Additionally, in some implementations, one or more support services may be implemented as a cloud-based service.

Moreover, in the context of in-home care, the IOT system may provide sensor data that is analyzed in ways customized to in-home care. For example, in an in-home care scenario a care provider may be assigned tasks such as ensuring that the client takes their required medication, checking the client is eating in accordance with a dietary plan, performing recommended exercises, and so on. The sensor data from IOT devices may be analyzed to detect attributes related to the quality of the in-home care, to determine how the caregiver is doing, etc. Additionally, the actuators of the IOT devices may be utilized to help implement in-home care. For example, home security devices may be used to let an authorized caregiver into the home and in-home security cameras used to confirm that the caregiver is performing assigned tasks and not performing unauthorized acts.

A variety of voice-controlled intelligent personal assistants may be utilized in a complete system, including voice-controlled intelligent personal assistants in the client's home, voice controlled intelligent personal assistants for caregivers, and voice controlled intelligent personal assistants for family members.

In one embodiment, the IOT system may be used to augment in-home care related to how caregivers interact with their client (e.g., interactions between a caregiver and a senior). Other aspects of in-home care may also be augmented by the IOT.

For example, the IOT system may be used to augment in-home care by providing information on caregivers such as the following non-exclusive list:

- Sensing caregiver mental state using the sensors, including analysis of audio content, video content, such as an analysis of words used, vocal characteristics, body language, etc. of at least the caregiver and possibly also the senior.
  - Detection of emotional state, or change of emotional state, of the caregiver or senior
  - Detection of stress, or change in stress, of the caregiver or senior
  - Detection of mental acuity, or changes in mental acuity, of the senior
  - Ability to capture relationship quality between senior and caregiver
  - Evaluating the caregiver's interactions with the senior
  - Evaluating how well the caregivers are doing tasks
  - Providing training opportunities for caregivers
  - Detecting Abuses/Abusive behavior by the caregiver
- Clock-in and clock-out of Caregiver, tasks, etc.
- Caregiver ID—electronic visit verification
- Unconscious capture and monitoring of a caregiver activity and prompting
- Real time service of training tips

- Dispute resolution-theft, complaints, caregiver safety/senior abuse (valuable for dementia)
- Caregiver safety—injuries, safe lifting, etc.
- Caregiver rankings, ratings, and SLAs
- Ability to extend functionality via the mobile phone device assistant
- Track the daily log and publish the feed
- Interacting with voice-activated assistants in HIPAA eligible and secure manner
- Ability to determine caregiver activity based on data from accelerometer and microphone on the caregiver's phone
- Multi-modal homecare monitoring smart watches, smart phone, Microsoft kinect (gaming console sensors), voice activated home assistants (Alexa, Google Home Mini), video/image capture devices (Nest, home video monitors)
- Acquiring the data feed off of the caregiver's phone, or integration to the servers with social feed As another example, the IOT system may be used to augment in-home care by providing information to aid an Agency to provide services such as the following non-exclusive list for an agency:

- Scheduler
- Matching of caregivers based on changes in care requirements, or personality/fit
- Care manager
  - Use the data to determine recommended changes to the amount or type of homecare
- Home care agency administrator
- Family advisory-here is what we are observing, here is what we would expect
- An ability to match with the right agency/right caregiver
  - Could be a specific agency
  - Could be a specific caregiver within the agency
  - Ability to assign based on a model on the first referral
  - Ability to assign to a specific caregiver As another example, the IOT may be used to augment in-home care by providing information to aid seniors to provide services such as the following non-exclusive list for seniors:

- Health conditions-myriad
- Lyft/uber integration
- Social/functional trend
- App usage
- Following the care plan—is it effective
  - New drug—is it working
  - New physical training (PT program)—is it working
- Informing AI bots to support connectivity
- AI bots to support prompts
- Ability to connect with others-virtually or in person
- Prompts/data feed to family
- Tracking eating and drinking As another example, the IOT may be used to augment in-home care by providing information for families of a senior, such as the following non-exclusive list for families

- Ability to receive data feed, alerts as well as connect through the system

For example, the IOT may be used to augment in-home care by providing information for payers/providers such as the following non-exclusive list for Payers/Providers.

- Data for clinical decision support
- Med/care plan adherence
- Establishing baseline and changes/forecasted new baseline
- Integrated care
  - Data sharing
  - Signaling between the right parties
- Notifications
- Could be data, could be prescribed action The IOT device for in-home care may include a variety of different devices associated with the senior's home as well as other devices and systems. Depending on implementation details, different IOT devices may be used. A partial list of IOT Devices for augmenting in-home care, includes:

- Cameras
- Audio
- HVAC control
- Wearables
- Lighting
- Other smart devices-smart toilet, toaster, fridge, etc.
- Video game controllers and devices
- VR devices
- Vehicles
- Other data systems
- EMR/EHR
  - Patient medical record
  - Insurance systems.
  - Blockchain or cryptographic health record/health graph
- Social networks
- Search profile A variety of backend support features may be provided for security, encryption, integration of different devices, etc. Some of the backend support features may include one or more of:

- Support for HIPAA eligible, security
- Encryption algorithm on top of Alexa or Google Home
- Ability to integrate to multiple devices such as those manufactured by
  - Google
  - Amazon
  - Microsoft Additionally, the IOT system may be used to capture data related to a senior's condition over time. For example, IOT data from an individual senior may be tracked over time to create a timeline of health-related data that may be indicative of trends. Moreover, in some embodiments, data is analyzed for multiple seniors have similar demographic and medical issues to identify trend patterns. For example, while there are individual differences in how patients decline in health over time for particular medical conditions, there may be correlations between changes in IOT data for particular medical conditions. For example, by collecting IOT data for a large population of seniors having in-home care, it is statistically likely that there will be clusters of seniors that exhibit similar trends in health and IOT data (e.g. trends of IOT data for seniors between ages 80 to 85 about to enter stage 3 congestive heart failure).

As an example, consider Alzheimer's disease, which tends to develop slowly and gradually worsens over the years. In the early stages there is mild cognitive impairment. This progresses to mild dementia in which the person afflicted has significant trouble with memory and thinking that impacts daily functioning. The next phase is moderate dementia, which includes increasingly poor judgment and deepening confusion, more changes to personality and behavior. The final stage is severe dementia. There is some research that diet, exercise, and therapeutic exercise can reduce some of the symptoms of Alzheimer and may slow the progression of the disease. IOT data for a patient collected over time may reveal data relevant to the progression of the disease, such as changes to speech patterns and behavior. Moreover, IOT monitoring and recommendations to the senior or caregiver may be automated in the earlier stages of a patient's progression with Alzheimer's, with an increasing role of manual "hands on" interventions driven by a non-medical caregiver or clinician as acuity increases.

Additional Exemplary IOT System Architecture

FIGS. 1B-G show aspects of an IOT system architecture in accordance with an embodiment. One application of the IOT system architecture is to augment in-home care of a senior.

IOT devices require a capability to communicate via a network connection, such as via a wireless connection. The network connection may be implemented in different ways such that in one embodiment the IOT architecture is open to different techniques to connect with individual IOT devices. Also, the IOT architecture is illustrated with different types of IOT devices and other devices. In a specific implementation, however, greater or lesser numbers and varieties of IOT and other devices may be employed for a particular home residence.

In one embodiment, the architecture utilizes at least one remote networked service provider (RNSP) 125 to access IOT devices such as video cameras, thermostats & HVAC controls, a voice assistant, a smoke detector, other sensors, and actuators. For example, wireless sensors and actuators in the home residence environment of a client (hereinafter "a senior") are connected via at least one remote networked service provider (RNSP) over a network connection, such as via a WAN connection. Examples of RNSPs include Amazon™, Alexa™, and Google™

The RNSP 125 optionally is modified to include methods for detection of health-related (HR) events. The detection of HR events converts raw sensor data to events that are relevant to the health and care of the senior. As examples, this may be in the context of the senior being cared for by a caregiver, when the senior is alone, or when the senior is being attended to by a family member. The HR events may be directly related to a short-term danger to a senior's health. For example, an event would be the senior depicted in the video captured on the cameras falling down on the floor. HR events may also be related to a care plan for the senior (e.g., medications, diet plan, exercise plan), general health information (e.g., sleep patterns, toilet behavior etc.) HR events may also include detecting risk factors (e.g., poor quality air in the senior's home, low lighting or other factors increasing the risk of a potential fall, etc.). However, more generally, the HR events may encompass social, behavioral, or other aspects. For example, some studies indicate the loneliness can be as big a health risk as obesity such that social interactions are important for long-term senior health care.

In some embodiments, other home residences, such as those of family members of the senior, may also use IOT devices to connect wireless sensors and actuators in their home environments, such as a voice assistant.

The RNSP 125 provides raw data or HR events to a System controller (SC) and receives instructions to sensor and actuators.

In one embodiment, the SC 110 contains a Care Giver (CG) management module that recommends CGs for particular seniors, allows CGs to sign up for shifts, tracks the times when CGs arrive and depart, suggests and tracks the task and care protocols to be performed, provides medication reminders and/or verifies medication adherence in conjunction with other devices or sensors, etc. The SC 110 may include hardware elements (e.g., processors, internal communication buses, network interfaces, memory, and machine learning/AI processors). Some functions may be controlled with computer program instructions implemented as firmware or as software (e.g., computer program code stored on a non-transitory computer readable medium and executable by a processor).

In one embodiment the SC 110 controls the IOT system with an IOT machine learning (ML) and actuation module. It receives raw sensor data or HR events from the RNSP 125, determines how and when to respond, and sends the appropriate instructions back to sensors or actuators connected to the RNSP 125.

In one embodiment, the same functions are performed with sensors and actuators directly connected to the SC 110 or connected to the SC 110 through an on-site server (OSS) 130. That is, in one embodiment the architecture supports different techniques to access IOT devices such as video cameras, thermostat & HVAC controls, voice assistant, smoke detector, other sensors, and actuators.

In one embodiment, the architecture supports additional sensor and actuation functions. Some examples include those that are provided by a smart appliance; such as a smart fridge (SF); EMR system; smart phones that belong to the senior; smart phones that belong to caregivers; and smart phones that belong to family members; and the senior's laptop and activity device controller.

Example sensors connected to the RNSP 125 include video cameras that can be positioned throughout a senior's living area and placed to capture their activities of daily living. The raw video data can be converted to various HR events by computer vision techniques. For example, the computer vision techniques may utilize pattern recognition techniques to recognize HR events. Alternatively, artificial intelligence techniques may be used to train an AI engine to recognize specific HR events from the video data. Smart video cameras can be programmed to detect HR events using on-board hardware devices that receive raw video and/or audio data as input and output symbolic events, such as the Google Tensor Processing Unit (TPU) "a custom chip optimized for its machine learning framework TensorFlow-optimized for inference in edge devices."

An example of HR events of interest includes the senior eating, sleeping, visiting the bathroom, talking with other people, receiving medication, etc. Face and activity recognition technologies can be applied to verify who is shown in the video and what they are doing. For example, "At 3:02 PM caregiver Margaret helped senior Pam to get out of bed and go to the bathroom." In some applications, individual sensors, such as video cameras, motion sensors, thermal sensors, and the voice assistant may be used to detect when a senior is sleeping. However, there are an increasing number of commercial products that track sleep patterns.

In one embodiment, thermostat and HVAC controls monitor the environment in a senior's living area and communicate that information to the RNSP. It sends commands to the thermostat that adjust the heating and cooling system according to patterns of behavior of people in the senior's living space. In addition, the thermostat and HVAC controls can receive commands from the SC 110 that adjust the environment according to prescribed medical needs of the senior. For example, the senior's physician could indicate to an EMR system that the senior's room temperature should be set to 80 degrees and the fan should be set on high at night. The SC 110 would convert this instruction to commands that are sent to the thermostat and HVAC controls through the RNSP.

In one embodiment, Voice assistants (VAs) listen to conversations and act as intelligent assistants. VAs may, for example, be used to recognize words in speech. However, they can also be used to recognize speech patterns, voice stress; mental acuity; depression; interpersonal actions; emotional states or other mechanisms indicative of loneliness; and emotional tone. This information can be used in different ways to generate HR events. The VAs can also be used to identify the speech from individuals and the course of conversations.

In one embodiment, VAs passively listen to conversations, recognize what is being said, output transcribed speech, and initiate two-way conversations between an on-site user of a VA and a user of a VA at another location or a smart phone user. Speaker identification technologies can determine who said what. For example, a variety of speaker identification technologies are based on pattern recognition technologies to process and store voice prints. Voice-to-text techniques allow requests, commands, or questions to be interpreted as HR events.

In one embodiment, HR events include messages from the senior such as "I feel dizzy, please send help."

In one embodiment, a caregiver can provide information about the senior such as "Pam seems much groggier than normal. I think her physician should be notified."

In one embodiment, a caregiver can also send messages to the SC such as "Pam is increasingly talking about how much she misses her daughter."

In one embodiment, HR event detection also includes analysis of voice stress in terms of physiological/emotional stress. Emotional stress or physical fatigue can cause measurable changes in the voice signals of an individual. This can include, for example, changes to pitch or other attributes of speech. In particular, voice stress recognition allows for the detection of arguments between the caregiver and the senior. An example HR event would be "At 5:37 PM caregiver Margaret argued with senior Pam about taking her medication." The stress recognition based on voice stress may also be combined with other sources of voice information (e.g., words, patterns of words, phrasing, etc. indicative of stress, such as the use of swear words). Additionally, other aspects of body language may be detected from in-home cameras that may be indicative of stress and combined with the voice stress analysis (e.g. scrunched face associated with anger or frustration).

In one embodiment, HR event detection includes an analysis of loneliness based on a combination of factors including but not limited to the level of interpersonal interaction and analysis of emotional state.

Conversely, the HR event detection could include an analysis of voice attributes indicative of low stress or otherwise indicative of friendly conversations between the caregiver and the senior (and may also be combined with other sources of voice information such as words, patterns of words, phrasing, laughter, smiles, etc.).

In one embodiment, smoke detectors (SDs) detect gases and particles emitted by burning materials, sound a loud tone, and notify the RNSP 125 what it has done. In one embodiment, the tone generator on the SD can also be activated remotely by the RNSP 125 to perform other tasks such as rousing a senior who has passed out or signaling a caregiver that they are engaging in abusive behavior.

Many other sensors can be deployed in the senior's living space such as a CO2 sensor that could detect the air in the room is stuffy. Ambient light sensors can determine the light level. Motion detectors (passive infrared and/or ultrasonic technologies are examples) can determine where people or pets are located throughout the senior's living space. Bluetooth sensors can determine the proximity of devices with Bluetooth transmitters.

A variety of actuators, smart appliances, home robots, smart medical/health devices, and other IOT devices may be included in the home environment as illustrated in FIGS. 1B-1E. As an example, Actuators include devices that can open or close a door with a motor, lock or unlock door locks, rouse a groggy senior with a motor in a chair, raise or lower a recliner to help a senior in or out of a chair, adjust a motorized hospital bed, control a stove, open or close a window, open or close drapes, control a dishwasher, control a clothes washer or dryer. Robotic assistants can cook and serve food, load or empty a dishwasher, a clothes washer, or clothes dryer. Robots can clean the senior's living area, talk to the senior, administer medications, detect intruders, answer the door, open packages, open medicine bottles, give the senior medications on a timely basis, serve as a medical sensor platform for a telemedicine system, etc.

FIG. 1B-1E also illustrates the possibility of integration with third party services to provide a service to the senior or the CG, such as Uber™. Ride services, such as Uber, have internet access to request services and interfaces to provide updates on the status of services. For example, in one embodiment, coordination of a ride of a senior to a senior center or to a doctor may be coordinated by the CG by making voice commands that are listened to by the voice assistant and then used to access the third-party service (e.g., Uber™). As another example, integration with a social network service may be provided, such as permitting voice commands via the voice assistant, to access support calls, online games, or other virtual social activities with a community of other seniors stuck at home.

A variety of different techniques connect wireless sensors and actuators to the SC 110. As previously discussed, wireless sensors and actuators can be directly connected to the SC 110 over a broadband connection. The same functionality can be provided by directly connected sensors and actuators and those that are first connected to an RNSP 125. It's also possible to have a hybrid system in which some sensors are directly connected to the SC 110 and some communicate through an RNSP 125.

In one embodiment, smart appliances are supported. In one embodiment, the Smart fridge (SF) is a refrigerator (e.g., Samsung model RF28M9580SG/AA, 28 cu. ft. Capacity 4-Door Flex™ Refrigerator with Family Hub™ (2017)) that can monitor what it contains, what is put in and taken out, provide a display on the outside of the door, and communicate over the LAN and WAN. The SC 110 monitors the freshness of the food contents in the SF by tracking the dates when they first appeared and their history of refrigeration.

In one embodiment, HR information tracked in the SC 110 includes refrigeration history of medication. The SC 110 automatically identifies medication bottles by recognizing their bar codes with images from the interior cameras and recognizing the amount of medication they contain using computer vision techniques (an example technique determines the level of fullness in a medicine bottle by applying binarization, edge detection, and line fitting with Hough transform). The display on the door of the SF is an actuator for the SC 110. The display shows alerts when the medication is getting low, when it's time to take a medication, when a medication the EMR says should be in the refrigerator is not present.

Other examples of smart devices in which medication may be stored include smart medicine cabinets and smart pill/medicine boxes. If the senior's medication is stored in these types of units, the SC 110 can receive raw data or HR event data indicative of medication usage.

The Electronic Medical Records (EMR) system contains the senior's health history, the record of their interactions with their physicians, and instructions about how they should be cared for and the medications they should receive (including dosage and timing of administration). Care instructions and medication information is transmitted from the EMR to the SC. The SC 110 parses this data, determines what's relevant for the various CGs assigned to each senior, and sends appropriate instructions to the CGs' personal devices. For example, "4:12 PM to Margaret from EMR: senior Pam should receive 10 mg Amlodipine at 4:30 PM."

In one embodiment, the system database records every interaction in the system as well as the scheduling of CGs. Raw IOT sensor data as well as events detected in that data are stored in the system database. This provides a comprehensive history of the IOT data produced by every senior, family member, and CG whose agency uses SC 110.

In one embodiment, the On-site server (OSS) 130 is a computer that provides wired or wireless connections to sensors and actuators similar to those connected to the RNSP. In one embodiment, the OSS 130 is preferably in the senior's living area. Wireless sensors and actuators are connected to the OSS 130 by Wi-Fi or Bluetooth. Wired sensors are connected by serial lines or USB.

The OSS 130 provides an easy means of interfacing with a variety of off-the-shelf devices that might not necessarily have wireless communications. For example, a variety of medical devices are available with Bluetooth and USB connectivity including blood pressure cuffs, otoscopes, thermometers, blood sugar testers, etc. The data from the medical devices is converted to HR data in a format that identifies the senior, the device, the time, and the result of the sensor. For example, "senior Pam, 10:34 PM, Mar. 1, 2018, blood pressure 160/98."

In one embodiment, the OSS 130 also has a display, microphone, audio input and output that communicate with the senior and the CG. It receives and outputs messages for the senior and the CG from the SC 110, for example, "4:35 AM to Margaret: give senior Pam 10 mg angina medication immediately." This can be accompanied by the transmission of a tone to the speaker, flashing of the display, buzzing the smoke detector, and other means of attracting the attention of the senior and the CG.

In one embodiment, activity devices (ADs) can also be connected to the OSS 130 or directly connected to the SC 110 through a specialized controller. ADs are peripherals such as virtual or augmented reality goggles (e.g. Oculus Rift), Wii game controllers, Microsoft Xbox or Kinect game controllers, or medical-related devices such as motorized wheelchairs or electronically augmented walkers. ADs transmit information about their usage to the SC 110 through the OSS 130. For example, "senior Pam practiced the Balance Game from 10:07 AM to 10:30 AM on Mar. 2, 2018." ADs also receive instructions from the SC 110 through the OSS 130. For example, a game controller can increase the rate of the exercises performed by the senior based on instructions received from a physician in the EMR system. Such an instruction might be "Dr. Patty prescribes 20 minutes twice per day of moderate upper body conditioning for senior Pam."

In one embodiment, the system may identify a senior as being lonely (or likely to be lonely) and initiate a mode of operation in which the system activates a social interaction between the senior and another person or senior in another location. Loneliness has adverse health and mortality impacts equivalent to obesity and smoking. Consequently, initiating social interactions between the seniors and people in other locations can provide many health benefits.

As an example, the system may proactively offer a social interaction or social game to be played with another senior or person. In one embodiment, an "opt-in" may be provided for the system to serve as a social network between seniors, caregivers, and other people who may be interested (e.g., a philanthropic organization, senior citizen center in another location, etc.).

In one embodiment the system may use one or more factors to identify that a senior is lonely or likely to be lonely. As one example, in one embodiment a physician or a psychiatrist indicates that the senior is likely to be lonely. As previously discussed, the VA may be used to detect signs of loneliness and an HR event may include detecting factors associated with loneliness. Feedback from the senior, family members, or caregivers may also be analyzed for signs of potential loneliness (e.g., feedback from family members, "Mom seemed very lonely when I visited on Saturday. It is the anniversary of Dad's passing a year ago.").

In one embodiment, the system suggests additional care steps for the senior based on environmental data. This may include, for example, monitoring weather reports (e.g., from the Internet) or using IOT devices, such as a thermostat, to actively sample temperature or other environmental conditions. For example, during a heat wave, the system could auto-suggest that the senior consume more fluids. The auto-suggestions could, for example, be based on general health considerations for seniors. However, more generally, in some situations a physician could suggest changes to the senior's care plan based on environmental conditions (e.g., for a senior with health problems, the physician's selection of the care plan for the senior could include instructions for adapting the senior's exercise plan in the event of high temperatures or a smog alert).

In one embodiment, the senior's laptop can perform most of the same functions as the OSS 130 while still retaining the full functionality of a laptop. This is done by a laptop application (LA) that runs in the background and interfaces simultaneously with the sensors, actuators, medical devices, and activity devices as well as the SC. The LA also monitors the senior's use of the laptop, including the times when it's used, the applications utilized, and characteristics of the usage. Usage characteristics include the rate and accuracy of typing (accuracy measured by amount of backspacing (for example, several research studies and articles such as the article in New Scientist on Aug. 19, 2009 entitled "Keyboard style could give early warning of dementia")), rate of breathing and words murmured, and attention of the senior to the screen as measured by eye movements using the video camera in the laptop's screen (several research studies have indicated that eye movements may be sensitive to dementia and that changes to eye movements may be used to identify cognitive decline, such as the article: Eye Movements in Alzheimer's Disease, http://www.ncbi.nlm.nih.gov/pmc/articles/PMC5332166). Similarly, some research studies indicated that changes in the way a person uses written or spoken language may provide an early warning sign for the progression of dementia.

In one embodiment, HR events are detected in the usage characteristics of the senior's laptop on a per-session basis before they're transmitted to the SC 110. For example, "Senior Pam used laptop from 10:04 AM to 12:35 PM on Mar. 5, 2018. Typed for 0.5 hours, read text for 0.5 hours, daydreamed for 1.3 hours. On Facebook for 1.8 hours. Instagram 0.2 hours. Chatted with 15 family members and 3 bridge partners. Read 12 emails. Sent 5 emails. Email correspondents include 2 family members, 13 bridge partners, and 2 strangers. Recorded 23 bursts of typing. 45 breaths per minute. Average efficiency 0.52. Recognized two curse words and 12 praise words. Saccade rate per minute=0.45. Average saccade distance=10.0 cm."

Figure 1C:
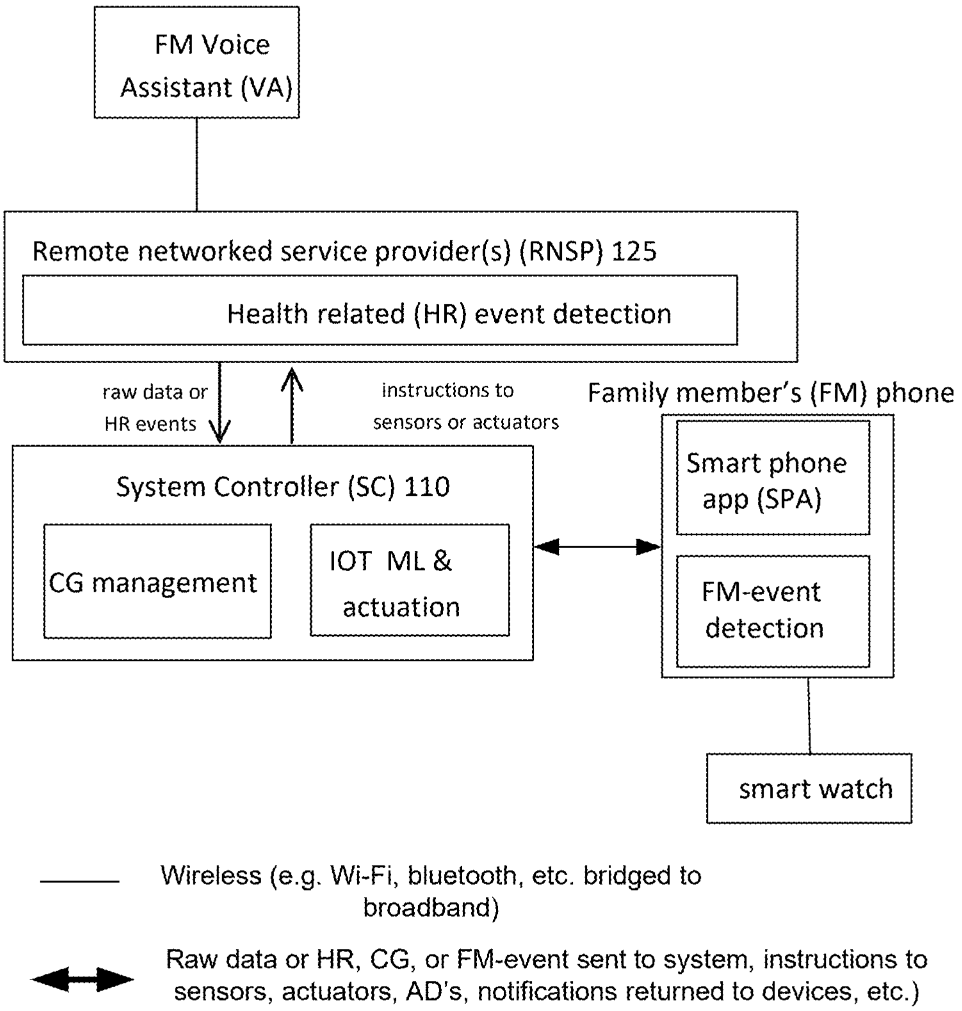
Figure 1D:
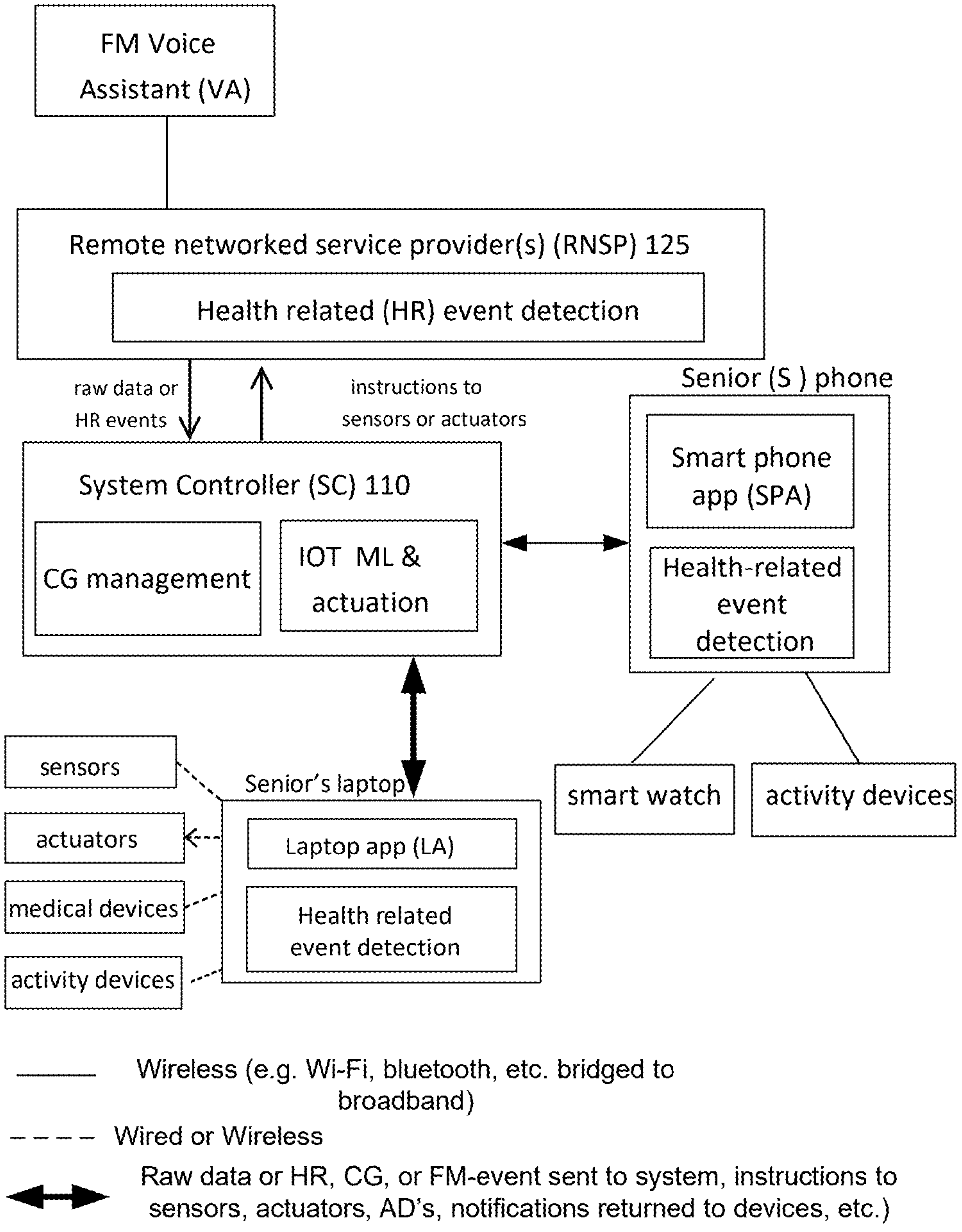

Referring to FIG. 1D, in one embodiment, the senior's phone includes a smart phone application (SPA) specialized for the senior that monitors the senior's usage of the phone and its applications and detects HR events in its sensor data. The SPA may utilize any of the sensors of the phone. As examples, the HR events in the sensor data may include step counts, locations visited (using combination of GPS and indoor location technologies), and number of stairs climbed. The SPA also captures data from the microphone and video cameras all the time and creates a virtual VA on the phone that performs the same functions as a stand-alone VA but without the separate device.

In one embodiment, the SPA uses the camera of the phone to perform many of the functions of the stand-alone cameras connected to the RNSP 125. For example, the senior can point the phone's camera at a CG while the CG is preparing dinner. The SPA also enables notifications on the senior's phone so that it can be used as an actuator. For example, if the SC 110 needs to signal the senior to wake up and take some medicine, it can ring the phone, flash the display, and make it vibrate furiously, even overriding constraints on notifications that might have been enabled by the senior.

In one embodiment, the SPA monitors the senior's usage of other applications on the phone and reports relevant HR events to the SC 110. HR events are aggregated on a per-session basis before they're transmitted to the SC 110. For example, "Senior Pam used phone from 8:24 AM to 9:35 PM on Mar. 5, 2018. Typed 112 characters in 0.2 hours, read text for 0.5 hours, daydreamed for 0.4 hours. On Facebook for 0.8 hours. Instagram 0.2 hours. Chatted with 15 family members and 3 bridge partners. Friended 4 new people. argued (by text or Messenger message) with 3 people. Read 12 emails. Sent 5 emails. Typed 5 naughty words, 12 positive words. Email correspondents include 2 family members, 13 bridge partners, and 2 strangers. Recorded 23 bursts of typing. 45 breaths per minute. Average efficiency 0.52. Recognized two curse words and 12 praise words. Saccade rate per minute=0.45. Average saccade distance=10.0 cm. Time steady on flat surface=23 minutes. Time walking=5.6 minutes.

In one embodiment, the SPA also interfaces the phone with the senior's smart watch (SW). The SPA can instruct the SW to take health readings (e.g., heart rate, blood pressure, blood glucose) whenever necessary. The advantage of the SW over stand-alone medical devices is that the SW is always in contact with the senior's skin and can take health readings whether the senior is awake or not. The SW is also a display for the SC 110. It can receive alerts and get the senior's attention by buzzing the watch whenever necessary. The SW is a terminal in a two-way conversation between the senior, the caregiver, family members, and the physician and other medical professionals. When the SC 110 receives a request from a family member (or anyone else with the appropriate access permission) to talk with the senior, it opens a two-way video chat connection between the two of them. The content of the conversation, video images of the participants and their locations are recorded and filtered for HR content.

In one embodiment, the SPA also interfaces with ADs, preferably those with wireless connectivity. Control and data produced by these ADs can be shared with a SPA on a CG's phone so that the CG can monitor the performance of the senior and help them improve their utilization of the ADs when needed. For example, both the senior and the CG can receive instructions to perform that Balance Game. The senior can be doing it while the CG is monitoring the senior's performance. If the senior fails to understand what he's supposed to be doing, as automatically detected by the SPA, illustrated instructions are sent to the CG's SPA that are relayed in real-time to the senior.

Referring to FIG. 1D, in one embodiment, the SPA on the CG's phone monitors what the CG does and records CG-related events. Arrival (clock-in) and departure (clock-out) at the senior's location are automatically determined by a combination of GPS and (optionally) indoor location technologies. Audio, video, step counts, barometric pressure, accelerometer readings, and other sensor data are all automatically gathered by the SPA while the CG is on-site with the senior and off-site. Application and phone usage are recorded all the time, but especially when the CG is on-site with the senior. Aggregated information is reported at the end of each shift. For example, "Caregiver Margaret arrived at patient Pam's home at 8:00 AM and departed at 5:00 PM. Margaret walked 5466 steps, climbed 127 stairs, lifted 44 pounds. Margaret checked future shifts with the SPA for 12 minutes. She used Facebook for 3 hours 47 minutes, watched TV for 2 hours 12 minutes, talked with patient Pam for 8 minutes." Off-site HR events include a record of web sites related to home care, medical issues, and home care agencies other than those that currently employ the CG.

In some embodiments, the CG may also have a SW accessible by the SPA of the CG's smartphone. A CG's smart watch permits health readings of the CG (e.g., heart rate). In some embodiments, the CG's SW is also a display for communication of alerts or other information from the SC 110. In some embodiments, the SPA of the CG's phone can access the same AD as the senior.

Referring to FIG. 1C, in one embodiment, the SPA on the family member's (FM's) phone helps the FM monitor the condition of the senior, their activities, and the activities of the CGs assigned to the senior. FM related event detection may include monitoring the condition of the senior, their activities and the activities of the CG assigned to the senior. The SPA can open a communication channel with the CG or the senior whenever necessary. In some embodiments, the SPA on the FM's phone can access the FM's SW to provide alerts or warnings on the FM SW.

In one embodiment, the SPA on the FM's phone sends a request to the SC when a family member wants to talk with the senior in order to open a two-way video chat connection between the two of them. In one embodiment, the content of the conversation, video images of the participants and their locations are recorded and filtered for HR event content. In some embodiments, voice analysis is performed when a FM has a conversation with the senior. For example, voice stress may be monitored or other attributes of the conversation.

Figure 1E:
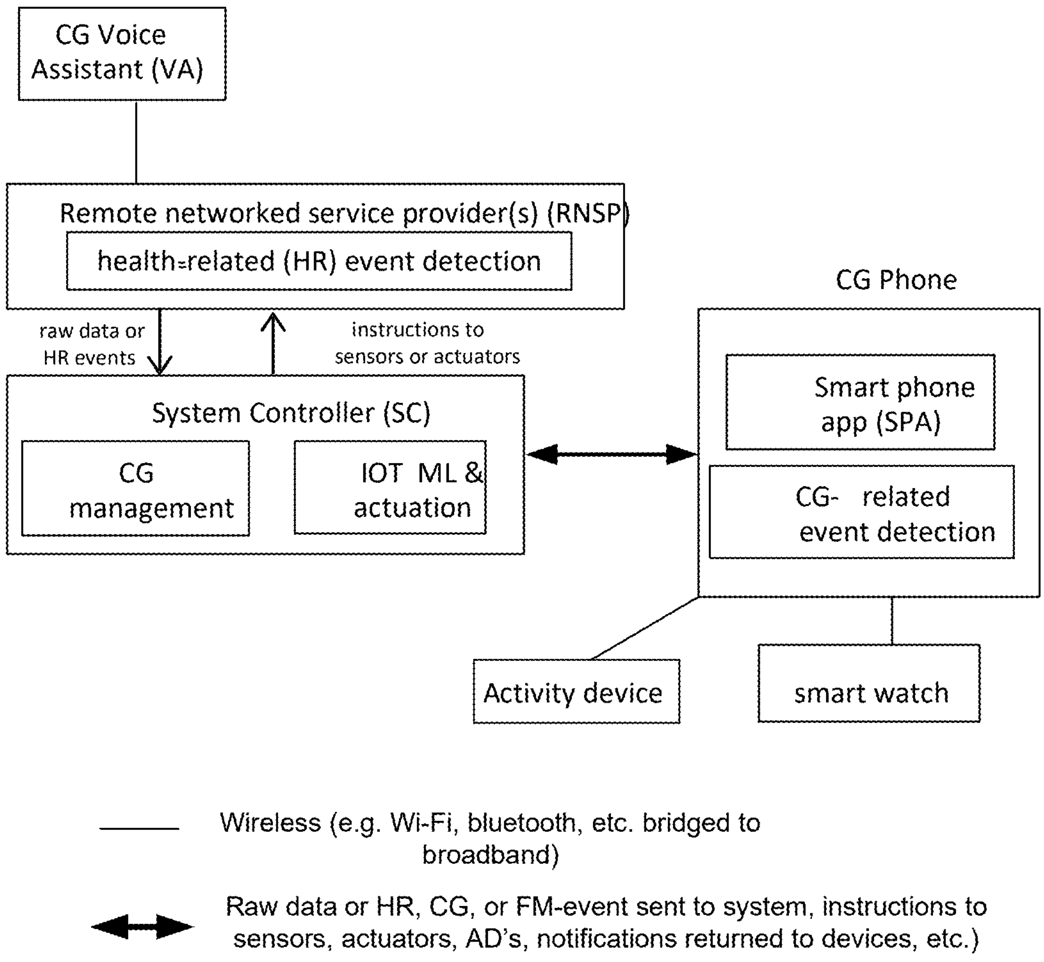

As illustrated in FIGS. 1C and 1E, in some embodiments voice assistants are provided for the FM and the CG, along with RNSPs to provide raw data or HR events to the SC 110 and receive instructions from the SC 110. In some embodiments, different RNSPs are used for the senior and the FM or the CG.

Figure 1F:
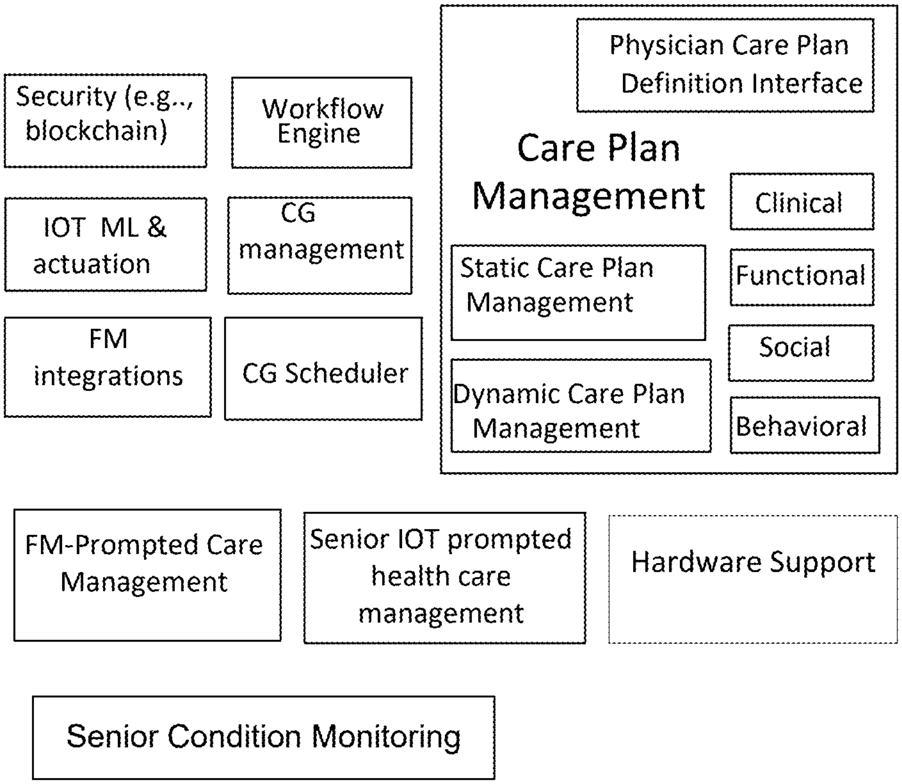

FIG. 1F illustrates another example of a SC 110. In one embodiment, the SC 110 includes a security module to implement a security protocol or security scheme to protect confidential health information (e.g., blockchain). In some embodiments, support is provided for family members to care for seniors during days or time slots that the CG is not taking care of the senior. A FM prompted care management module may provide prompts for a family member to take care of a senior according to the daily care plan. As examples, the family member may be given prompts on the senior's medications to take and diet restrictions. (A FM interaction module may be provided to support general communications and interactions with FMs). In some embodiments, a senior IOT prompted self-care management module is provided. For example, when the senior is alone, the VA may be trained to ask questions or provide prompts to the senior, such as "How are you feeling this morning Alice?" Some of the voice questions and prompts may be to assess the physical or emotional state of the seniors. Additionally, the voice prompts may include reminders (e.g., "Alice remember to eat your dinner") or provide mental or social stimulation ("Alice, would you like me to schedule a phone call today with your friend Joan?").

In one embodiment, the SC 110 has a care plan for each senior. The care plan may have different components, such as clinical, functional, social, and behavioral components. The care plan may have a fixed portion for each day (e.g., activities and actions to be performed every day, such as medications the senior is to take each day) but more generally may also have dynamic aspects (e.g., selecting actions based on HR events, such as providing additional social stimulation or activities if the HR events indicate the senior may be lonely or depressed).

The HR events may include a variety of different events encountered by seniors. The home sensors may be trained by ML to detect a variety of HR events important for senior health care. For example, fall detection is important for seniors generally, although it may be particularly important for a senior with advanced osteoporosis who has fragile bones. Getting out of bed (and moving) is generally important for seniors but may be particularly important for some health conditions.

In one embodiment a workflow engine is included in the SC 110 for CG management. The CG management module may also have an associated scheduler to schedule CGs.

The workflow engine implements the care plan and determines tasks, events, and rules for the CG. This may include defining shift details for the CG and task details for the CG during a shift. For example, a particular shift for the CG may have a sequence of tasks to be performed for the senior, such as a medication task, a memory improvement task, and a meal preparation task as examples. Each task may have a set of detailed instructions and action items such as report items. For example, the medication task may specify the exact medications for the senior. In one embodiment, the workflow also defines IOT augmentation attributes to implement at least one task, event, or rule for the CG.

In one embodiment, the SC 110 creates an audit trail of information stored in the system database. This may include, for example, information to verify that CGs have attended to the senior (e.g., clock in, clock out and verify tasks in care plan performed, to create a record that consistent quality care has been provided, or to create records for training of CGs (e.g., provide feedback to the CG that they are using proper lifting/handling techniques for the safety of the senior and the CG), etc.

As illustrated in FIG. 1F, in one embodiment a physician care plan definition interface module is provided for a physician to select details of the care plan. In one embodiment, a physician performs an assessment of a senior and then makes a selection of choices for the in-home care plan for the senior. As examples, this may include the number of days per week that a CG attends the senior. The physician selects the medications for the senior, may select the senior's recommended diet, and provide a recommended physical exercise plan. The care plan may also include recommendations on activities the CG is to perform with the senior, such as memory games as one example.

In one embodiment, the physician also has an option in designing a care plan to select augmented IOT home care. In one embodiment, the physician is provided an option to select specific IOT devices and tasks that are to be used in the care plan. In some embodiments, the physician is also provided with options for the IOT devices and smart devices in the home to provide various forms of preventive care, including monitoring for signs of a progression of a disease or an increased risk of a negative health outcome.

As an example, for a senior with advanced osteoporosis and brittle bones, a physician might select a fall detector as an IOT device, use smart devices in the home (such as a smart fridge) to confirm that the senior is consuming calcium rich foods, and instruct the CG to perform tasks for the senior consistent with improving the senior's bone density and reducing the chance of the senior falling. In this example of a senior with brittle bones, the physician may also be provided with options for related preventive care, such as having video cameras in the home monitor the senior's gait and posture for changes to the senior's posture or gait that might signal an increased risk of a catastrophic fall.

In one embodiment, a physician may select, as part of the care plan, smart medical and health devices to be used on the senior. For example, a physician may be provided with an option to select that the CG utilize a smart medical or health device in the senior's home to perform a specific test or procedure according to a schedule. As another example, a physician concerned about the loneliness of a senior may be provided with an option to design the care plan to utilize voice assistants and social network services to provide the senior with voice access to connect with other seniors for conversation or games.

In some embodiments, a physician may be provided with options for reporting triggers to schedule preventive checkups, medical interventions, or telemedicine consultations. For example, suppose a physician selects, as part of the care plan, that video cameras in the home are to monitor the senior's posture, gait, and movement patterns. Changes to these factors may be indicative of the desirability of a health checkup, medical intervention, or telemedicine consultation, depending on the severity of the change. For example, instead of waiting for a senior to have a catastrophic fall before seeing the doctor, the physician might request an alert if the senior's balance and movement degrades to a point indicative of a statistically increased chance of fall.

In some embodiments, a physician may be provided with options to test changes to the care plan and receive reports as feedback, between physician visits, as to the effectiveness of the change to the care plan. For example, a physician may desire to test a change to the senior's diet, physical training, or other aspects of the care plan. In one embodiment, the physician inputs the care plan and requests data on the effectiveness of a change to the care plan. As examples, the feedback may be at specific time periods; in response to specific conditions; or generated on demand. For example, suppose that the physician requests that the CG do specific strength or mobility physical training exercises with the senior. In one embodiment, the physician is provided with options to specify what type of feedback they are to be provided (e.g., a video from the IOT devices showing the posture, gait, or movement of the senior after a selected number of weeks or months on a new exercise program or processed data showing changes in a physical attribute of the senior, such as a mobility measurement, relative to a baseline). Similarly, in one embodiment, a physician may decide to experiment with changing the senior's medication and request specific feedback (e.g., changes in sleeping patterns and daytime alertness in response to a change in medications).

In some embodiments, the SC 110 provides recommendations, via the user interface, to aid a physician in selecting augmented IOT options and associated CG tasks. In particular, some selections for the physician may be advised as preventive care to minimize long-term patient costs and improve quality of life for the senior in view of statistical data on the long-term outcomes of seniors with comparable medical histories. For example, changes in the baseline data for the senior over time, as measured by the IOT system, may provide an early warning of 1) the onset or progression of some diseases; or 2) information indicative of a general decline in the senior's health that could put them at a greater risk for things such as debilitating falls.

As another example, suppose a senior has a respiratory problem. In this example, the physician may select a care plan in which the in-home sensors and actuators are used to monitor air quality to ensure the senior has sufficient oxygen.

As another example, suppose a senior has a family history of dementia but shows no current signs of dementia. In this example, the physician may select a care plan in which the IOT system is used to monitor for signs of early onset dementia, such as changes to written or spoken use of language.

In some embodiments, a physician may select to be provided general information on potential risk factors indicated by the data trends in the IOT system. For example, a physician might request an analysis of changes to the senior's mental, physical, and emotional health on demand, such as before a scheduled physician visit.

Embodiments of this disclosure thus permit a physician to design a care plan for a senior that includes one or more features of the IOT system. This may further include specific tasks the CG performs with the senior using aspects of the IOT system.

In some embodiments, the physician may also select attributes of a self-care plan for the senior that use elements of the IOT system. For example, in one embodiment a physician may select that the IOT system provide social stimulation to the senior, such as through the use of voice prompts, playing games with the senior, and facilitating social connections of the senior to other seniors. As another example, in one embodiment, the physician may select a self-care plan in which the SC provides verbal reminders to the senior via the voice assistant (e.g., "Good morning Alice. Remember to take your medication this morning. One blue pill, one green pill, and the vitamin capsule. You have a virtual senior bridge game at noon that I have scheduled and I will connect you when the game starts. Let me know if you want me to schedule a call this morning with your friend Stephanie").

As another example, in some embodiments, the physician may choose that the senior be provided guidance or reminders about their care plan. For example, a physician may be provided with an option that the senior is reminded about aspects of their care plan on days when the CG is not there (e.g., "Good morning Alice. As a reminder your self-care plan for this morning includes walking at least five minutes and taking the medications in the smart pill box").

In some embodiments, a physician may be provided recommendations based on demographic information for the senior. For example, some home residence locations are "food deserts" in that there are few local selections nearby to purchase healthy foods such as few places to buy fresh vegetables. Other home residence locations are located in areas in which there are few (or even no) seniors in the neighborhood such that the senior may have a higher risk than average of social isolation. In one embodiment, the physician is provided at least one recommendation for the care plan of the senior based on demographic data of the senior. For example, if the senior lives in a "food desert" with no nearby seniors the SC could recommend closely monitoring the senior's food consumption (e.g., via a smart fridge) and linking the senior to other seniors via social network services.

In some embodiments, information on a FM who regularly visits the senior may be available to the physician or already stored in the SC 110. In one embodiment, the physician is provided with an option for the SC 110 to provide guidance (e.g., prompts in text or voice form) to a visiting FM so they know what the care plan is for the senior when they visit and the CG is not there and how to implement it. (e.g., "Good morning Thomas. Your mother Alice is still asleep. When she wakes up please make sure she takes her pills from the smart pill box and try to walk with her for five minutes. She fell a week ago, so please watch her carefully so she doesn't fall.")

In some embodiments, the physician may be provided options for adapting the care plan based on short-term changes in the physical or emotional health of the senior. For example, the IOT system may collect information on the senior's sleep patterns, bathroom patterns, activity levels, and behavior. In some embodiments, a physician is provided options to specify more or less social activities for the senior based on their current mental, physical, or emotional health. For example, if a senior is having a "bad day" the care plan might be adapted to provide more social stimulation (if that would be helpful for the senior's personality type) or less social stimulation (if that would be helpful for the senior's personality type). Other options could be provided for varying other aspects of the senior's daily care plan based on recent HR events detected by the IOT system (e.g., reducing the senior's caffeine intake or making sure that bedroom lights are dimmed at night if they have not been sleeping well).

In one embodiment, a physician is provided with options to select a third-party service provider integration. For example, some seniors may have difficulty getting to their physician. An option could be provided for a third-party service provider (e.g., Uber) to provide a ride with the CG to the physician's office.

In some embodiments, the SC 110 makes suggestions to the physician of IOT devices, home robots, and smart appliances that may improve the quality of the senior's care or reduce long-term health care costs for the senior. For example, the recommendations may be based on a database of seniors having comparable medical histories and using different aspects of the IOT system architecture.

In some embodiments, the physician is provided an option to perform food interventions. There have been some experimental studies indicating that for some medical conditions rigid control of food intake can reduce or eliminate the need for certain medications. One such example is the "food Farmacy" program in Pennsylvania that prescribes foods such as leafy green vegetables to reduce inflammation. However, in practice it is often hard to implement such programs, particularly if a senior lives in a food desert in which their local food choices are mainly junk food outlets.

In one embodiment, a physician may select a food pharmacy option for the senior and requests support from the IOT system, such as using a third-party service provider integration to have specific foods delivered to the senior's home, use of the smart fridge or other home IOT devices to check that the senior consistently eats according to their food pharmacy guidelines, etc. Other sources of information could also be checked for cheating, such as using the in-home cameras to detect signs of fast-food bags. (If access to the senior's credit card information is available, that could also be checked for restaurant choices).

As another example, in some embodiments, a physician may be provided with an option for the IOT devices to perform a home safety assessment. For example, for a senior with a high risk of falling, the in-home video cameras may be used to determine whether there is a clear path for the senior to walk. Additionally, CGs may be assigned tasks to remove items from the floor that are potential hazards for the senior to trip over. (e.g., the CG may be given a task "remove item detected on carpet between senior's bed and the bathroom").

Figure 1G:
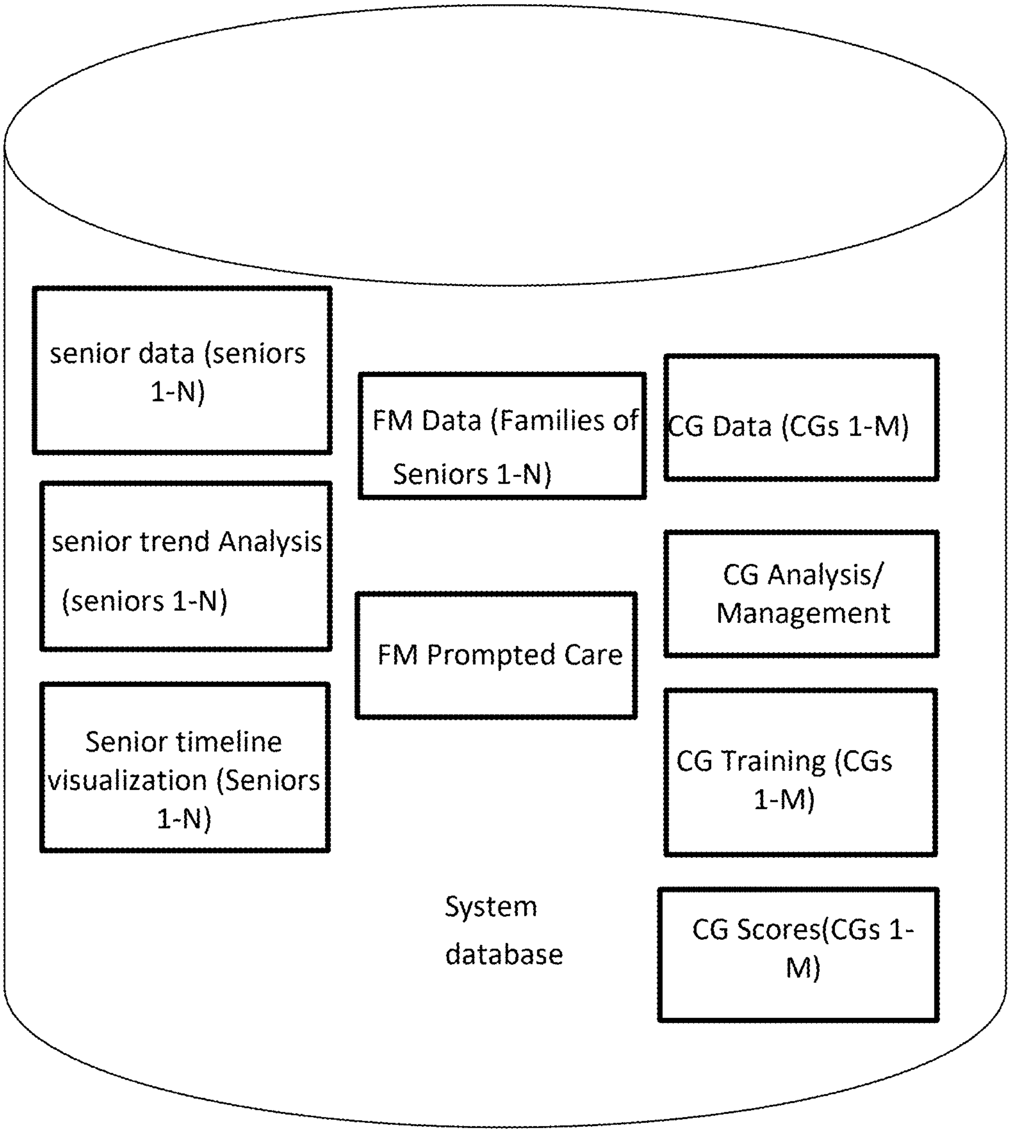

As illustrated in FIG. 1G, in one embodiment the system database collects IOT data for each senior of a group of seniors 1-N serviced by the system. This data is analyzed by a software program to generate trend data for each senior. Additionally, in one embodiment the trend data of the group of seniors is analyzed by a software program to identify clusters of seniors having similar trends in health and IOT data. In one embodiment the IOT data for seniors is collected and processed by a software program to create information for visualization of aspects of the senior's life.

In one embodiment the IOT data is collected for each CG (e.g., for CGs 1 to M) and stored to permit CG scores to be calculated by a software program according to a set of criteria. For example, CG time-in, time-out and other data related to the quality of care provided by the CG may be used to generate a CG score, grade, or ranking of each CG.

In one embodiment the IOT data is collected and processed to generate data to aid in managing CGs. For example, the IOT data may be analyzed to determine whether a CG is an attrition risk (i.e., is likely to leave their job), provide recommendations for additional training for the CG (e.g., stress management training for the CG in response to detecting stress in the CG's voice or an argument with a senior), or an alert (e.g., an alert during a session with a senior, such as a warning if an argument with a senior is getting out of control).

In one embodiment, FM data is collected for the families of the seniors, including any interactions in which family members provided prompted care. A software program supports FM prompted care.

Exemplary IOT Machine Learning Module

Figure 2:
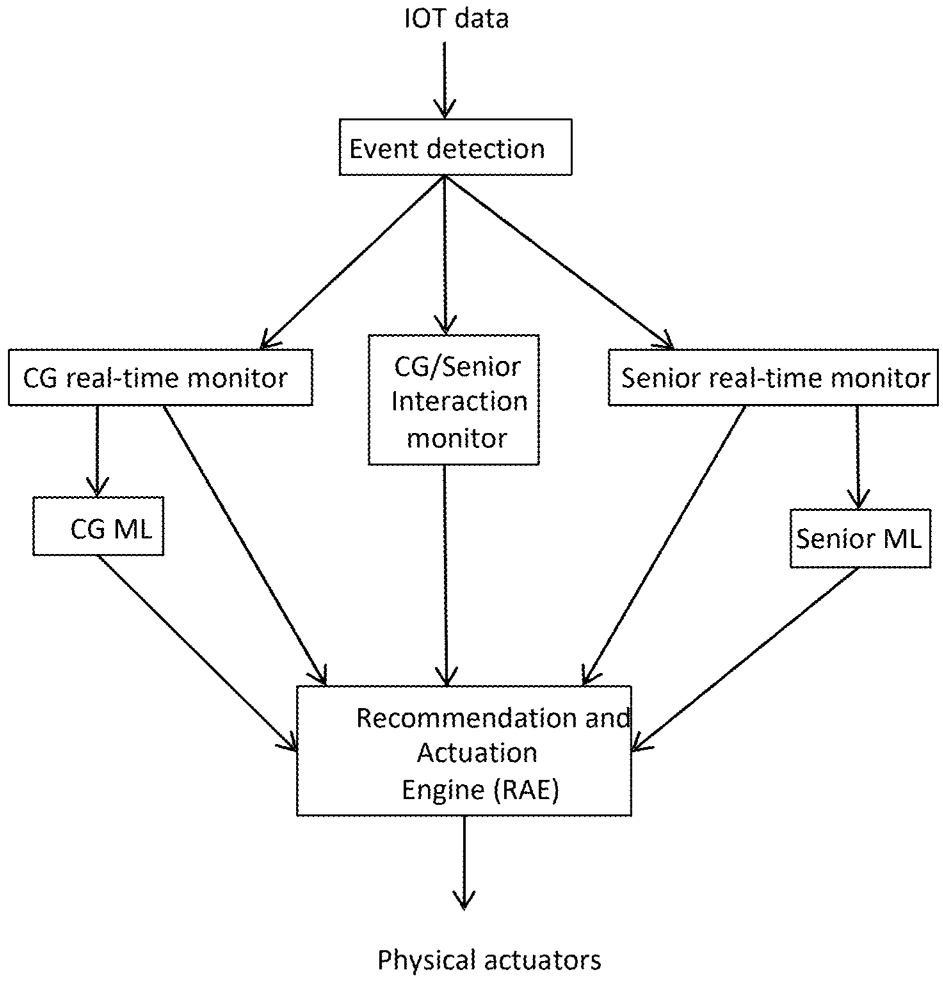
FIG. 2 illustrates an embodiment of IOT machine learning and actuation in accordance with an embodiment.

FIG. 2 shows an embodiment of the IOT machine learning and actuation module. In one embodiment, the ML of the IOT machine learning and actuation module may be based on learning from example inputs and their desired outputs. That is, for a sensor, or combination of sensors, events are determined from IOT device data.

In one embodiment, if the IOT data is in "raw" form and events within it have not been identified, events are identified that are relevant to the CG and the senior. Table 1 lists an example of sensors used, the data they produce, and the events detected in that data.

TABLE 1

Sensors, the data they produce, and events we identify in the data.

| Sensor | Data | Events |
|---|---|---|
| Video | video frames | Entrance and exit of people into senior's living space<br>Identification of people<br>Locations of people<br>Activities people are doing<br>Features of people: gait, walking velocity, head position, eye state (open, closed, drowsy, etc.) from cameras on laptop, TV, wheelchair, etc.<br>Placement of furniture<br>Items on top of furniture |
| Thermostat and HVAC controls | Settings, current temp. | Current ambient temp., temp. history, if recorded |
| Voice asst. and microphones | Audio data | Speaker identification<br>Voice stress analysis<br>Location of speakers<br>Text in speech<br>Sound identification (snoring, water running, TV program ID, radio broadcast ID, volume of TV and radio, walking quality (detect shuffling feet)) |
| Smoke and CO detectors | Alert condition and/or gas levels | Alerts indicate fire or high CO<br>Gases below alert levels indicate food cooked with heat by frying or baking |
| Olfactory | Odors | Food, person, animal identification, fresh paint, etc. |
| CO2 | CO2 concentration | Concentration indicates air "stuffiness" |
| Ambient light | Light level | Room lights turned on/off, windows opened/closed, outside lights turned on/off |
| Motion detectors (PIR, ultrasonic, LIDAR) | Motion events, direction, distance | Movement of people and objects w/in space |

TABLE 1-continued

Sensors, the data they produce, and events we identify in the data.

| Sensor | Data | Events |
|---|---|---|
| Wireless transceivers (Wi-Fi, Bluetooth, etc.) fixed position or mobile (in phones, watch, etc.) | Signal strength and device identification | Proximity and identification of devices |

Moreover, HR events may be defined based on a combination of events. For example, HR events may be detected based on the data from two or more sensors. As one example, the HR event may be based on sensor data for the CG and for the senior. As an example, a potential risk to a senior falling may be identified based on the CG being in another room than the senior, the senior moving with an unsteady gait, and a low light level in the room the senior is in. That is, the combined information from two or more sensors may be analyzed to detect HR events.

In one embodiment, a sequence of video frames from the video cameras in a senior's living space (including cameras on the senior's laptop, phone, TV, wheelchair, and other devices), we identify when people enter and leave, who they are, where they are presently located, what they are doing, how they look (their gait, head position, eye state (open, closed, drowsy)). We also identify the furniture items in the senior's living space (bed, chairs, tables, etc.) and the items on top of those furniture items (newspapers, remote controls, medicine bottles). This could be used, for example, to identify where people in the home are located, including the senior and the CG. An example of a video event is: "9:05 AM senior Pam is sleeping in chair in front of TV." As another example of a video event is: "9:05 Am senior Pam is sleeping in chair in front of TV and caregiver Bill in the kitchen talking on his phone."

The analysis may also include an analysis of risk factors such as identifying risk factors for the senior, such as objects on the floor that the senior might trip over.

In one embodiment, thermostat and HVAC controls return their present settings as well as the ambient temperature and history of ambient temperature readings if that data is stored on the device. From this we detect the pattern of recent temperature changes and the utilization of HVAC system components.

In one embodiment, voice assistants and microphones in the senior's living space provide audio data from which we identify who is speaking, the stress levels in their voices, the location of speakers by triangulation of inputs from multiple microphones on more than one device or on a single device. What is being said is also recognized in real-time and commands within that speech are detected. For example, "Tell my doctor that I'm having a migraine every morning." Sounds are also identified such as snoring, running water, and walking quality (shoes shuffling over the floor). In one embodiment, an identification is performed of the TV and radio programs being watched and listened to. In one embodiment, this data is reported to the CG as potential conversational material (e.g., discuss characters in soap operas). Changes in TV and radio habits are also identified as indicators of changes in the senior's health condition and are reported to the health care provider.

In one embodiment, smoke and carbon monoxide detectors produce alerts when dangerous levels of particulate matter or gas are detected. Levels of particulates and gases below dangerous levels are also reported. These are important in monitoring the health of the senior's living environment since even elevated levels of these pollutants can be harmful to someone with a weakened immune system. We also monitor and report these levels to the senior's physician as necessary. CGs are warned when these pollutants rise so they can mitigate their effects by increasing the amount of fresh air in the living space, for example.

Carbon dioxide detectors report the concentration of $CO_2$ in the air and are an important part of monitoring the healthfulness of the senior's living environment. For example, the 2016 OHSA guidelines for carbon dioxide detection and indoor air quality control state that: "Moderate to high levels of carbon dioxide can cause headaches and fatigue, and higher concentrations can produce nausea, dizziness, and vomiting. Loss of consciousness can occur at extremely high concentrations. To prevent or reduce high concentrations of carbon dioxide in a building or room, fresh air should be supplied to the area." In one embodiment, the system monitors $CO_2$ levels so we can apply actuators (e.g., notify CG and tell them to open windows until the $CO_2$ levels drops sufficiently) that prevent problems from happening. We also notify the senior's physician about the ambient $CO_2$ level in the senior's living area.

In one embodiment, ambient light detectors provide information (measured in lumens) about the light level in the senior's living space. They determine when room lights are turned on/off, when windows or drapes are open or closed, and when outside lights are turned off and on. This information is useful in monitoring ambient light in the senior's living space. It's well known that low average light levels are associated with higher rates of depression than in the population at large. Conversely, high light levels at inappropriate times (i.e., during nighttime bedtime hours) can also have a detrimental impact on sleep patterns. In one embodiment, this problem is mitigated by having bedroom and other room lights that are remotely controlled by the system controller. We turn up lights nearby seniors when they should be awake and active. We also notify the CG and family members as appropriate so they can intervene if needed.

In one embodiment, motion detectors use a variety of technologies (passive infrared, ultrasonic, combination) to determine when people and objects move within the senior's living area. This information is tracked so the system can accurately determine when people or pets move around. We also use LIDAR (light detection and ranging) technology to track the movement and velocity of people and objects. Both motion detectors and LIDAR have the advantage that they work in the dark. We use the data they produce to track changes in the patterns of movement within a senior's living space over time. As seniors age, they slow down and visit fewer rooms per hour at lower speeds than they previously did. We use motion data to detect changes in seniors' health over time as well as the activity of the CG.

In one embodiment, wireless (Wi-Fi, Bluetooth, etc.) transceivers, both in fixed positions throughout a senior's living area as well as on their laptop, cell phone, smart watch, and other devices, report signal strength and identification of other nearby wireless devices. In one embodiment, this data is used to locate and identify devices in the senior's living space and share that information with the senior, CG, and family members. This helps locate lost devices and, when shared across a population of seniors, locate objects left by seniors or CGs in another senior's living area.

In one embodiment, the real-time monitors identify events that require an immediate response and send instructions to the recommendation and actuation engine that implement the response. For example, if a CG has fallen asleep (detected by video event (head slumped over), audio events occur (heavy, steady breathing from the CG's phone and the voice assistant) and motion events are detected (CG's smart watch hasn't moved in 20 minutes)) and it's time to administer medication, the buzzer on the CG's smart watch is activated, the CG's phone rings, and the motor in chair the CG is sitting in is activated. This is accompanied by a message played on the voice assistant that tells the CG what to do. Monitoring continues and the actuations escalate until the medication is administered.

In one embodiment, the real-time monitors are implemented with a hierarchical rule-based system. Knowledge of the senior's environment is encoded when the system is installed and updated as needed. This includes the layout of the senior's living space and the locations of major items within that space including the senior's bed, easy chair, bathroom, kitchen, and couch. Locations of sensors with respect to those items are also recorded, e.g., there is a voice assistant next to the right side of the couch. The locations of actuators with respect to each location are also stored. For example, the couch contains a variable speed motorized shaking system that can be used to awaken people. The buzzer in the smoke detector is three feet in front of the couch. The TV is in front of the couch. The OSS is five feet to the left of the couch.

In one embodiment, action strategies are identified for each situation the recommendation and actuation engine might be applied to. Each situation is described by a list of the actions that are executed when the action strategy is executed. An example action strategy follows:

Action Strategy: Rouse the Caregiver
- Identify location of CG
- Identify actuators that can rouse the CG using the knowledge encoded at installation
- Escalation sequence:
  1. shake furniture at level 3, vibrate phone, ring phone, play message of voice assistant
  2. shake furniture at level 7, turn on buzzer in smoke detector for 30 seconds
  3. shake furniture at level 10, turn on emergency alert system tone in TV
  4. continue applying #3 and call CG's manager
  5. if CG's manager does not respond, call 911. The CG must be in distress. The senior's health is at risk.
- Sensors that can monitor the response of the CG=video cameras with view of the CG's location and nearby voice assistants
- Criteria for successful awakening=CG stands up and remains standing for at least 30 seconds
- Repeat
- Apply actuators in their defined escalation sequence
- Until Sensors that monitor response of the CG show that she has been successfully awoken Monitor strategies are described by a list of the actions that are executed when the monitor strategy is invoked. An example monitor strategy follows:

Monitor Strategy: Ensure Medication Administration
- Identify location of the senior
- Identify sensors that can monitor administration of medication (video cameras, voice assistants, CG's phone, CG's watch, senior's phone, CG's watch)
- Listen to events from each sensor until at least N (variable setting) agree that the senior consumed their medication. The more sensors that indicate medication was successfully administered, the more accurate the result.

Rules are comprised of conditions and actions. An action can be creation of new knowledge such as a statement of where the CG is located or they can be instructions that apply action strategies or monitor strategies. The conditions in each rule are matched to the incoming events and if they apply, the associated action is executed. For example:

If (CG is sitting on couch in video) Then CG_location="couch"

If (CG's watch is motionless for more than 20 minutes) Then CG is not moving

If (CG head slumped in video) AND (CG breathing heavily in CG phone audio) AND (CG not moving) Then CG is sleeping If (medication due in less than 10 minutes) AND (CG is sleeping)
Then
  Apply Action Strategy (Rouse the Caregiver)

If (medication due in less than 10 minutes) AND (CG is awake)
Then
  Send instructions about medication administration to CG's phone and watch
  Apply Monitor Strategy (Ensure medication administration)

In one embodiment, machine learning (ML) modules receive the time-stamped events that were input to the real-time monitors as well as the results of the knowledge strategies and action strategies they executed. This information is stored in the system database and used to update various machine learning models.

In one embodiment, senior machine learning module leverages the past experiences of vast numbers of seniors and CGs to recommend strategies and actions that help solve problems faced by many people as they age. One example is the recognition of mental state and recommendation of remedial tasks.

IOT Data as a Diagnostic Tool in Predicting Health Trends and Seeking Medical Consultation A senior may have a care plan defined by a doctor in an initial visit and then the care plan adjusted in the next scheduled doctor visit (e.g., once every 6 to 12 months). In one embodiment, the IOT data is collected and used as an aid for doctors to understand health trends for the senior between doctor's visits. For example, IOT data permits the senior's day-to-day compliance with their care plan to be studied. Additionally, in some cases, the IOT data may provide information on the onset or progression of a degenerative disease. This may be useful for doctors to obtain information to more efficiently revise care plans for the senior.

Moreover, this information may be useful to trigger actions to recommend a medical appointment or consultation for the senior. For example, if the senior has an uneven gait and unsteady on their feet, a notification it could be a sign of a variety of problems such as a balance problem, a joint problem, a neuromuscular problem, or a problem with the senior's current medication. As many seniors are seriously injured in falls, taking proactive steps to have the senior obtain a medication consultation before a fall takes place may improve the quality of the senior's life.

For example, a senior's IOT data could be matched to data for similar seniors, including their medical records, and identify changes, such as a stooped gait, that could benefit from the advice of a medical professional (e.g., occupational therapist) before the problem escalates to the point that the senior falls down and needs an emergency room visit.

As another example, data from smart medical or health devices may also be monitored for signs that a medical consultation may be desired. For example, large changes to body weight and changes to exercise patterns may increase risk factors for certain diseases, such as diabetes or some heart conditions.

IOT Data as a Diagnostic Tool in Predicting Dementia

In one embodiment, an assessment is made of the mental state and cognitive functioning of seniors periodically by administration of various screening tools such as the Mini Mental State Exam (MMSE), the Standardized Mini Mental State Exam, the Abbreviated Mental Test, etc. The results of these tests are stored in the system database together with the IOT data and events for those seniors and their caregivers. Cognitive charts are stored that distinguish seniors with dementia from seniors whose cognitive functioning is declining "normally" as the result of aging.

In one embodiment a feature vector is created for each month in a senior's life that includes the time series of their IOT data from the previous N months (Nis configurable) as well as the likelihood that they will experience abnormal cognitive decline (attributable to dementia) in the next three, six, and nine months where cognitive functioning (and hence decline) is measured by scores on standardized assessment tools such as the MMSE.

The data for seniors for whom we have MMSE scores are used to train a deep learning model that uses IOT data alone to predict the likelihood a senior will experience abnormal cognitive decline in the next 3, 6, and 9 months. Every day, as more IOT data are accumulated for a senior, it is matched against the stored data using the pre-trained deep learning model and the likelihood of abnormal cognitive decline is updated. If an unusual change is detected, the caregiver is alerted and she administers a screening tool that measures the senior's cognitive state. The results are stored in the system database.

The CG ML module sends a number of follow-up actions to the Recommendation and Actuation Engine (RAE). These actions are also learned from the experiences of seniors and CGs in the database that tell us the beneficial effect of each action. The RAE executes those steps and records their results in the system database.

For example, a given senior might be prescribed four ten-minute sessions per day doing an exercise game on the Wii activity device, shake the senior's easy chair every hour to make sure they get up and walk for five minutes, and if they complete these tasks send a robot to their room with a chocolate chip cookie and warm milk (or another special treat) as a reward for good behavior.

This approach works because abnormal cognitive decline is reflected in increasing amounts of immobility, changes in eye movements, changes in conversational patterns, increased foot shuffling when walking, decreased sleep, changes in HVAC compared to past preferences, and forgetting the names of common objects. For example, we display the picture of a banana on the screen of the smart fridge and ask the senior to identify it. These are all features that are easily measured in a senior's instrumented living space, are correlated with abnormal decline in cognitive ability, and can be measured on a daily basis. This is a useful adjunct to the administration of MMSE tests that can only be done by trained medical professionals. Our approach helps identify dementia in its early stages and helps mitigate with appropriate intervention strategies. This addresses a significant societal problem with data in a unique way.

IOT Data Detects Changes in Eating, Sleep Patterns, Toileting

Based on experience with other patients, make changes to the diet, social interaction during meals, settings of the bed (elevation, etc.), and medications that have been beneficial to other seniors with similar symptoms.

The Caregiver (CG) machine learning module leverages the past experiences of vast numbers of CGs and Seniors to recommend strategies and actions that address problems they face every day. One example is the recognition of a CG's attitude toward a senior and recommendation of remedial tasks.

IOT Data Detects Changes in Social Interactions

Some studies have indicated that loneliness can be as large a risk factor to patient health as obesity. In one embodiment, IOT data is used to detect changes in the quantity and quality of a senior's social interactions. A senior's social interactions may change due to many factors, including the death of friends in the same age cohort, family moving to a different part of the country, etc. In one embodiment, recommendations for social interactions (e.g., accessing a social network of seniors) may be recommended based on experience with other seniors.

IOT Data to Modify Caregiver Attitude Toward Senior

The system identifies negative-trending changes in a CG's attitude and specific actions (monitored and verified), such as physical interactions with seniors (walking with them around the block) that benefit the senior and provide an opportunity for the CG and senior to bond.

Positive-trending changes in the CG's attitude toward the senior are rewarded with increased break time and automatic cooking of a CG's favorite dishes.

IOT Data to Detect Abusive Behavior of CGs Toward Seniors

In one embodiment, a training set is identified of seniors who've experienced a range of abusive behaviors from their caregivers, from mild forms such as missing medications or minimal social interaction, to more aggressive abuse such as verbal and physical punishment. Each abuse incident is graded on a scale of one to ten and matched to senior/CG pairs without grades using a gradient based regression tree (GBRT) classifier. This provides a score that tells us any particular senior is experiencing abusive behavior.

IOT Data to Detect Exemplary Behavior of CGs Toward Seniors

In one embodiment a training set is identified of seniors who've experienced a range of excellent behaviors from their caregivers, such as empathetic listening, exhibiting a calm demeanor, or creating stimulating social interactions. The system grades each example of exemplary behavior on a scale of one to ten and matches senior/CG pairs without grades to that data using a gradient based regression tree (GBRT) classifier. This provides a score that tells us whether any particular senior is experiencing superior care.

IOT Data to Recommend Training for Caregivers

Based on observations of IOT data from caregivers who knew how to do certain tasks (e.g., operate Hoyer lift) with specified levels of proficiency, we determine how well CGs with unknown levels of proficiency perform those same tasks. The machine learning system recommends training that helps the CG learn how to do those tasks.

In one embodiment, a CG/Senior Interaction Monitor is implemented with a logistic regression classifier that computes a score ranging from zero to one that measures the degree of interaction between the CG and the senior. Events (and the amount of time they occurred) are identified in the IOT data that are related to interaction between the CG and the senior. Examples include quiet conversation for Q minutes, card games together for G minutes, walking together for W minutes, stressed emotional conversation such as an argument for S minutes, eating together for E minutes, cooking together for C minutes, etc.

Training data for the interaction monitor is derived from a subset of all the interactions between caregivers and seniors recorded in the system database. The seniors in that subset voluntarily submitted self-evaluations of the amount of interaction they had with their caregiver on a scale of 1 to 10 over the previous N months (N is a configurable parameter). The events related to interaction between CGs and seniors that occurred during those N months periods and the self-evaluation scores are used to train a logistic regression classifier by a standard method of least squares.

The CG/Senior interaction score is computed by multiplying the input feature vector [Q, G, W, S, E, C] by the previously learned coefficients to obtain a score from 0 to 1. The higher the score is, the higher the degree of interaction between the CG and the senior.

The CG/Senior interaction score is computed at the completion of each shift and it's recorded in the system database. It's also passed on to the recommendation and actuation engine. The most recent N weeks of interaction scores are graded for degree of increase or decrease in interaction with a least-squares fit. This provides a correlation coefficient measures whether the interaction has increased, decreased, or stayed the same in the last N weeks. A positive correlation coefficient greater than a fixed threshold (e.g., 0.25) indicates increasing interaction. A negative correlation coefficient (e.g., <−0.25) indicates decreasing interaction and in between −0.25 and 0.25 indicates an unchanging amount of interaction. Note: the thresholds can be changed as needed.

If an increasing amount of interaction is noted, a positive entry is automatically inserted in the CG's employment record in the system database and a congratulatory message is posted on the smart fridge display screen and sent to the SPA on the family member's phone. If a decreasing amount of interaction is noted, a warning message is inserted in the CG's employment record, the CG's manager is notified, and given approval from the CG's manager, sensitivity training is recommended for the CG. If the amount of interaction is steady over the past N weeks, the score is recorded in the system database and no further action is taken.

In one embodiment, the Recommendation and Actuation Engine (RAE) receives instructions from the CG and Senior machine learning modules as well as the Interaction Monitor and ensures that they're carried out. The RAE has direct or indirect connections to the physical actuators mentioned earlier. The results of the instructions to the RAE are stored in the system database.

Exemplary Caregiver Recommendation System

Figure 3:
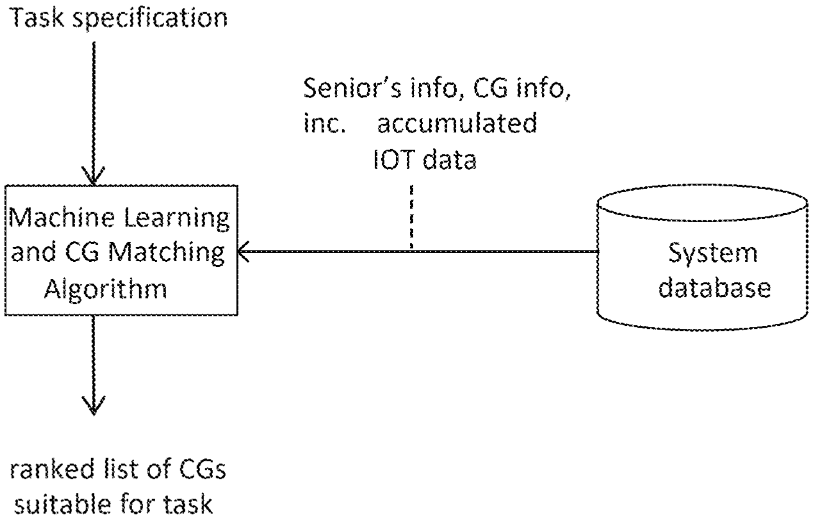
FIG. 3 illustrates a caregiver recommendation system in accordance with an embodiment.

FIG. 3 shows a Caregiver (CG) Recommendation System. It matches the specification for a task and the needs of senior, including their accumulated IOT data, to the system database. It outputs a ranked list of CGs based on how well they match the task and the behavior of the senior over time, as represented in their IOT data.

Further extensions include performing agency matching. For example, information on services offered by individual agencies, their geographical location, their CGs, etc. may be used to identify a match of an agency to the needs of a senior.

The task specification, typically entered by the scheduler at an agency, includes desirable demographic characteristics for the CG, including age range, gender, lifting requirements, etc. Skills or training the CG should possess, e.g. incontinence care, are also supplied. The care plan for the senior includes the tasks that are to be performed, whether they are companionship-related, housework, or medical.

Information about the senior including the IOT data accumulated to date as well as their medical history are retrieved from the system database. The IOT data includes their interactions with other caregivers in the past, any incidents that may have arisen (e.g., declining relationship reflected in increasingly argumentative verbal interactions) and how they were resolved (e.g., improved communication about how the senior likes their laundry to be folded and their eggs to be prepared).

Information about caregivers retrieved from the system database includes the IOT data accumulated about them to date as well as their demographic characteristics and performance on personality tests that measure communication skills, empathy, tolerance to different viewpoints, and interest in keeping up with current news, among other things.

The machine learning algorithm uses a set of training data comprised of past completed shifts that are graded by the senior and the caregiver for successful completion (1 to 10) and happiness (1 to 10). Those shifts are also characterized by the task specification for the shift, the tasks that were actually performed as well as the IOT data gathered during the shift. This information is used to train a deep learning algorithm that finds the N caregivers (N is typically 10) who best match a given shift specification. At run time, given a task specification and IOT data for a senior, the machine learning algorithm computes a ranked list of caregivers that best match the specified task.

Exemplary Telemedicine Applications

Figure 4:
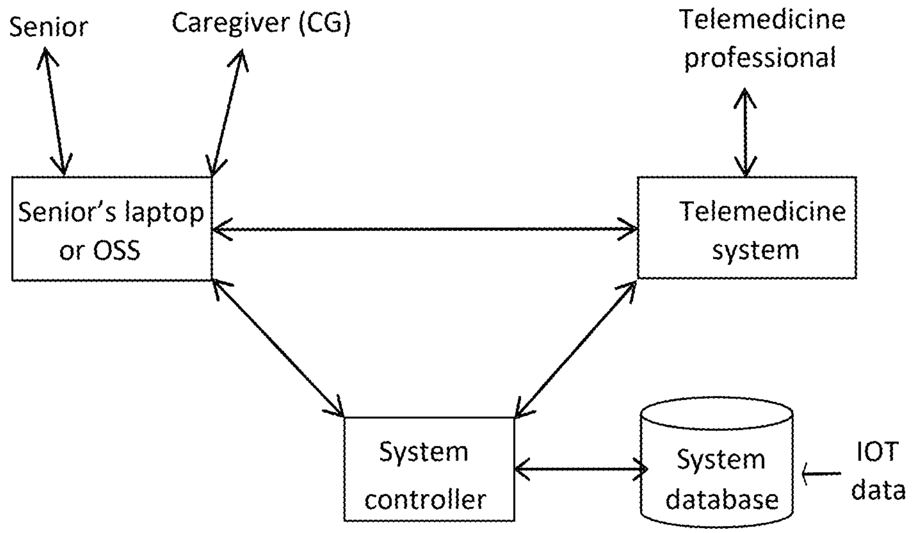
FIG. 4 illustrates a telemedicine system in accordance with an embodiment.

FIG. 4 shows the combination of the IOT system with a telemedicine system. In one embodiment, the telemedicine professional (TMP) accesses the senior's IOT data to help diagnose recent problems (increased loss of balance indicated by accelerometer data). The CG is simultaneously online with the TMP and the senior and helps the TMP diagnose and treat problems. IOT data from other seniors with similar symptoms and their outcomes after certain treatments informs the decisions of the TMP and the actions they recommend for the patient. For example, walking 15 minutes per day, lifting 5 pound weights for 10 minutes, and drinking 12 ounces of carrot juice are prescribed by the TMP for a given senior. The IOT system monitors compliance with these instructions.

Medication Compliance

Figure 5:
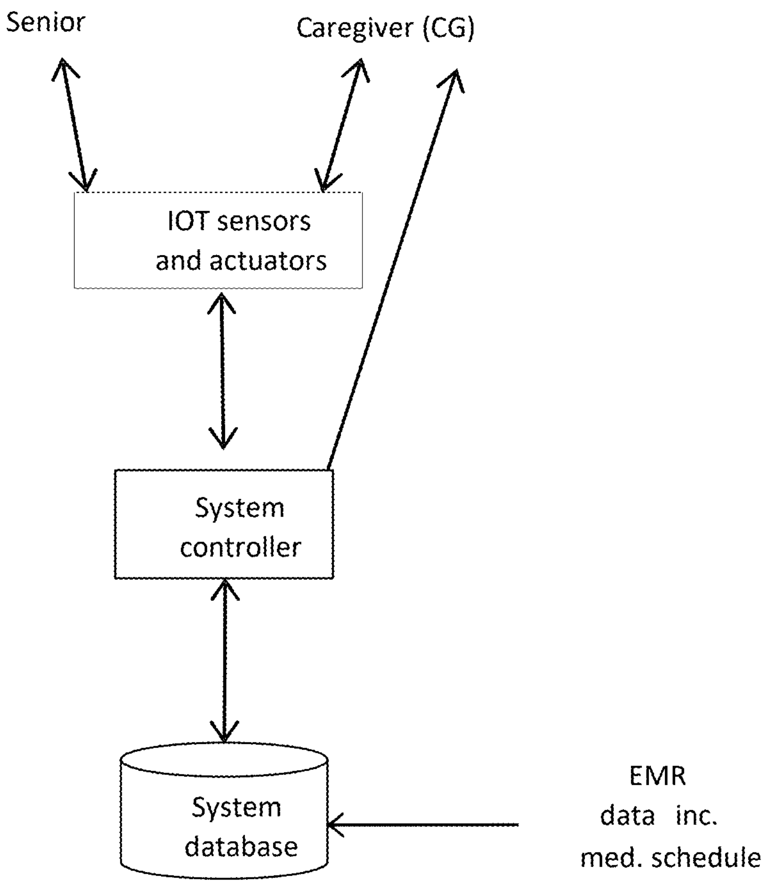
FIG. 5 illustrates a medication compliance system in accordance with an embodiment.

FIG. 5 shows the role of the IOT system in ensuring compliance with a medication administration schedule in accordance with an embodiment. A schedule is provided through the EMR system. The system controller provides instructions to the caregiver. The CG is responsible for logging compliance with that schedule. The sensors in the IOT system monitor that compliance. Specialized sensors (e.g., audio swallow detector) are employed as recommended by past experience of other seniors with similar patterns of IOT data. Actuators are used to remind and encourage compliance with the schedule. This can include playing messages on the voice assistants, videos on the smart fridge, buzzing the caregiver's phone, agitating the senior's chair or bed with a motor.

Examples of Health-Related Event Detection and Care Plan Management

Figure 6:
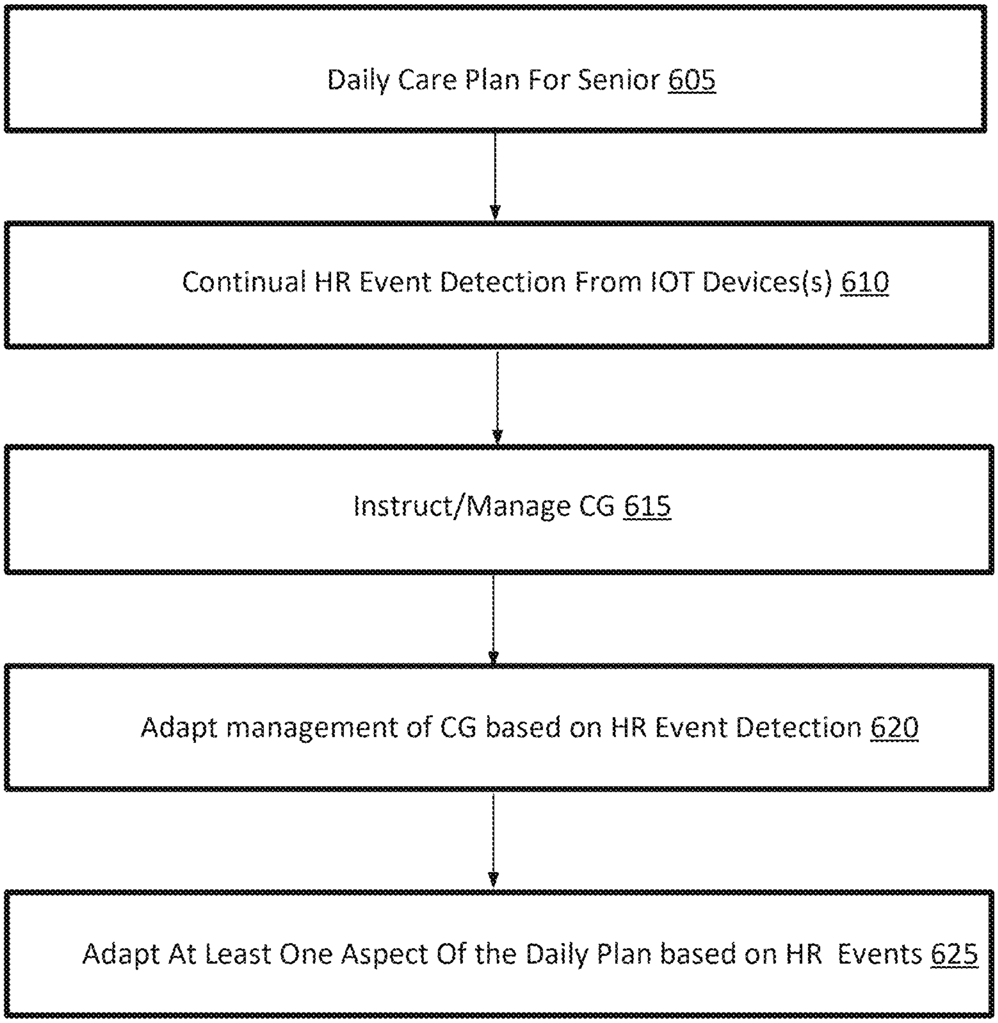
FIG. 6 illustrates a method of adapting a senior care plan in accordance with an embodiment.

FIG. 6 illustrates a method in accordance with an embodiment. In one embodiment, the daily health care plan for the senior is accessed 605. Continual HR event detection from IOT device(s) is monitored. The CG is managed 615 and may, for example, be given instructions to implement the daily care plan. In one embodiment, the management of the CG is adapted 620 based on HR event detection 610. For example, the CG may be given an alert if the voice stress analysis of the senior indicates that the senior is highly stressed. In some embodiments, one or more aspects of the daily plan may be adapted 625 based on the HR event detection. For example, if the senior is highly stressed, the CG could be given a new instruction to take an action selected to calm the senior, such as to smile more, do a calming activity with the senior, give the senior one of their favorite snacks, etc.

Figure 7:
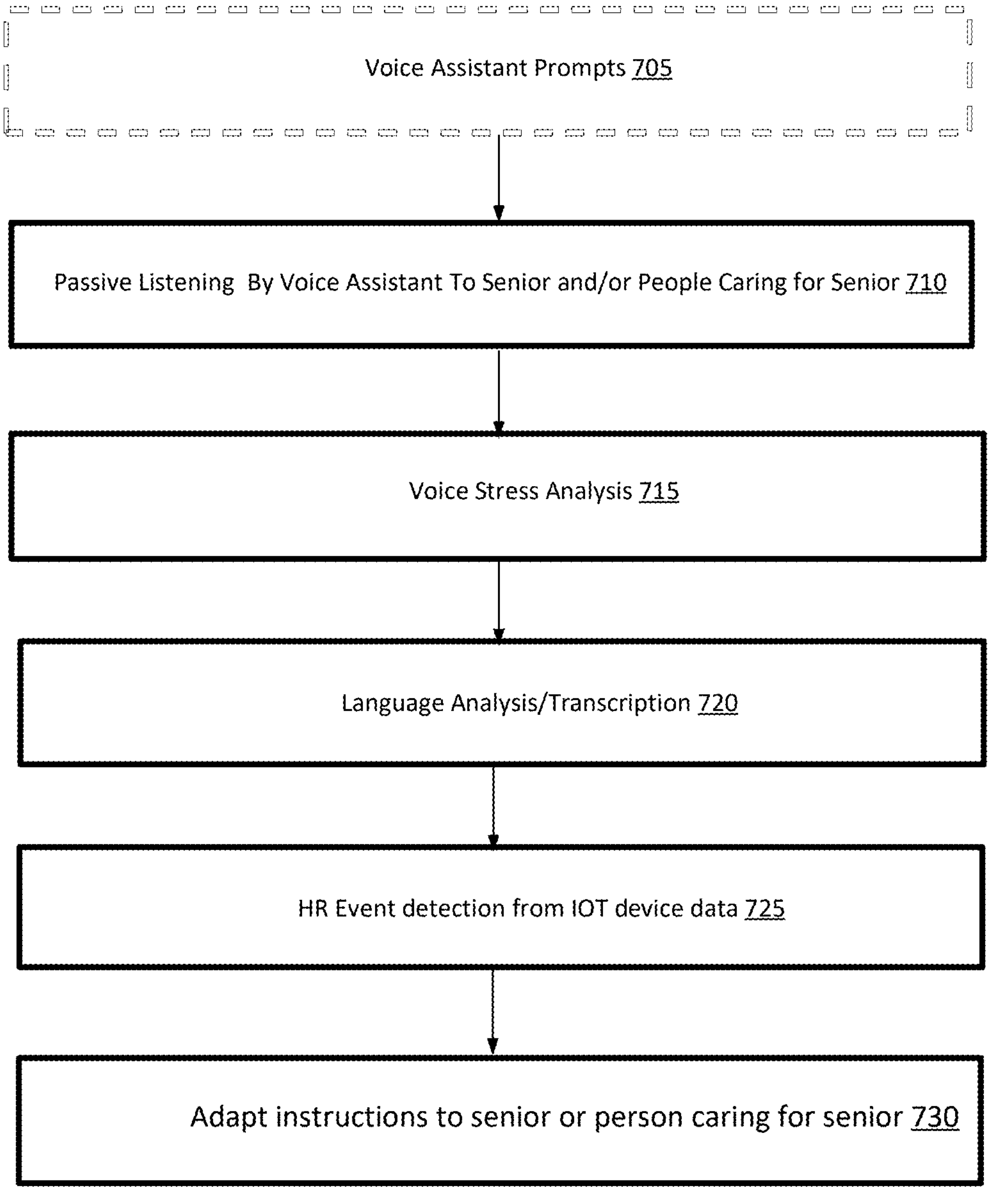
FIG. 7 illustrates a method of using a voice assistant to adapt instructions to a senior or a person caring for a senior in accordance with an embodiment.

FIG. 7 illustrates another example of a method. The voice assistant may optionally provide voice prompts 705, such as alerting the senior that the CG is about to arrive (e.g., "Your caregiver Donald is about to come") or asking a question of the senior ("How are you doing Alice?"). The voice assistant performs passive listening 710 to the senior and/or the person caring for the senior. Voice stress analysis is performed 715. Additional analysis 720 of the language of the senior or the person caring for the senior is performed. Other HR events are detected 725 from the IOT device data. The instructions given to the senior, or the person caring for the senior, may be adapted 730 based on the voice analysis and HR event data.

Figure 8:
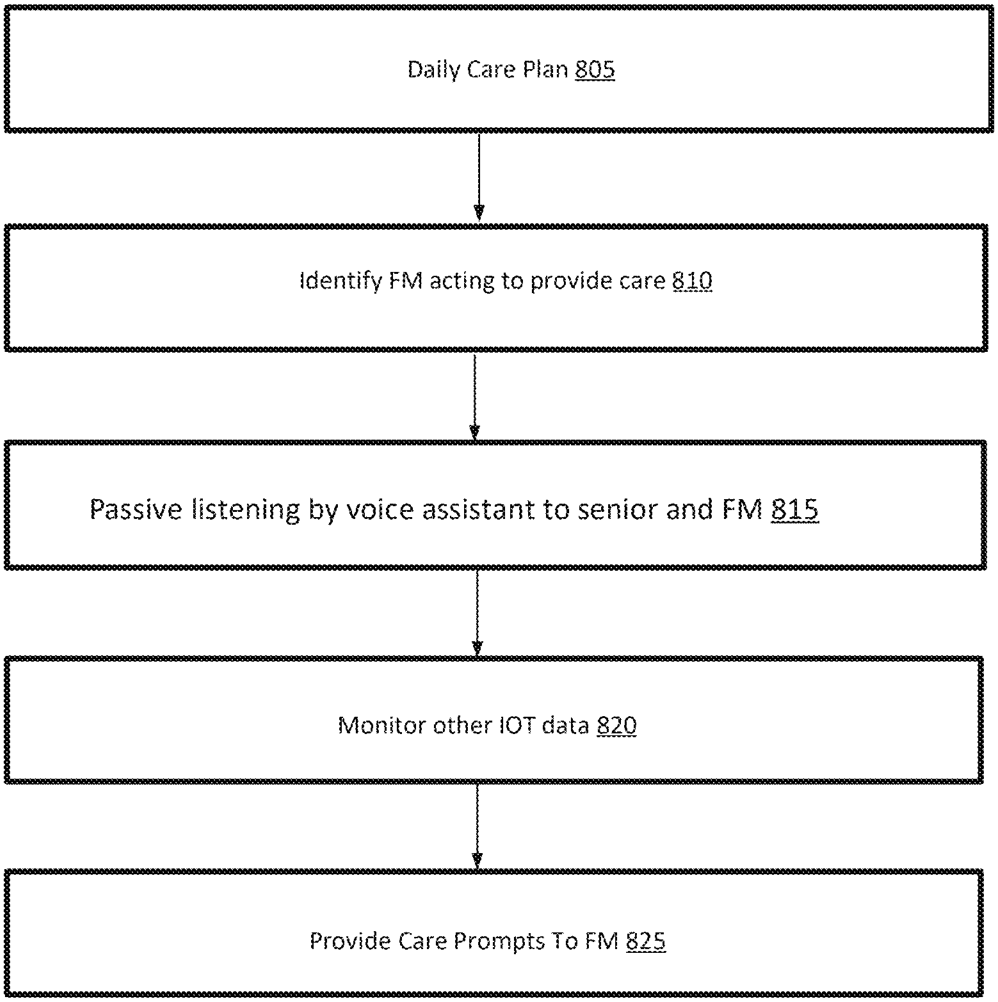
FIG. 8 illustrates a method of providing care prompts in accordance with an embodiment.

FIG. 8 illustrates another example of a method. The daily care plan for the senior is accessed 805. A family member is identified 810 that is acting to provide care. For example, the FMs phone SPA may identify the FM and geolocation used to identify that they are in the senior's home. Passive listening may be performed 815 by the voice assistant of the senior and the FM. Other HR events/IOT data may be monitored. The FM may be provided care prompts on their phone or via the voice assistant. For example, the FM may be given prompts regarding the medicines the senior is supposed to take and dietary restrictions for the senior (e.g., "Alice is to have no sugar, white rice, or white flour products to prevent her diabetes from getting worse").

Figure 9:
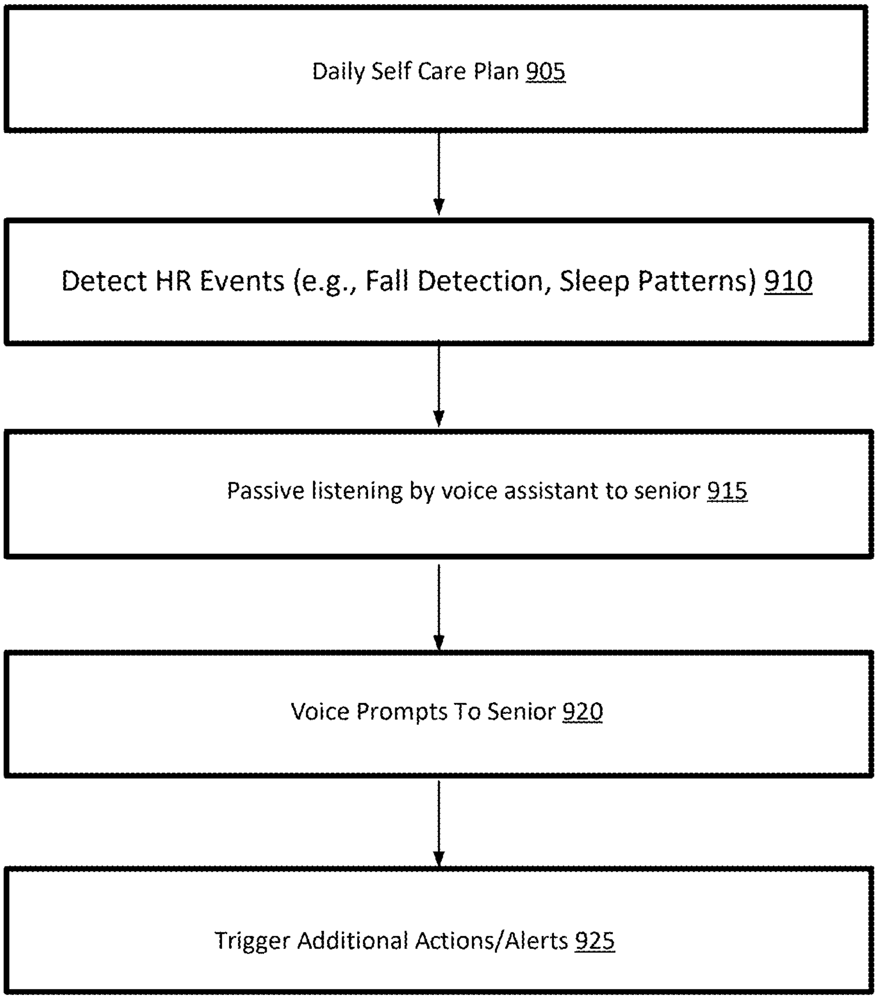
FIG. 9 illustrates a method of providing voice prompts to a senior in accordance with an embodiment.

FIG. 9 illustrates another example of a method. A daily self-care plan is accessed 905 for a senior, which may include social interactions. HR events are detected 910. As examples, the sleep patterns of the senior could be detected, bathroom behavior, or falls. The voice assistant may perform passive listening 915 of the senior. In some embodiments, voice prompts 920 may be provided to the senior (e.g., "Hello Alice, You have slept ten hours. Would you like me to schedule a call today with your daughter or your friend Judith?"). Additional actions or alerts may be scheduled 925 based on detected HR events (e.g., scheduling a CG visit if the senior is non-responsive).

Examples of Monitoring Physical Health Related Trend Data

Figure 10:
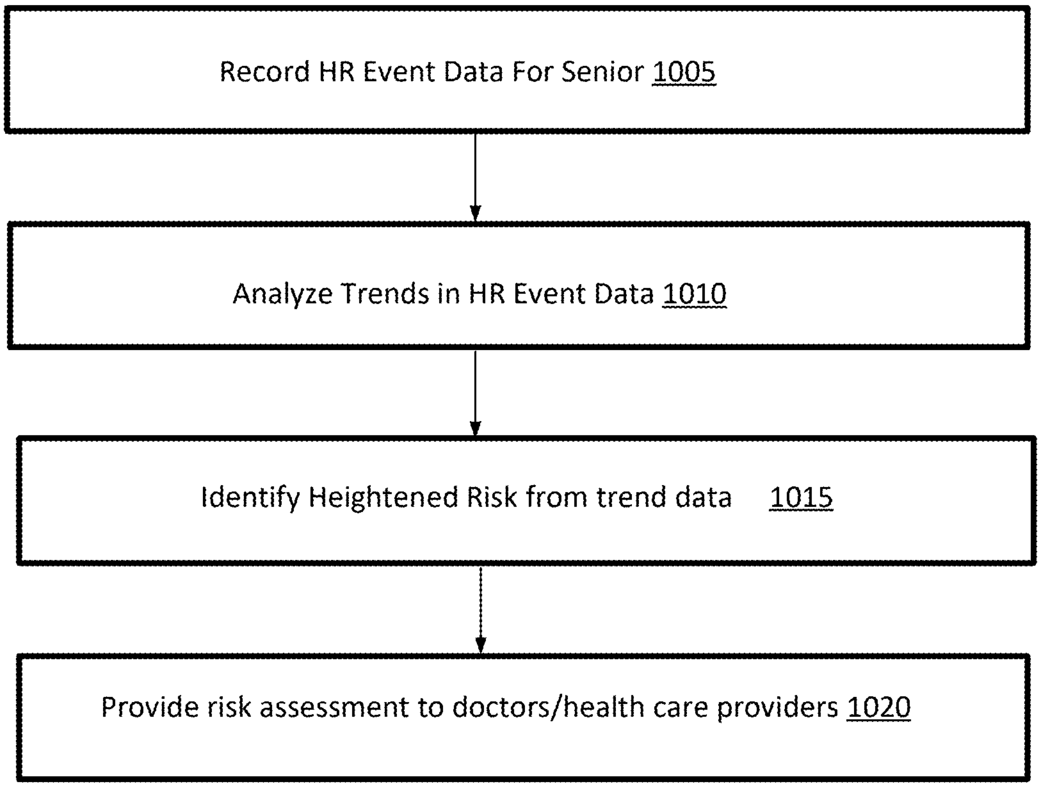
FIG. 10 illustrates a method of providing a risk assessment in accordance with an embodiment.

FIG. 10 illustrates another example of a method. HR Event data is recorded 1005 for a senior. Trends in the HR event data may be analyzed 1010. As an illustrative example, the trend could be changes to the gait, posture, or activity level of a senior. A potential heightened risk to the senior is identified 1015. For example, it could be a risk of falling based on a progressive neuromuscular decline of the senior. The risk assessment is provided to doctors or health care providers 1020. This may be in the form of an electronic report or a request for a health consultation/checkup in combination with the electronic report. As another example, the trend could be changes indicative of a change in cognitive level, such as a change in words used, change in eye movement, etc. that may be indicative of early onset of dementia or the progression of dementia.

In one embodiment, doctors or other health care providers could specify conditions in which they are to be notified of changes in trend data. For example, the raw trend data, or signals derived from the trend data, could be provided to doctors or heath providers as an aid in scheduling visits or consultations with doctors and specialists.

Additionally, some types of risks, such as a risk of falling, can be partially mitigated by changes to a senior's home (e.g., anti-slip bathroom features, nightlights, etc.) such that early detection of a risk may allow a care plan to be changed to reduce the chance of a debilitating injury to a senior. In some cases, early detection of a risk may allow doctors to be more effective and cost-effective medical care.

Figure 11:
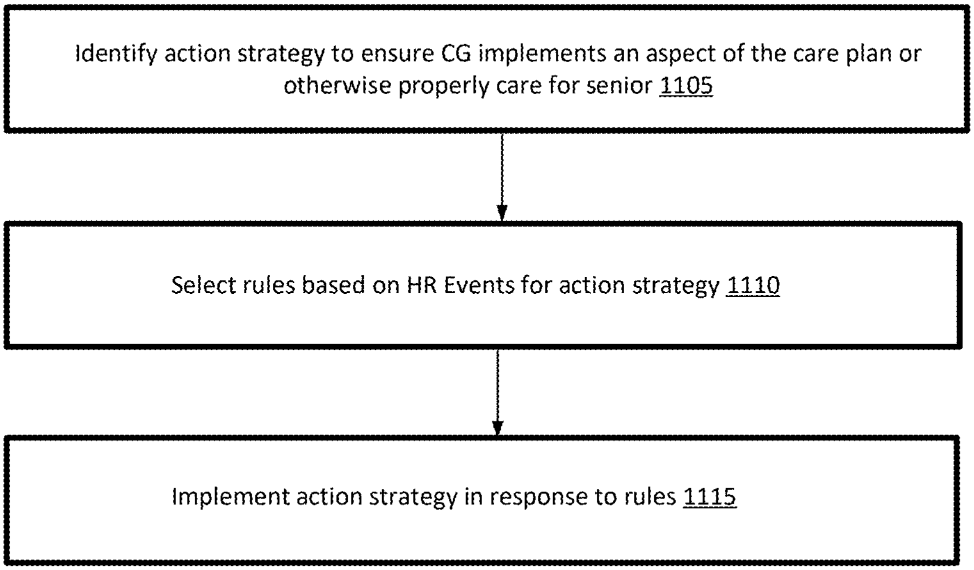
FIG. 11 illustrates a method of implementing an action plan in accordance with an embodiment.

As illustrated in FIG. 11, in a general method an action strategy is selected 1105 defining actions for a CG. The action strategy may include a selection of rules 1110 based on the occurrence of specific HR events to ensure the CG implements 1115 one or more aspects of the care plan or otherwise properly takes care of the senior. For example, the action strategy could be to detect one or more HR events indicating that the CG is not attending to the senior or implementing the care plan and taking an action to ensure that the CG implements the care plan.

Figure 12:
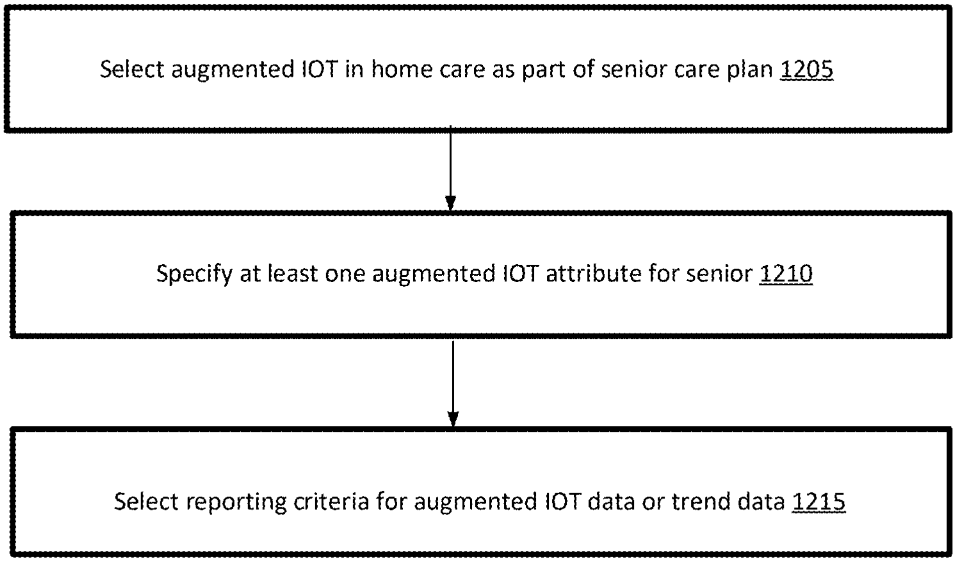
FIG. 12 illustrates a method of selecting reporting criteria for augmented IOT data in accordance with an embodiment.

In some embodiments, options may be provided for a medical doctor or health care provider for augmented IOT in-home heath care to be selected 1205 when designing a care plan for a senior. As indicated in FIG. 12, in one embodiment, a doctor or health care provider could be provided an option to specify 1210 augmented IOT care and at least one augmented IOT care attribute for the senior. In one embodiment, an option may be provided to select 1215 reporting of IOT data or trends identify from IOT data. For example, a medical doctor with an 85-year old patient could specify an augmented IOT care plan in which the IOT data is monitored for signs of the early onset of dementia and reported to the doctor or health care provider.

Figure 13:
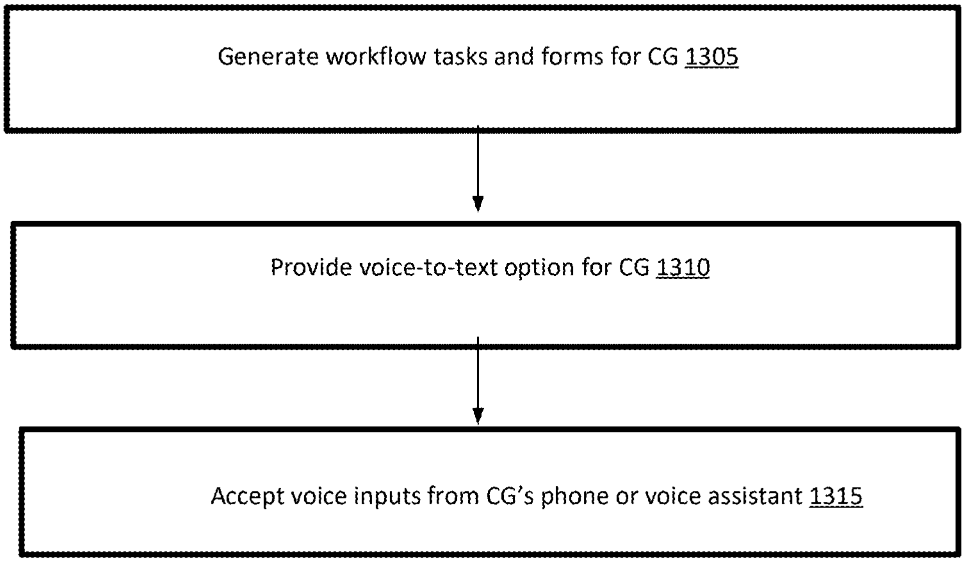
FIG. 13 illustrates a method of using voice inputs in a workflow in accordance with an embodiment.

In some embodiments, "voice forms" are provided for a CG to fill in workflow forms via command from the CG's phone or a voice assistant. As illustrated in FIG. 13, workflow tasks and forms are generated 1305 for the CG to fill out. A voice-to-text option is provided 1310 for the CG. Voice inputs are accepted 1315 from the CG's phone or a voice assistant.

Figure 14:
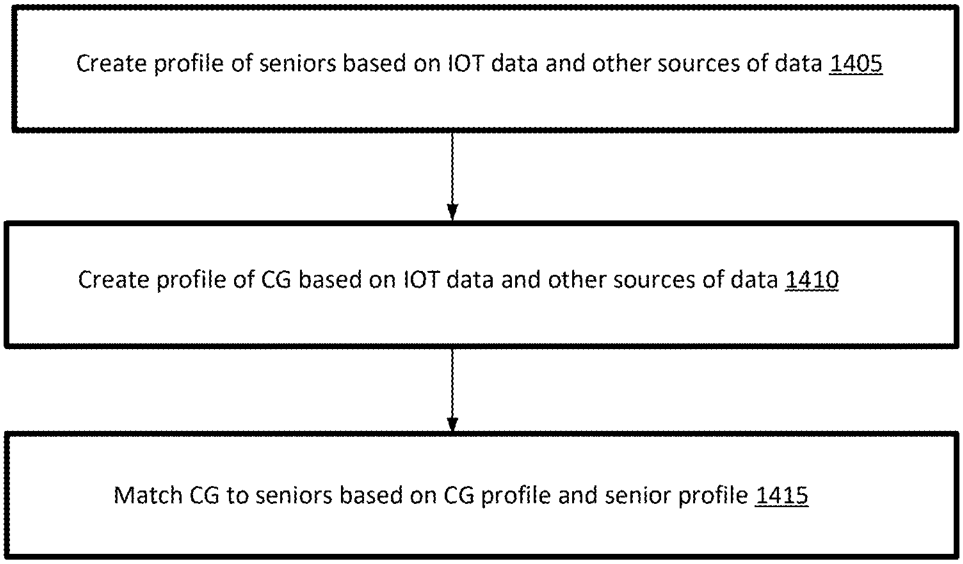
FIG. 14 illustrates a method of matching caregivers to seniors in accordance with an embodiment.

As illustrated in FIG. 14, in some embodiments matching of a CG to a senior is performed based in part on the IOT data. For example, a profile of a senior may be created 1405 based on available information augmented by the IOT data. For example, the IOT data may reveal behavioral trends of the senior, their general stress levels, response to stress, and response to different activities. A CG profile may also be created 1410 based on available information for a CG (e.g., employment history, background, available social media or telephone data, etc.). A CG may be matched 1415 to a senior based on the profile data for the senior and the CG.

Figure 15:
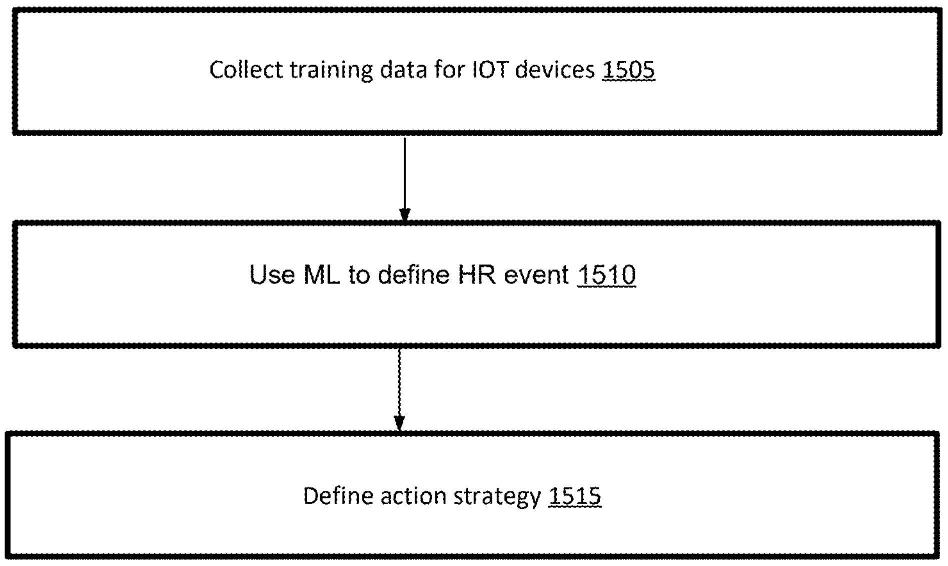
FIG. 15 illustrates a method of using machine learning to define an action strategy in accordance with an embodiment.

As illustrated in FIG. 15, in one embodiment data from IOT devices is collected 1505 to form training data. Machine learning is used to define HR events 1510 from the training data. Action strategies are then defined 1515 based on the HR events.

Psychological/Medical Condition Detection and IOT Customization

Figure 16:
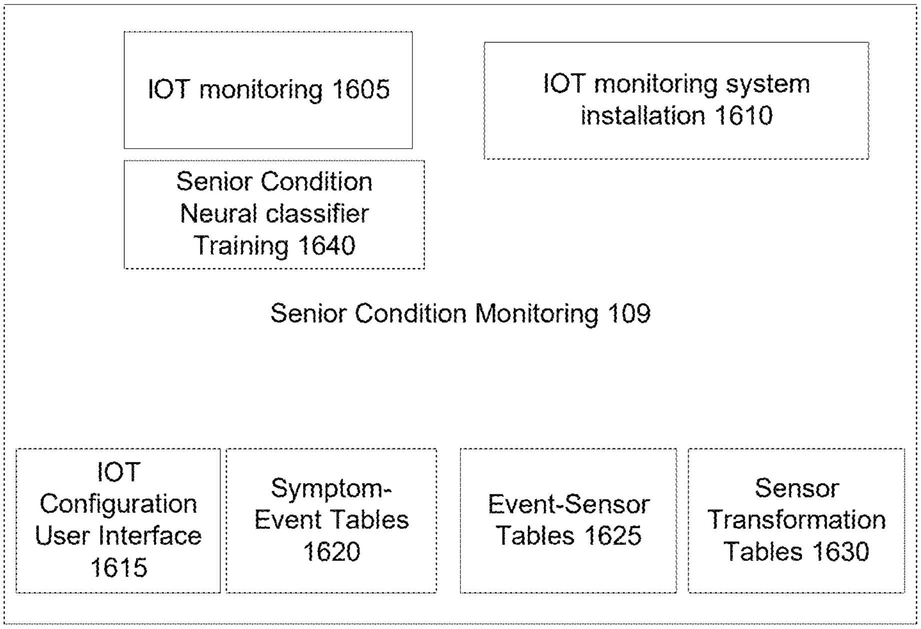
FIG. 16 illustrates an example of a senior condition monitoring module in accordance with an embodiment.

FIG. 16 is a block diagram of the senior condition monitoring module 109 in accordance with an embodiment. In one embodiment, a neural classifier training module 1640 is used to train a neural classifier for an IOT monitoring module 1605 to detect a psychological or medical condition based on sensor data. In one embodiment, an IOT monitoring system installation module is provided to aid in determining sensors required to detect a selected condition. In some embodiments, it also generates a cost-benefit analysis for installing sensors to detect a selected condition. In one embodiment, a set of tables 1620, 1625, and 1630 are generated to map a set of relationships between symptoms and events (corresponding to features of the symptom), event to sensor data, and sensor transformation functions to convert raw sensor data into sensor data for detecting medical or psychological conditions. In some embodiments a user interface 1615 is provided for configuring aspects of the monitoring, as described below in more detail. In one embodiment, the above described modules may be implemented as computer program instructions stored on a non-transitory computer readable medium and executable on a processor.

There are many psychological conditions, medical conditions, and overall health conditions that that can be detected by an IOT system. This is possible because the sensors in a patient's living area capture information that directly or indirectly measure features that can be correlated with various conditions.

Additionally, in some cases the selection, configuration, and operation of the sensors can be customized to aid in directly or indirectly measuring features that can be correlated with various conditions.

The psychological health of a senior is also correlated with their physical health. For example, a variety of psychological conditions, such as depression, have indirect health risks in the sense that a depressed senior is less likely to exercise, eat right, and take care of themselves. However, some studies also suggest direct health risks associated with psychological conditions due to the mind-body relation. The early detection of features correlated with psychological conditions are useful for improving the care of seniors.

The onset and progression of many psychological conditions is often indicated by changes (decline, increase, steady, erratic, etc.) in combinations of symptoms over recent periods of time [See S. Abdullah and T. Choudhury, Sensing Technologies for Monitoring Serious Mental Illness, IEEE Multimedia, January-March 2018, 61-75]. In one embodiment, the IOT system permits entry of a specification of a combination of symptoms and recent durations that are indicative of a condition. The system then automatically builds a machine learning system that computes whether that condition occurred during the specified time. The data sources include data captured by the sensors in the patient's IOT system. Additionally, the data sources may include data captured by other patients' IOT systems. For example, if there are 100,000 patients in anIOT SC database, many of them may be at risk for the same psychological conditions, such as a risk for depression.

One issue in using an IOT system to detect a condition is related to installing and using sensors. In many cases, there may be no commercially available IOT sensor for symptoms. For example, there is no IOT sleep sensor that outputs a patient's sleep quality at any point in time. Instead, there are IOT sensors for events that are correlated with symptoms. Sleep quality can be correlated with motion (the more still a person is, the better is that person's sleep quality), respiration (reduced respiration rate is correlated with deep sleep), and heart rate (reduced heart rate is correlated with deep sleep).

A related problem is that patients often may have unique configurations of sensors in their living space in terms of the number, arrangement, and types of sensors. One person may have two motion detectors in the bedroom, a microphone-based system for respiration rate measurement, and a smart watch for heart rate monitoring. Another person may have a single bedside radar sensor that detects motion, respiration and heart rates. This can make it difficult to compare the sleep quality of such patients since a typical system would compare the raw output of similar sensors such as the number of motion events detected by two infrared motion detectors.

In one embodiment, the IOT system supports a process 1750 to determine the IOT sensors to be installed in a patient's home. The IOT installation process may determine the required sensors and associated installation cost to provide sensors in an individual patient's home to detect a given condition. A cost benefit analysis may also be provided for a decision maker who determines whether to proceed with an IOT installation in a patient's living space. For example, if a patient's living space doesn't include sensors necessary to detect a condition, such as mild depression within a selected degree of accuracy, the required sensors, installation cost, and cost-benefit analysis are computed.

Figure 17:
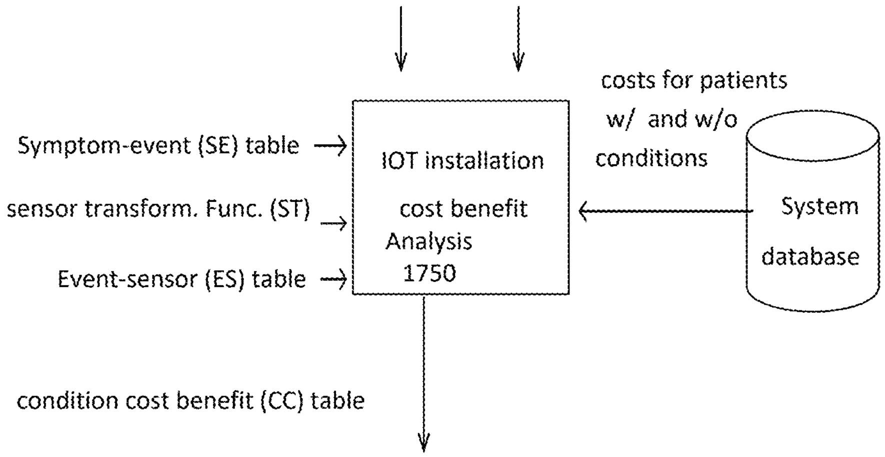
FIG. 17 illustrates an IOT monitoring system installation process in accordance with an embodiment.

FIG. 17 illustrates an example of an IOT installation process in accordance with an embodiment. The IOT system installation process in FIG. 17 provides, in one embodiment, an output of required sensors to detect symptoms of a condition. In some embodiments, installation cost is also output. In one embodiment, the system database provides historical information of the costs for patients with and without specific conditions. In one embodiment, the IOT system installation process uses this information to generate a cost-benefit analysis.

In one embodiment, the inputs to the IOT system installation process 1750 for a given subject patient includes a description of a patient's living space, physical layout and XY dimensions of each room (bedroom, living room, kitchen, bathroom, on patient, on caregiver, etc.). In one embodiment, the living space description also includes information about the presence of Wi-Fi in each room and the internet connectivity (cable modem DSL, satellite, etc.) and speed of the connection.

In one embodiment, the IOT installation cost benefit analysis computes the minimum set of sensors (Si) required for each condition (numbered i) as well as their installation cost (ICi) and their maintenance cost (MCi,j) over the next three years. A symptom-event table (SE), lists all the conditions that the IOT system can monitor, the symptoms of those conditions, etc. (see FIG. 22), the sensor transformation function table ST, and the event-sensor(ES) table that lists all available sensors, their installation and maintenance costs, etc.

The benefit calculation, expressed as Bi,j for condition i and time period j, incorporates information about health related outcomes supplied by analysis of medical claims data that shows how much it costs to care for patients with the condition i that have an IOT system versus patients with condition i who do not have an IOT system. For example, since we can detect a change in sleeping patterns in patients who have mild depression, we can intervene with low cost treatment programs, such as targeted outreach by caregivers, before the condition becomes major depression that requires hospitalization, drug treatment, etc. The cost and benefit calculations also include information about the cohort of patients that are selected from the system database. This includes their geographic location, age range, time since being diagnosed with the condition, yearly income or socio-economic ranking, etc. For example, an agency owner might want to compare the costs and benefits for patients with mild depression in rural Kentucky as well as the costs and benefits for patients with stage four lung cancer in Lexington.

For a given cohort of patients over which we calculate the analysis (e.g., lung cancer patients in Kentucky), there is an associated definition for the living space of a patient, as well as the SE, ES, and ST tables. In one embodiment, the process considers each condition C in the symptom event table SE (see FIG. 22) and calculate the benefit for each of three years that's enjoyed by the cohort of patients with and without condition C. (Three years is a commonly used period of time for cost benefit calculations, although it will be understood that a different number of years may be used in the cost-benefit calculation, such as one year, two years, three years, four years, etc.) The benefit_calc( ) function retrieves insurance claims information for the cohort of patients from the system database and uses that to calculate the total insurance claims for cohort members who had the condition and had an IOT system versus those who had the condition but did not have an IOT system.

For each symptom associated with a condition, we calculate the minimum set of sensors that can measure that event using information from the event sensor mapping table ES (see FIG. 23) and add those to the required sensor for that condition. The process then calculates the installation and maintenance costs for those sets of sensors over the next three years using information in the sensor transformation table ST (see FIG. 24).

Pseudo code for the IOT installation cost benefit analysis is shown below:

```
function IOT_installation_cost_benefit_analysis( cohort, living_space, SE, ES, ST ) {
   # compute the condition cost benefit table (CCB)
   CCB = [ ][ ];
   CCB[ num ][ 'row num.' ] = num = 1;
   for each condition C in SE {
      CCB[ num ][ 'condition' ] = C;
      # calculate financial benefits for condition C that are enjoyed by the cohort
      for j = 1 to 3 {
         CCB[ num ] [ benefit year j ] = benefit_calc( C, j, cohort );
      }
      foreach symptom S in SE[ C ] {
         min_sensors = null;
         # find minimum set of sensors that can measure each event
         foreach event E in SE[ C ] [ S ] {
            min_sensors = min_sensors + min_cost_sensor( sensors in ES[ E ]);
         }
         CCB[ num ][ 'required sensors' ] = min_sensors;
         IC[ num ] = MC[ num ][ ] =0;
         # calculate installation and maintenance costs for the minimum set of sensors
         foreach sensor S in min_sensors {
            IC[ C ] = IC[ C ] + ST[ S ][ 'install cost' ];
            for j = 1 to 3 {
               MC[ num ][ j ] = MC[ num ][ j ] + ST[ S ][ 'maintenance cost' ];
            }
         }
      }
      CCB[ num ][ 'install cost' ] = IC[ num ];
      for j=1 to 3 {
         CCB[ num ][ MC year j ] = MC[ num ][ j ];
      }
      num = num + 1;
   }
   return CCB;
}
```

In one embodiment, the IOT installation cost benefit analysis helps guide the installation of sensors of IOT systems. It can be used, for example, by a decision maker to make decisions on upgrading or adding additional sensors to the living space of a patient. In some embodiments, it can provide guidance on the arrangement of sensors in a patient's living space.

In one embodiment, agency operators can determine how much it will cost them to install and maintain it for a selected number of years (e.g., three years) and they can use this information to set the prices they charge their customers. They can use the information about how the maintenance costs were derived (e.g. frequency of battery changes, tutoring of caregivers about testing sensor performance, probability of sensor failure, frequency of rebooting, etc.) to understand their expected maintenance burden (e.g., skill level of personnel required) and adjust the maintenance costs accordingly. For example, if their caregivers could not change the battery in a smoke detector on the ceiling and they would need an electrician with a tall ladder instead (perhaps because of union regulations), the $2.50 cost in the CCB table could become $110.

The IOT monitoring system installation process could be provided as a stand-alone data-driven service to insurance companies. Insurance companies could use this system to understand the operating costs (installation plus maintenance) as well as the amount they will save for arbitrary populations of patients. This can be used in setting reimbursement rates for patients who install IOT systems. For example, suppose that an IOT system for stage four lung cancer patients in Kentucky could cost $150 to install and if maintained for three years would save the insurance company $15,000 over that time because it would reduce hospital readmissions. An insurance company might choose to reimburse those patients $450 with the extra $300 being an incentive that motivates patients to deal with the hassle of installing the system.

The IOT monitoring system installation process could be provided as a stand-alone data-driven service to health care providers. Health care providers could use this system to understand the conditions that would most benefit from IOT instrumented living spaces and the reasons for those benefits. This information can be used to help patients understand why they should obtain such a system. For example, suppose there is a 95% chance that a patient in Kentucky with stage four lung cancer will need a hospitalization in the next year that can be avoided with home care. This information comes from the analysis that was performed in computing the benefits values (Bi) in the CCB table. Health care providers could sell the contact information for patients who would benefit from an IOT instrumented living space and base the prices for those leads on data in the CCB table. For example, Health care providers could charge agencies $100 for each patient whose projected first year benefit is greater than $2000 because they know the maintenance costs are only $150 per year and 85% of the patients who are offered such a system actually buy it.

Figure 18:
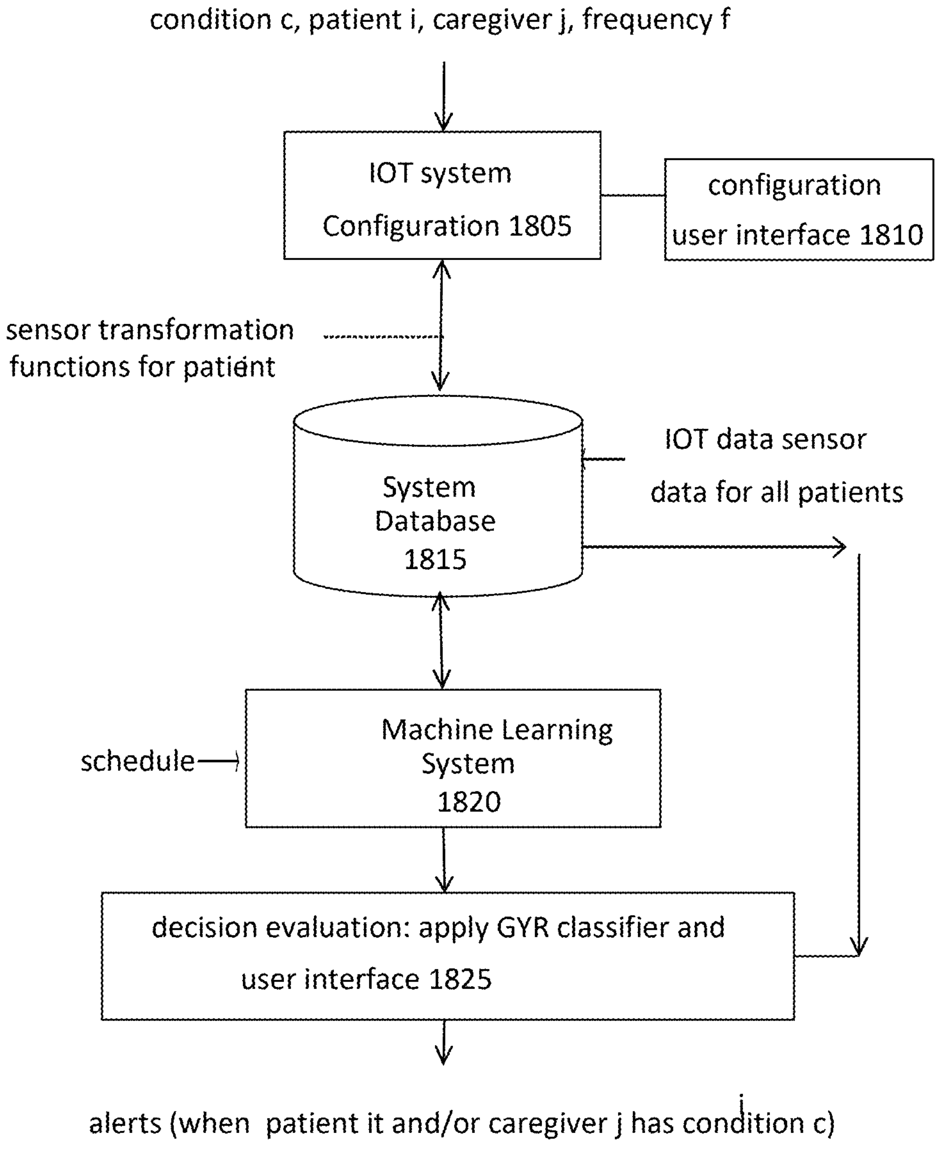
FIG. 18 illustrates an embodiment of an IOT monitoring system in accordance with an embodiment.

FIG. 18 illustrates a method for providing a detection alert when a detection is made that a patient or caregiver has a specific condition, c. In one embodiment, an input to the IOT system configuration 1805 includes a condition c, patient i, caregiver j, and frequency f are supplied by the user when the system is configured. The frequency (e.g., daily) is the frequency at which either patient i or caregiver j are tested for the presence of condition c.

The configuration user interface 1810 controls the IOT system configuration process. It prepares a set of sensor transformation functions for a patient's IOT-instrumented living space (see example in FIG. 19) that transform the raw data provided by the sensors into numeric features that can be used for machine learning system 1820.

Those sensor transformation functions and the parameters for them that were chosen and/or confirmed by the user are stored in the system database 1815. The system database 1815 also includes IOT sensor data for every patient.

In one embodiment, as determined by a schedule, the machine learning (ML) system retrieves the sensor transformation functions for patient i and/or caregiver j at the appropriate interval (e.g., daily) as well as the required IOT data and transformation functions for other patients and it decides 1825 whether to issue an alert about the detection of condition c in patient i and/or caregiver j.

In one embodiment, a decision evaluation routine 1825 determines whether an alert should be issued, who should receive it and how the alert should be transmitted. This can be done automatically or controlled manually with a user interface.

An example of a senior's living space instrumented with IOT sensors mentioned earlier is shown in FIG. 19. In this example, the location of each sensor is indicated along with the sensor type.

The identity of each sensor and its location is shown in the sensor floorplan (SF) table in FIG. 19(*a*), the distribution of the sensors within the living space is shown in the floor plan in FIG. 19(*b*), and sensors carried by both the senior and a caregiver are shown in FIG. 19(*c*). The table and floor plan diagram are created when sensors are installed in a patient's living space and used later in the running system and user interfaces. As is often the case, but not necessarily so, an on-site server (OSS) is installed next to the TV. The OSS is connected to each of the sensors listed in FIG. 19(*a*) over a low power wireless link and it bridges the data they produce over the internet to the System Controller (see FIG. 1A). There is an IR motion detector, ultrasonic motion detector, radar sensor, smart speaker, and blood pressure monitor in the bedroom. There is a video camera facing the couch and a smart speaker in the living room. A smart speaker and video and ultrasonic motion detectors are focused on the kitchen area. An IR motion detector is placed in the bathroom and the patient has a smart phone, smart watch, and pedometer on his person. The caregiver carries a smart phone. As per FIG. 1, all these devices are connected to the system controller either through the OSS or through a remote networked service provider via an internet connection.

An example of the configuration user interface is shown in FIG. 20(*a*) in accordance with an embodiment. A doctor or other health care professional (the user) with knowledge about the symptoms associated with a given condition and the durations over which changes in those symptoms occur when the patient has mild depression utilizes a user interface to select symptoms and durations. Default values for symptoms and durations are supplied by the system and the user can modify them.

FIG. 20(*b*) shows an example of an agency owner or manager adjusting the parameters for an algorithm that assesses caregiver job performance.

Figure 21:
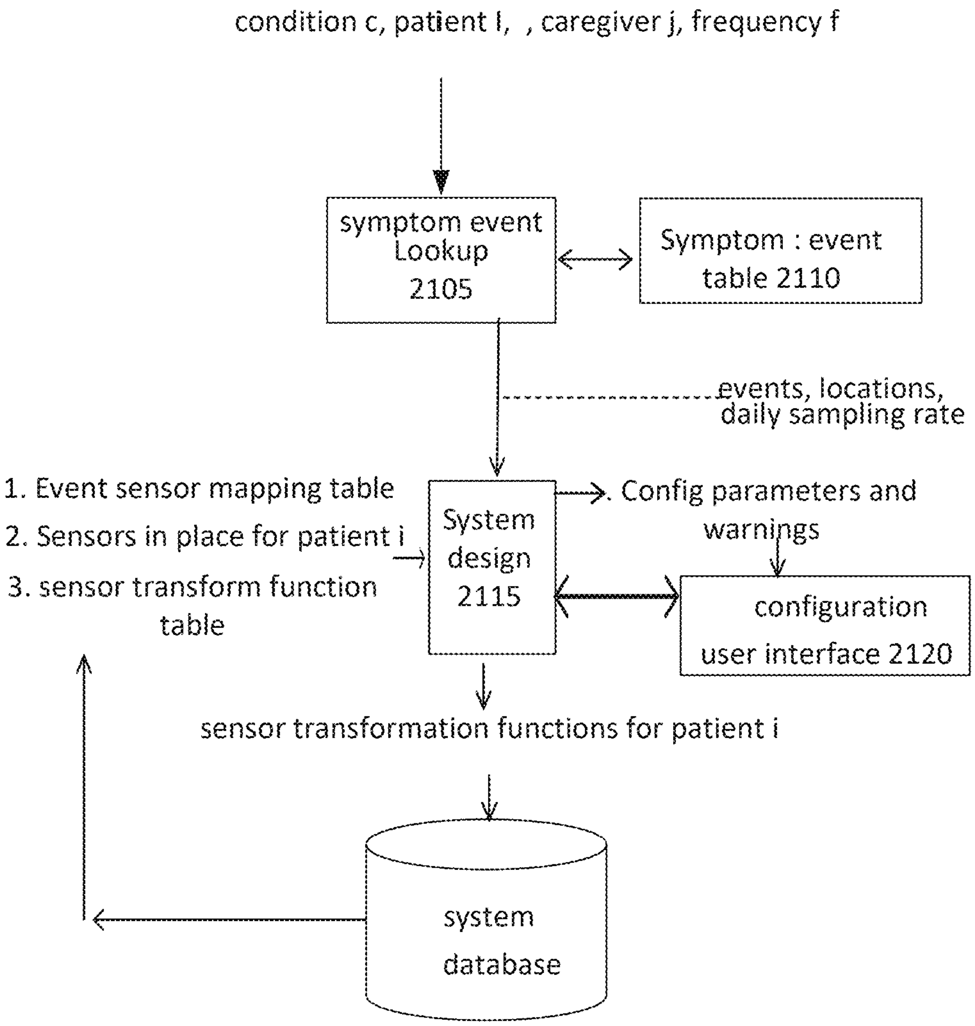
FIG. 21 illustrates an IOT system configuration in accordance with an embodiment.

FIG. 21 shows the IOT system configuration routine in accordance with an embodiment. The user supplies a condition, patient or caregiver and frequency. A symptom-event lookup 2105 accesses a symptom-event (SE) table 2110 (example shown in FIG. 22) that is consulted to retrieve the symptoms of the indicated condition, the events (e.g., feature of the symptom) that measure those symptoms, the location within the patient's living space where those events should be measured, the recent duration over which those events are monitored, and the daily sampling rate at which they should be measured. The system design 2115 further takes into consideration and event-sensor mapping table, the placement of sensors, and a sensor transformation function table.

For example, to determine whether a patient has mild depression, that patient could have sleep quality changes over the past 30 days, mobility changes over the last 90 days, and TV time changes over the past 15 days that are similar to other patients that have mild depression. To assess sleep quality, we therefore need to sense motion, respiration and heart rate in the bedroom four times per day. To assess mobility, we need to sense step count and stairs climbed anywhere four times per day. To assess TV time we need to assess minutes of TV watched twice per day anywhere.

To determine caregiver performance, the caregiver would have changes in patient interaction over the past 30 days, changes in meal preparation over the past 15 days, and changes in walking together performance over the past 60 days. To assess patient interaction, we therefore need to sense conversation frequency and co-location everywhere, kitchen sounds and motion events in the kitchen, and step counts and co-location everywhere.

FIG. 22 is an example of the symptom-event (SE) lookup table. It provides the symptoms associated with each health-related condition, the events associated with each symptom, the duration over which those events should be measured and the rate at which each event is sampled every day. Medical expertise is embodied in the judicious choice of events and duration and is informed by the medical literature and physicians' general education. The symptom event lookup table allows us to specify events that we can measure in place of symptoms that cannot be sensed. The symptom event lookup table also allows us to configure the dimensionality of the normalized feature vectors used for the classifier. This is significant since it determines the number of nodes in the neural network, the amount of data required to train the network and the number of iterations needed for training. For example, the length of the feature vector for mild depression is 3 (motion, respiration, heart rate)*30*4 (daily sampling rate)+2*90*4+1*15*2=360+720+30=1110.

FIG. 23 is an example of an event-sensor mapping table. The system design routine in FIG. 21 consults the event-sensor(ES) mapping table (example shown in FIG. 23) to determine which sensors are required to measure the events specified in the symptom: event table (example in FIG. 21). In assessing sleep quality, we need at least one of either IR, ultrasonic, or radar motion detectors, a smart watch or smart phone pedometer, or a video camera in the patient's bedroom. We also need either a smart watch, radar sensor, or smart speaker in the patient's bedroom to measure respiration, and either a smart watch, radar sensor, or blood pressure monitor in the patient's bedroom to measure heart rate. To assess mobility, the patient needs a smart watch, smart phone, or pedometer to measure step count and either a smart phone or pedometer to measure stairs climbed. To assess TV time, there should be either a smart TV or a video camera focused on the space in front of the patient's TV that produces video from which we can determine when the patient watches TV.

The information about the sensors that can measure the conditions specified by the user is compared by the system design routine to the sensors that are installed in the patient's living area. If there is not at least one of the required sensors present (i.e., a sensor is missing), the corresponding event cannot be sensed and therefore the corresponding symptom cannot be assessed. Information about missing sensors is returned to the configuration user interface and if a symptom cannot be assessed because of a lack of a sensor, the user is so advised.

FIG. 24 illustrates an example of a sensor transformation (ST) function table. The system design routine also consults ST function table to determine how to convert the raw data received from the sensors to data that can be used by the machine learning algorithm. Since different sensors for the same characteristic can produce data at varying rates, as shown in the detection rates in FIG. 23, for example an IR motion detector counts motion events every minute and an ultrasonic motion detector counts motion events every two minutes, we provide a downsample function that normalizes the data produced by those sensors to a standard rate. Pseudo code for the downsample function is shown below:

```
function downsample( sensor_readings[ ], detection_rate, interval_width ) {
   # sensor_readings[i], i=1, ... ,N, from beginning to end of date range
   # detection_rate is in minutes
   # interval_width is in times per day
   # return array events that counts number of events in corresponding time interval
   # convert_interval width to same scale as sensor_readings[ ]
   interval_width = ((1/interval_width) * 60 * 24 ) / detection_rate;
   event_count = 0;
   for (i=0; i<N; ++i ) {
      count = 0;
      for( j = i; j < i + interval_width; ++j ) {
         count = count + sensor_readings[j];
      }
      events[ event_count++ ] = count;
   }
   return events;
}
```

The sensor_readings[ ] array contains the raw data from the sensor. The detection_rate is the rate data is produced by the sensor and is retrieved from the event-sensor mapping table in FIG. 23. The interval_width is the rate at which data is stored in the events[ ] array. The default value for interval_width is retrieved from the sensor transformation table and can be changed with the configuration user interface if necessary. In the above code, downsampling is performed by adding all the sensor values within each interval_width. Other functions could also be applied such as smoothing with averaging, computing the median, computing the standard deviation, etc. The system configuration routine, in the manner of an object oriented software system, stores the code for the downsample function and the parameters that were chosen by the user (interval_width) in the system database. This is done for each of the sensors in the patient's living space that needs to be downsampled. In our example in FIG. 18 and using the information in the sensor transformation function table, that would be the IR, ultrasonic, and radar motion detectors as well as the smart phone, smart watch and pedometer.

Video cameras are also powerful motion detectors since they can be specialized to detect the amount of motion as compared to the IR and other technologies that determine only whether or not a pre-determined amount of motion occurred. Pseudo code for the video_motion detection function is shown below. It receives the sequence of video frames produced by the video camera in the video_data[ ] array. The frame_rate is a parameter of the sensor and is retrieved from the sensor transformation function table and cannot be changed by the user. The sampling_window is a configuration parameter of the motion detection algorithm. It is retrieved from the sensor transformation function table and can be changed by the user if necessary. The motion detection algorithm counts the number of motion events that occur every interval_width minutes. It does this by comparing every two frames that are separated by the sampling_window parameter.

The interval_width and sampling_window are stored in the sensor transformation table as minutes since this is more understandable for users than frame rates. The process converts them to the corresponding number of frames and compute the difference between pairs of frames with the frame_diff function. If the percentage of pixels in two frames that are different from one another exceeds the pct_diff parameter, we have detected motion at that point in time and the count value is incremented. The total number of motion events that are detected within each interval_width frames is stored in the events [ ] array. The pct_diff parameter allows the user to adjust the amount of motion that is detected. This is significant in our application since we can then use a video camera to detect small amounts of motion, such as a patient breathing while sleeping, that could not be detected by a conventional infrared (IR) motion detector. As before for the downsample function, once the user confirms the selection of parameters, the code for the function and the parameter values are stored in the system database for the corresponding video camera, as illustrated in the example below:

```
function video motion( video_data[ ], frame_rate, interval_width, sampling_window, pct_diff)
{
  # count num. motion events every interval_width minutes
  # video_data[ ] is sequence of frames, video_rate is frames per second
  # detect motion by comparing two frames every sampling_window frames apart
  # motion occurs if more than pct_diff percent pixels are different
  N = number of frames in video_data
  event_count = 0;
  interval_width = interval_width * 60 * frame_rate; # convert interval_width to frames
  sampling_window = sampling_window * 60 * frame_rate; # convert sampling_window to
frames
  for ( i=0; i<N; i += interval_width ) {
    count = 0;
    for (j=i; j < i + interval_width; ++j ) {
      if (j mod sampling_window == 0 && j > i &&
          frame_diff(video_data[ j - sampling_window], video_data[j]) > pct_diff) {
        ++count;
      }
    }
    events[ event_count++ ] = count;
  }
  return events;
}
```

In one embodiment the frame diff function It is given two video frames and it returns the number of pixels that are different when the frames are compared 1:1. This is done by converting the frames to binary images, comparing pairs of pixels with a mathematical exclusive or function and counting the number of pairs where the exclusive or returns true. The function returns the percentage of pixels that are different. We use the Ostu binarization algorithm [Nobuyuki Otsu (1979). "A threshold selection method from gray-level histograms". IEEE Trans. Sys., Man., Cyber. 9 (1): 62-66] and found that it works well in our type of application, but other binarization algorithms could be used as well. The code for the frame_diff( ) function is also stored in the system database.

Pseudo code for an embodiment of the frame_diff function is shown below:

```
function frame_diff( frame_i, frame_j ) {
  # return percent of corresponding pixels that are different between frame_i and frame_j
  # binarize( ) converts a gray scale or color video frame to binary.
  #    We use the Otsu algorithm.
  # rows( ) and cols( ) return that rows and columns in a given video frame
  # XOR( ) is the standard mathematical exclusive or function
  frame_i = binarize( frame_i );
  frame_j = binarize( frame_j );
  count = 0;
  for ( i=0; i < rows( frame_i ); ++i ) {
    for ( j=0; j < cols( frame_i ); ++j ) {
      if (XOR( frame_i[i][j], frame_j[i][j] ) {
        ++count;
      }
    }
  }
  return 100.0 * count / ( rows(frame_j) * cols(frame_i) );
}
```

Figure 25:
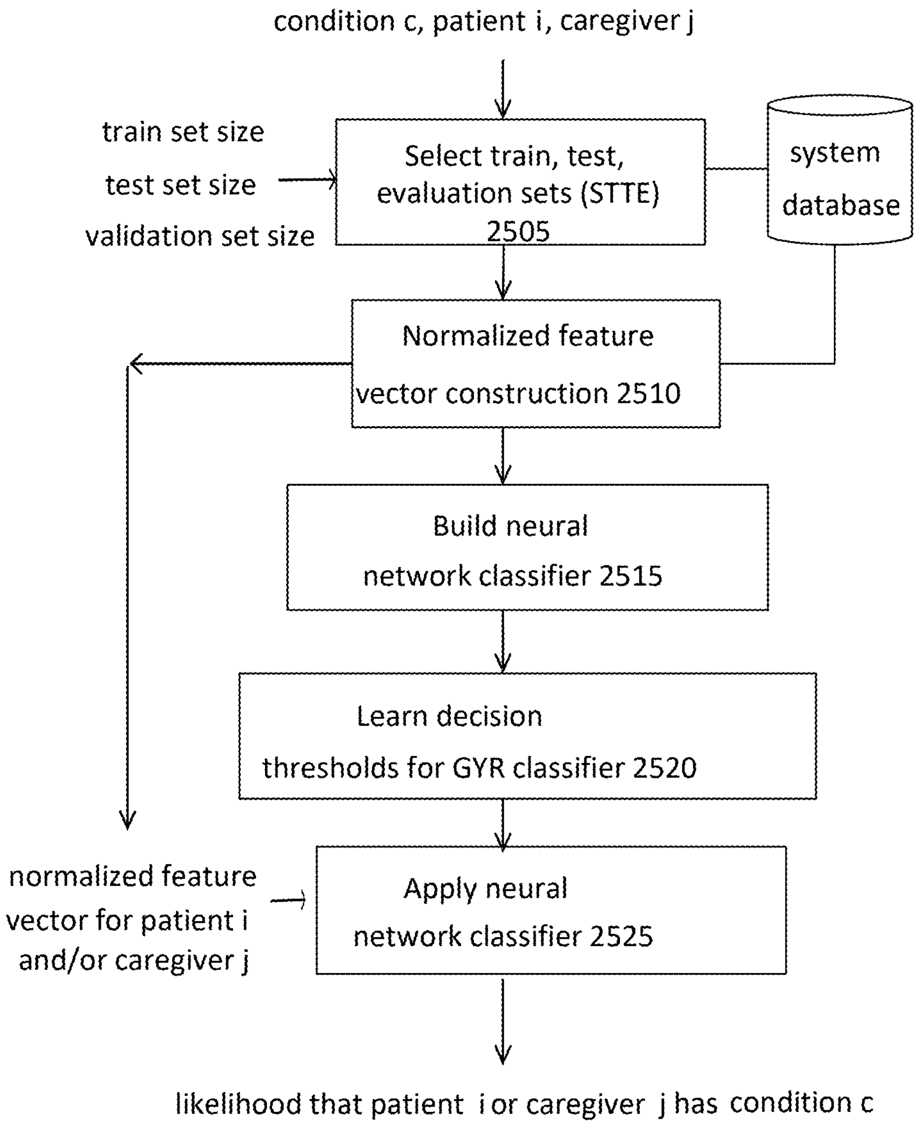
FIG. 25 illustrates a machine learning system to identify a patient condition in accordance with an embodiment.

FIG. 25 shows an embodiment of a machine learning system process that determines whether a specific patient and/or specific caregiver has condition c. A select train, test, and validation sets step accesses a specified number of people from the system database. They are patients or caregivers who have been evaluated for the presence of condition c. In block 2510, the process constructs normalized feature vectors for each of those people. A neural network classifier is built in block 2515 for two groups of patients (those that have the condition and those that don't). In block 2520, the process learns the decision thresholds for a logistic regression (LR) classifier that computes the probability that the given patient has the condition. In block 2525 the neural network classifier is applied to the patient's or caregiver's normalized feature vector and pass the result through the logistic regression classifier to produce a decision (in the form of a probability) whether the patient or caregiver has condition c.

An exemplary select train, test, validation sets function (STTE) is provided in one embodiment. It is given the condition being tested for (c), identifiers for specific patients or caregivers, and the desired number of patients in the train, test and validation sets. It first retrieves a super set which contains patients who have been evaluated for condition c (pseudo SQL is given) and it then randomly selects subsets of the super set and assigns them to the train, test, and evaluation sets. Pseudo code for the select train, test, validation sets function (STTE) is shown below:

The SDRN function is given a condition C, an identifier for a patient i, the sensor transformation functions for that patient in set ST, and an end date. The end date is the end of an interval over which we evaluate the patient's performance. For example, if we want to see whether the patient exhibits signs of mild depression today, we set the end date to today's date. If we want to see whether the patient exhibited signs of mild depression 30 days ago, we set the end date to 30 days prior to today's date.

We retrieve each event E associated with condition C from the symptom event table SE. For each day from the end_date minus the duration over which the event E is evaluated (as specified in the symptom event table entry for the event E) and for each sensor S that can sense the event (as specified in the event sensor mapping table ES) and that is in the patient's living space (as specified in patient i's sensor floorplan SF), we retrieve the data produced by S in patient i's living space on day D and store the data in SD. We then apply the sensor transformation for S to SD and store the result in SDT. Once the data produced by every sensor that can evaluate event E on day D has been transformed, we normalize that data and store it in the normalized feature vector at NFV [E, D]. The apply_sensor_transformation and event_normalization functions each produce vectors that have a number of elements equal to the daily sampling rate for each event, as specified in the symptom event table. As we can see by inspection of the pseudo code for SDRN, the normalized feature vector NFV has a number of elements equal to the sum of the duration*daily sampling rate for each of the events associated with condition C in the

```
function STTE( condition c, patient i, caregiver j, train_set_size, test_set_size,
    eval_set_size ) {
  N = train_set_size + test_set_size + eval_set_size;
  super_set = SELECT N FROM PATIENT_TABLE WHERE c IN PATIENT_TABLE[
eval_conditions ]
  train_set = random_sample( train_set_size, super_set);
  test_set = random_sample( test_set_size, super_set - train_set );
  valid_set = super _set - train_set - test_set;
  return_train_set, test_set, eval_set;
}
```

Figure 26:
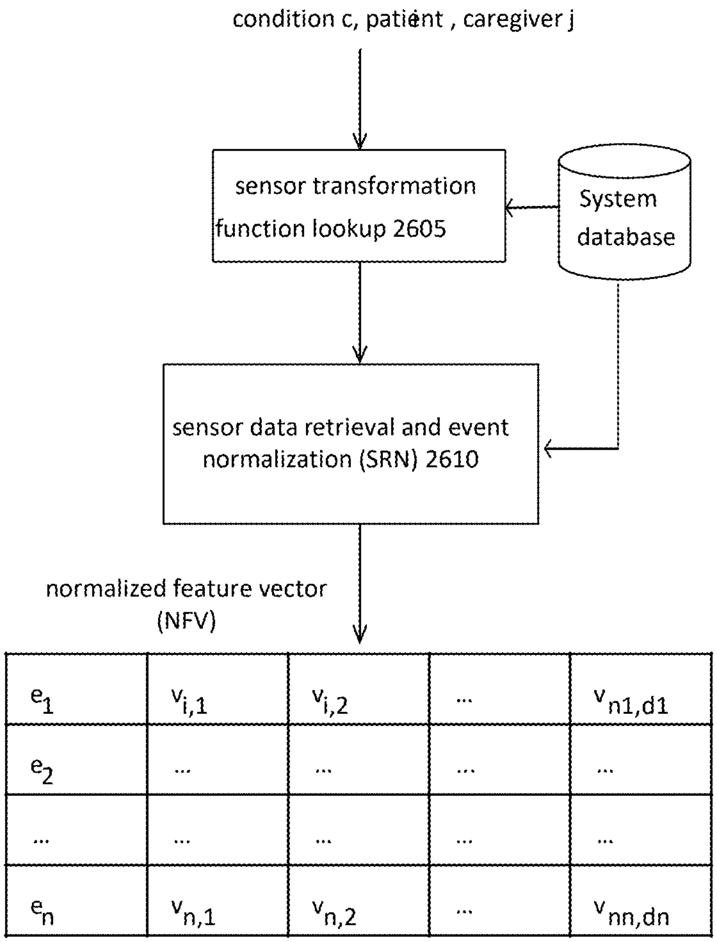
FIG. 26 illustrates normalized feature vector construction in accordance with an embodiment.

FIG. 26 illustrates a normalized feature vector construction routine in accordance with an embodiment. For a given condition and a patient or caregiver that may or may not have the condition. We first lookup 2605 the previously configured sensor transformation functions for that patient or caregiver. The sensor data retrieval and normalization (SDRN) function then retrieves 2610 all the data produced by the specified patient's IOT system over the number of days specified by the symptom event lookup table. It then applies those transformation functions to that data and it produces a normalized feature vector. Pseudo code for the SDRN function is shown below:

symptom event table. In the case of mild depression, this is 30*4*3+90*4*2+15*2=1110.

Pseudo code for the retrieve_data function is shown below. A pseudo SQL statement is shown that retrieves all the data that was produced by sensor S in patient i's living space on day D.

```
function retrieve_data (patient i, sensor S, day D) {
  #return all the data produced by patient's sensor S on
    day D
  SD=SELECT*FROM DATA_TABLE(i, S, D);
  return SD;
}
```

```
function SDRN( condition C, patient i, sensor transformation functions ST, end_date ) {
  # return normalized feature vector for condition C, patient i from end_date back in time
  for each event E in SE[ C ] {
    for each day D from end_date - SE[ E[ duration ] ] to end_date {
      sensor_count = 0;
      for each sensor S where (S in ES[ E ]) and (S in SF[ i, E[ location ] ]) {
        SD = retrieve_data( i, S, D );
        SDT[ sensor_count++ ] = apply_sensor_transformation( S, ST, SD );
      }
      NFV[ E, D ] = event_normalization( SDT, sensor_count, E[ daily_sampling_rate ] );
    }
  }
  return NFV;
}
```

In one embodiment, the sensor transformation function that was previously instantiated for sensor S is applied to the sensor data in SD using the previously set parameter values that are retrieved by the get_params( ) method. As an example, if we had retrieved all the data produced by an IR motion detector on a given day, the downsample function would be applied to that data using the values for detection_rate and interval_width that had been set or confirmed with the configuration user interface in FIG. 20. Pseudo code for an apply_sensor_transformation function is shown below:

```
function apply_sensor_transformation (S, ST, SD) {
  #apply the sensor transformation ST to the sensor data
    in SD
  SDT=ST[S](SD, ST[S].get_params( ));
  return SDT;
}
```

An event normalization routine calculates a vector NFV of normalized features. SDT is the transformed sensor data for each of the sensor_count sensors that measure event E. SDT contains daily_sampling_rate values for each sensor. We produce one vector of normalized values that represents the responses of all the sensor_count sensors. For example, if we have one patient with two motion detectors in their bedroom, one IR and one ultrasonic and the IR detector produced 450 activations from midnight to 6 AM and the ultrasonic produced 420 activations during the same time, the NFV value would be 435. Pseudo code for the event normalization routine, that calculates a vector NFV of normalized feature values, is shown below:

Referring back to FIG. 25, in one embodiment, after we apply the normalized feature vector construction routine to the data for patient i as well as the patients in the train, test and validation sets, we now have normalized feature vectors for a given patient as well as a sample of patients that either have or do not have the condition. We then build a neural network classifier for a supervised classification problem with one output: a floating point value that expresses whether patient has the condition. This procedure uses the typical combination of forward and backward propagation with the following parameters.

Configuration-number of input nodes, number of hidden layers and the number of nodes in each layer. The number of input nodes is the sum of the number of features for each event times the duration of the event times the daily sampling rate over the symptoms for each condition (1110 in our example for mild depression). A single hidden layer with N nodes where N is 2/3 of the number of input nodes plus the number of output nodes. In our example, that is (2/3)*1110+1=741. Other configurations of hidden nodes, layers of nodes, and numbers of nodes in each layer can also be determined experimentally that optimize recognition performance on the validation and testing sets. We use one output node because we are computing a binary result.

Initial biases and weights—we assign random floating point numbers as the initial biases and weights.

Activation function—we use a sigmoid function.

Learning rate—this is a single floating point value. We've found that 0.5 works well.

Momentum—this is also a single floating point number. We've found that 0.01 works well.

```
function event_normalization( SDT, sensor_count, daily_sampling_rate ) {
  for (i=0; i<sensor_count; ++i) {
    for (j=0; j<daily_sampling_rate; ++j) {
      NFV[ i*j ] = NFV[ i*j ] + SDT[ i*j ];
    }
  }
  for (i=0; i < sensor_count*daily_sampling_rate; ++i ) {
    NFV[i] = NFV[i] / sensor_count;
  }
  return NFV;
}
```

FIG. 27 shows an example of one day as it might appear for normalized feature vectors for a patient that has mild depression compared to a patient that does not. We see in this example that from midnight to 6 AM the depressed patient has a high number of motion events, elevated respiration, high heart rate, and non-zero step count (indicating trips to the bathroom). This indicates someone who's up and down all night long and has poor quality of sleep. In contrast, during the same time the patient without mild depression has normalized features consistent with a solid night's sleep (low motion, respiration, heart rate, step count and stairs climbed).

FIG. 28 shows an example of one day from a normalized feature vector for a caregiver that exhibits good job performance compared to a caregiver that does not. We see that the caregiver with good job performance consistently socializes with the patient and diligently attends to their duties in the kitchen and their responsibility to ensure that the patient is performing their required steps every day. In contrast, a caregiver with bad job performance does not talk much with the patient, expends little effort in the kitchen, and does not make sure the patient is doing their prescribed number of steps per day.

Number of iterations and leaning rate—these parameters control the amount of time needed for training the network. We prefer a fixed number of iterations for practical reasons. Typically, 1500 iterations are sufficient to train the network.

The forward and backward propagation steps are repeated for a fixed number of iterations or until the network training converges.

Figure 29A:
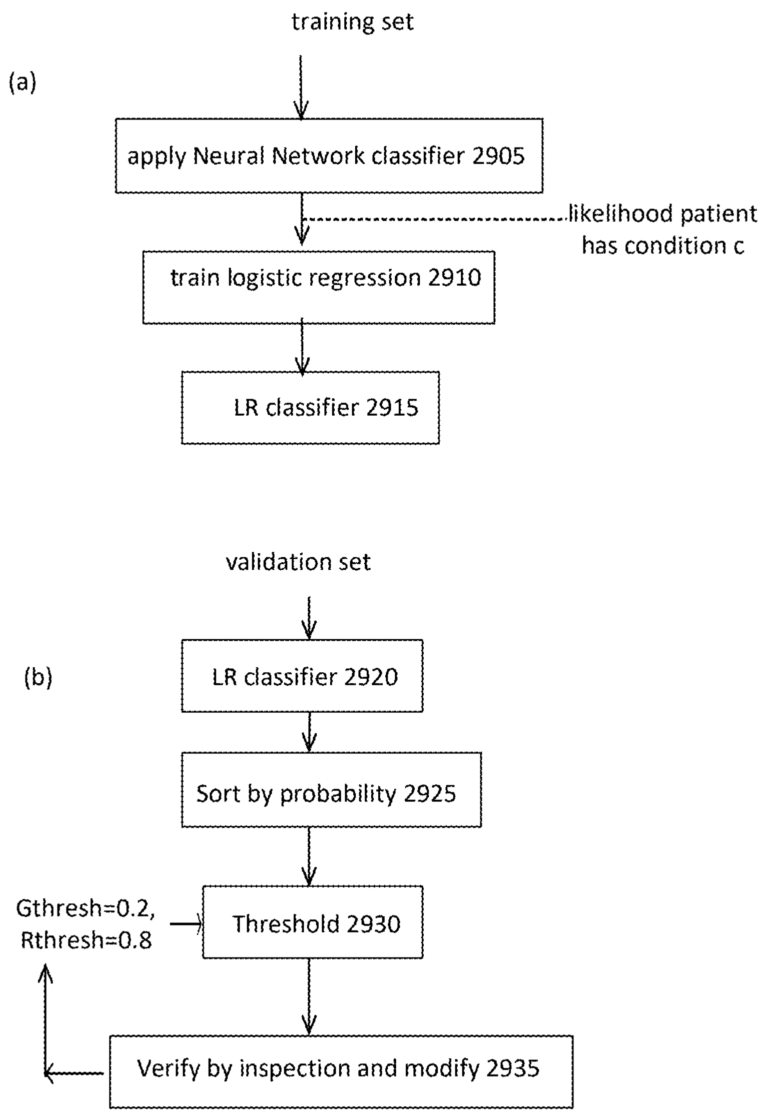
FIGS. 29A and 29B illustrate a method of learning decision thresholds in accordance with an embodiment.

We also learn the decision thresholds for a logistic regression classifier using the procedure shown in FIG. 29(*a*). The process "applies" each sample in the training set to the network by running one pass of the feedforward process. This gives us floating point value for each sample. The process then uses these results (normalized feature vectors from the training set, known conditions, and likelihood assigned by the neural network) to train a logistic regression classifier that the inventors refer to as a GYR classifier.

The Green, Yellow, Red (GYR) classifier assigns one of three colors to each patient or caregiver (the following description uses the term "caregiver" going forward with the understanding that the user interface could be applied to either patients or caregivers). A caregiver in the Green group is considered not to have condition c. A caregiver in the yellow group is at moderate risk for developing condition c and a caregiver in the red group is at high risk for condition c. These are caregivers that could demand immediate attention and personal intervention if necessary. The operator (e.g., home care agency manager) could choose to issue an alert about that patient.

FIG. 29(*b*) shows a Green, Yellow, Red classifier that uses the output of the logistic regression (LR) classifier that we trained in FIG. 29(*a*). After training the LR classifier on a set of training data, we apply it to a different set of feature vectors and classes (the end-observed variable that indicates whether the patient has the condition) called the validation data. The LR classifier returns a probability that the corresponding patient has condition c. The process sorts those feature vectors by that probability. It adjusts two thresholds ($G_{thresh}$ for the Green level and $R_{thresh}$ for the Red level) and display the result graphically as shown on the right side of FIG. 28(*b*). All the feature vectors below $G_{thresh}$ are assigned "does not have condition c" and those above $R_{thresh}$ are assigned "has condition c" as their result. The process then compares those decisions of the GYR classifier to the actual decisions of the caregivers.

Figure 29B:
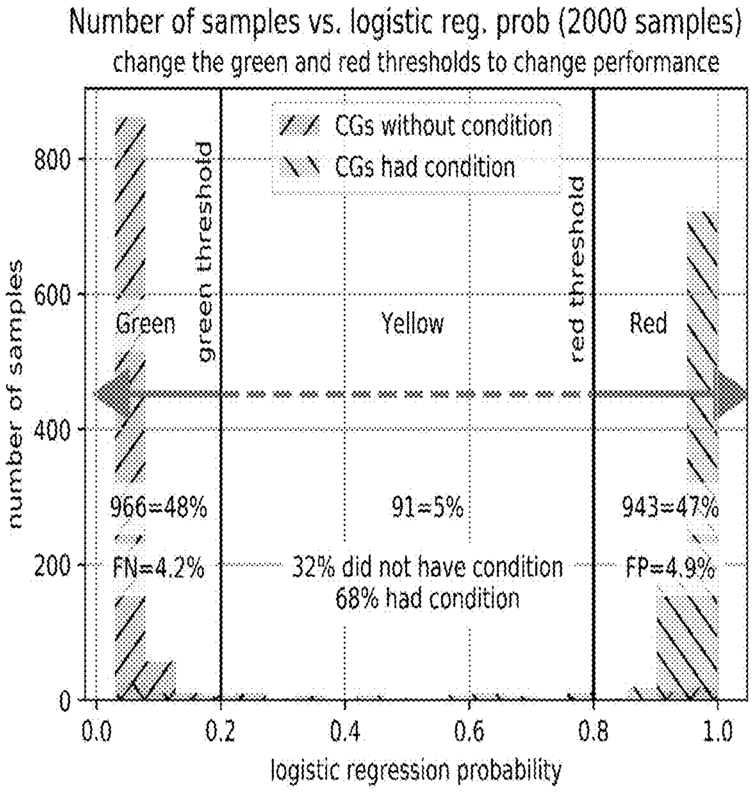

In one embodiment, the process computes the number of true negatives, false negatives, true positives and false positives and display them graphically on a histogram of number of samples vs. logistic regression probability as shown in FIG. 29. In one embodiment, the system designer trade off true and false negatives as well as true and false positives by changing the thresholds. Manual adjustment of thresholds is advantageous because it gives the system designer detailed control of performance. In the example in FIG. 29B, 48% of the caregivers (966 out of 2000 in the validation set) were "Green" and they in fact did not have condition c. 4.2% were Green and did have condition c. 5% of caregivers were "Yellow," indicating they were at increased risk for condition c and 68% of them actually did develop condition c. 47% of caregivers were "Red" and 95.1% of them developed condition c. The inspection of this graphical depiction verifies that the $G_{thresh}$ and $R_{thresh}$ values we chose do in fact provide a reasonable separation of the validation data into Green, Yellow, and Red groups. Henceforth, we apply the GYR classifier to the output of the neural network classifier to obtain Green, Yellow, and Red signals for the user interfaces.

The decision evaluation routine in FIG. 18 applies the GYR classifier to the output of the neural network classifier and displays the result in a user interface that lets the user (typically a home care agency manager) to determine whether to issue an alert, who should receive it, and how it should be transmitted. For example, if a caregiver has recently exhibited significantly reduced job performance, remedial training could be offered.

Figure 30:
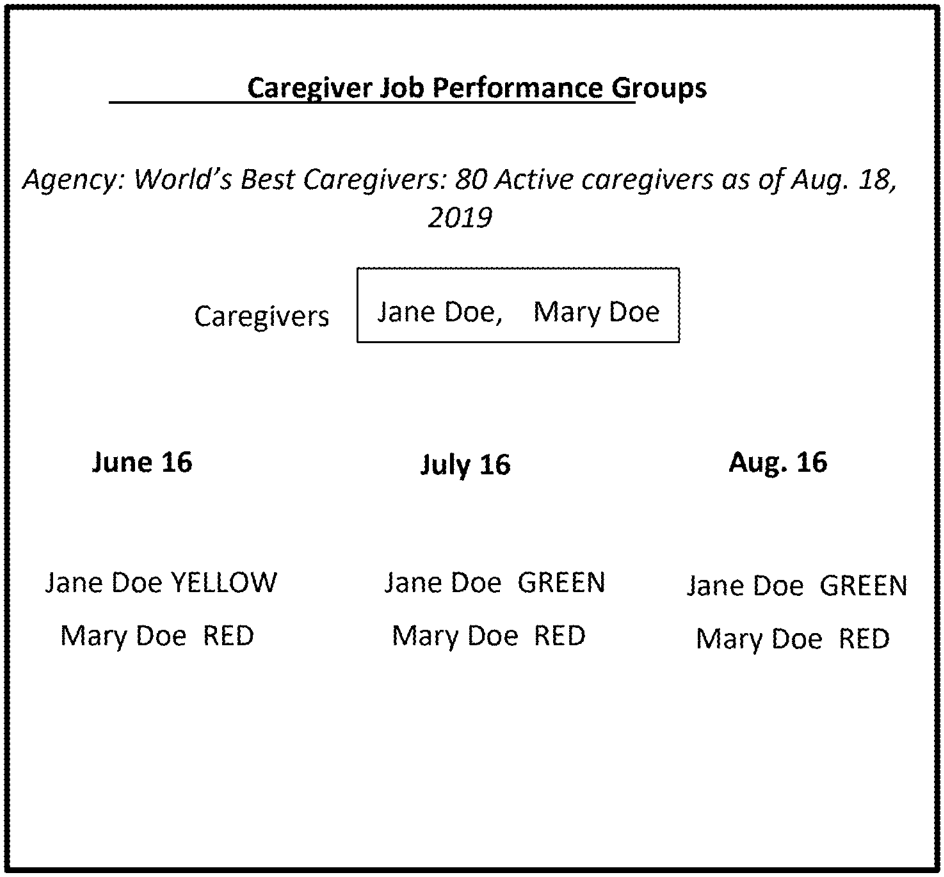
FIG. 30 illustrates an agency or manager user interface in accordance with an embodiment.

FIG. 30 shows an example of a user interface that is used in the decision evaluation function of FIG. 19. The agency owner or manager selects Jane Doe and Mary Doe because he wants to know how their job performance has been over the past three months since it's time for their annual performance evaluations. We see that Jane Doe was in the Yellow zone (warning level) three months ago but she's exhibited consistently improved performance over the past three months. This indicates that Jane is a conscientious employee who wants to improve and who probably should be rewarded at her next evaluation. On the other hand, Mary Doe has a problem. She has consistently exhibited poor job performance over the past three months. This should certainly be taken into account during her annual review.

Figure 31:
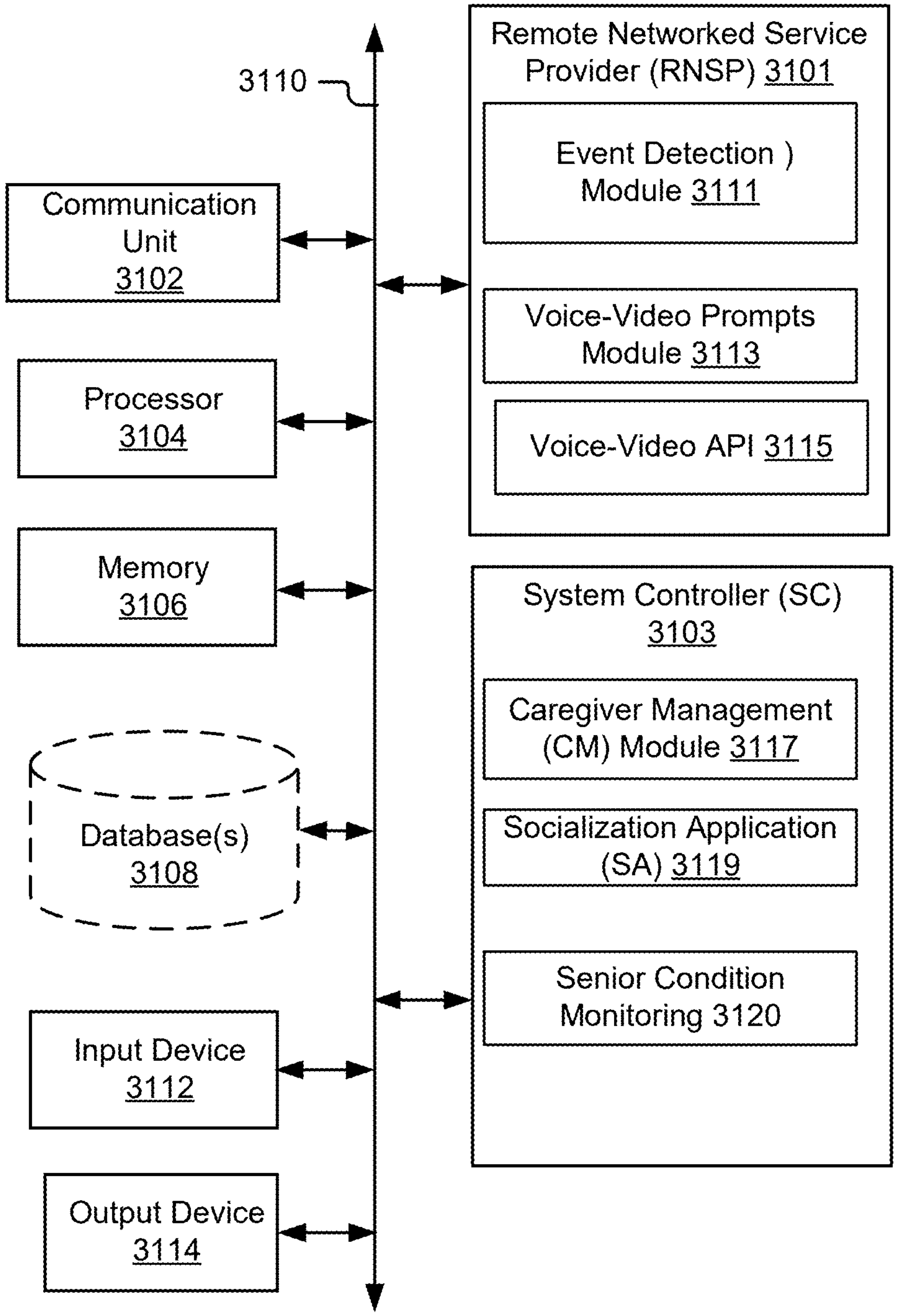
FIG. 31 illustrates a server architecture in accordance with an embodiment.

FIG. 31 illustrates an example of a server architecture for implementation of an embodiment of this disclosure. A communication interface 3110 is provided. The server architecture may include a network communication unit 3102, a processor 3104, a memory 3106, a database 3108, an input device 3112, and an output device 3114. The RNSP service provider 3101 may be supported by an event detection module 3111, a voice-video prompts module 3113, and a voice-video API 3115. The system controller 3103 may include modules to support any of the examples described in this disclosure, such as a caregiver management module 3117, a socialization application 3119, and a senior condition monitoring module 3120.

Example IOT Integration with Google Home™

Embodiments of the disclosure can be implemented using different types of IOT devices at home. An example is now provided of providing in-home care augmented by IOT devices with reference to products and services offered by Google™, such as Google Home™ and Google Assistant™, which are example of voice assistants. Additionally, the Google Nest™ division is focused around products for the home such as thermostats, alarm systems, cameras, etc.

In one embodiment, clock-in/clock-out is implemented using voice activated devices powered by Google Assistant™.

In designing a system using Google Assistant, one issue lies in preserving the privacy of health information under HIPAA. Google Assistant is not HIPAA eligible. As a result, it is preferable to not send personal health information (PHI) information such as client name, address, medication details etc. to the Google Assistant, as the Google Assistant is (as of 2018) not HIPAA eligible.

Moreover, this example points out an important implementation detail, namely HIPAA requirements can, in some implementation, be an important design consideration in terms of the types of information flows.

In one embodiment, the SC 110 is implemented such that that PHI can be sent to the SC 110 in a manner that complies with HIPAA considerations. For example, in some embodiments, PHI cleanup logic ensures that data sent to the SC is HIPAA compliant. Provisions may be included in the design to not accept comments that include PHI data. Other PHI protection schemes may also be included.

In one embodiment, the system architecture separates a device specific thin-layer to support different devices like Alexa and Siri in addition to Google Assistant, from the business logic layer that is device agnostic and handles the meat of business logic.

In one embodiment, a single lambda endpoint is registered with Google Dialogflow and using command pattern, route to appropriate internal endpoint based on Fulfilment type.

There are some practical implementation considerations in regards to linking patient accounts of the SC 110 with Google Home™ accounts. For example, some seniors with early stage Alzheimer's have diminished cognitive ability that may make it difficult for them to set up and link accounts on their own. In one embodiment, support is provided for client login and/or linking of accounts. For example, some seniors may need assistance to setup and link a Google account to an IOT system account. As an example, an Agency administrator may provide assistance during a visit to a senior's home. Alternately, family members may help create accounts. In one embodiment, support is provided for the sign-in process and token exchange process for secure access to the SC 110. Support may also be provided to address the possibility that there are multiple voice profiles in a Google Home™ implementation.

As one example, consider a basic clock-in process. This may be implemented using a multi-step "Google Conversation" with an IOT system called "ClearCare."

Consider the following example of a Google Conversation:

User "Hey Google, let me talk to ClearCare."

Developer Note: This first request describes how users invoke the app by its name, in this case, ClearCare. This triggers an intent to invoke the app.

Google Assistant "Sure, here's ClearCare."

ClearCare "Welcome to ClearCare! How can I help you?"

Developer Note: This is the action's welcome default response and handles the previous intent that was triggered.

User "Clock In/I like to Clock In/Please Clock me in"

Developer Note: The user says a "command", which is parsed by Dialogflow. A corresponding intent is triggered and calls your fulfillment.

ClearCare "Are you Caregiver X?"

User "Yes"

ClearCare "Would you like to hear your tasks for this shift?"

User "Yes"

ClearCare "You have N tasks. These include:

Task 1: <If applicable, at Starttime T1><description of the task>

Task 2: <If applicable, at Starttime T2><description of the task>

. . . ."

ClearCare "Thank you! You have successfully clocked in."

Developer Note: The fulfillment detects that the user completed clock in and ends the conversation.

Now an exemplary clock-out process is described that is also implemented as a multi-step "Google Conversation" whose happy path will look like this:

User "Hey Google, let me talk to ClearCare."

Developer Note: This first request describes how users invoke the app by its name, in this case, ClearCare. This triggers an intent to invoke the app.

Google Assistant "Sure, here's ClearCare."

ClearCare "Welcome to ClearCare! How can I help you?"

Developer Note: This is the action's welcome default response and handles the previous intent that was triggered.

User "Clock Out/I like to Clock Out/Please Clock me out"

Developer Note: The user says a "command", which is parsed by Dialogflow. A corresponding intent is triggered and calls your fulfillment.

ClearCare "Are you Caregiver X"

User "Yes"

ClearCare "Please confirm status of the tasks for this shift."

You had N tasks:

Task 1: <If applicable, at Starttime T1><description of the task>. Is this task successfully completed?

Developer Note: Only list standard tasks for now, as we need PHI cleanup logic for custom tasks. Also, not taking comments as they make include PHI data. But can easily be added later.

User "Yes"

ClearCare "Task 2: <If applicable, at Starttime T2><description of the task>. Is this task successfully completed?"

. . . .

User "Yes"

ClearCare "Your last Task: <If applicable, at Starttime T2><description of the task>. Is this task successfully completed?"

User "Yes"

ClearCare "Thank you! You have successfully clocked out."

Developer Note: The fulfillment detects that the user completed clock in and ends the conversation.

The clock-in, clock-out examples illustrate some general principles that may be expanded to include other types of conversations, such as those between a client (senior) and ClearCare, a FM and ClearCare, etc.

Note that in a product implementation, training (or a training manual) may be provided for admins/caregivers/clients/family members so that they are aware of available commands

Additional Embodiments

Additional examples and embodiments of a system and method are described below that may be implemented utilizing the system described above.

A. Data Product

In one embodiment, the data captured by the system for a senior is provided as a data product to doctor, medical professions, etc. Doctors and other medical professionals see the senior rarely and only for a few minutes at a time. Caregivers (CGs) might see the senior daily for hours at a time. They could provide information about the patient's condition (including behavioral information) that has not previously been available.

In one embodiment, the combination of a CG and IOT devices gives a constant sampling (time series) of the senior's condition over time that allows the SC 110 to track how the senior's condition changes and transitions between disease states. Such fine-grained data has not previously been available on a wide scale. For example, it permits tracking cognitive state, biomarker (e.g. blood sugar), walking ability, and sleep quality on a frequent basis, in some cases on a daily or even hourly basis.

1. Extract features specific to customer needs—EMR companies need vital signs daily, when falls occur, and their severity. They don't need the raw video feeds from the senior's room. In one embodiment, features are extracted from the raw data for use by third parties, such as EMR companies.

2. Health graph tracking—In one embodiment, based on data from 5 million patients, identify 250 or 500 typical health graphs and identify where each senior is on any particular graph. This permits prediction of their near-term transitions to other states in the graphs. In one embodiment, interventions are generated that have been shown to steer seniors to less expensive (for the insurance company) paths in the graph.

3. Advertising directed to seniors or family members based on changing condition of seniors—In one embodiment, based on the expected health state of the senior, as determined by matching to conditions of other seniors in the system database, predict when seniors will need a health care product or service (e.g., a new walker) and use that information to generate focused advertisement to seniors or their family members.

4. Recommendations to health care providers based on predicted condition of senior—In one embodiment, the SC observes with IOT that the senior's condition entered a precipitous decline (e.g., a decline in the last 30 days.) In response, the SC 110 recommends that CGs should be provided 16 hours per day instead of 4 hours day because our data shows that this substantially reduces readmission.

B. Medication Adherence—Pillbox Monitoring, Etc.

1. Voice assistant (VA) prompting and verification—In one embodiment, the SC 110provides a medication schedule to the VA. It prompts the senior or the CG to take medications at the prescribed times. "Mary, it's time to take a small triangular blue pill and a large round white pill" might be an example. Mary could respond "OK, I did it." This may be combined with CG follow-up. Alternatively, this could be implemented using the senior's phone in place of VA.

2. Voice assistant pill box filling—In one embodiment, the CC SC walks the senior or the CG through the process of filling the pill box for the next day or week. For a senior who takes ten different medications six times a day, this can be quite confusing. In one embodiment, the IOT system is provided with an input from an EMR and pharmacy to ensure the correct procedures are used. Alternatively, the senior's phone or the CG phone could be used instead of the VA.

3. Medication administration verification service—In one embodiment an interface is provided on the CG's phone, synchronized to the medication schedule of the senior, that requires the CG to verify that medications have been taken by the senior at the specified times.

4. Adherence prediction service—In one embodiment, based on past histories of similar seniors in the system database (assuming IOT data and perhaps EMR info), and given info about the medication schedules of the senior, predict which seniors are more likely to have difficulty adhering to their schedules and recommend higher levels of CG attention for these seniors.

5. Manually filled pillboxes networked to networked pillboxes filled by seniors or CGs. In one embodiment, the pillbox reports the weight in each bin over time and when the bins are opened or closed.

6. Networked pillboxes (manually filled) with networked dispensation—In one embodiment, the pillbox pops open bins on command and tells the CG to administer the medication.

7. Networked pillboxes with special insertion device. In one embodiment, the bar code reader that allows the CG or senior to jam specially designed pill containers onto the device, puncturing the container and filling the pillbox with known medications. This eliminates the need to open pill bottles and sort miniscule pills that are hard to see and identify. The device reduces workload and responsibility for the CG and increases adherence.

8. Networked pillbox with video and weight—based identification of medications. In one embodiment, seniors or CGs empty their pill bottles into a hopper on the device and it automatically identifies each pill based on its shape, color, and weight (see Physicians' Desk Reference for color photos of pills). The pillbox receives instructions from CC that dispense the medications according to a schedule.

C. Curated Social Network—Several different versions of a curated social network are possible, depending on the amount of technology that's employed.

1. Initiated social connections—In one embodiment, the SC 110 identifies nearby seniors who are patients in the IOT system and would like to connect with other seniors. A prescribed set of interactions are defined, like meeting at the park for 30 minutes, walking in the mall for an hour, playing cards three times a week, etc. This would initiate social interactions that could build (or not) over time.

The success of this technique is of course personality-driven. Some seniors would be resistant, others would welcome it. Some seniors could meet different seniors in the park every three days and never progress beyond that. Others would find new friends and develop deep relationships.

An advantage that IOT system has is the caregivers who could mediate the interactions. Seniors who are reluctant to participate could be encouraged by their caregivers to get involved. For example, at 2 PM on Friday the caregiver would encourage the senior to get ready for their outing at 3 PM.

Another version of this would connect seniors with folks who sign up with the IOT system, not as caregivers but as friends. Friends would be folks who want to talk with seniors about their problems, etc., but not be involved with their medical care. Sort of like the Big Brothers Big Sisters http://www.bbbs.org/model but for seniors. In one embodiment, The IOT system provider would do criminal background checks on friends as part of the vetting process and caregivers would report on the senior's opinion of the friends.

Alternatively, Friends would be paid hourly for their time but would have the opportunity to decline payment or donate their salary to charity.

2. Voice assistant version—In one embodiment, the previously described initiated social connections service is augmented or replaced with a similar approach that uses a voice assistant. A similar vetting process would be needed. Friends could be other seniors who are patients in the IOT system or they could be folks who sign up to be friends rather than caregivers. Interactions on the VA would be monitored by transcription of their content to guard against abusive behavior.

3. Mechanical Turk conversational connections service—In one embodiment, a crowdsourcing Internet marketplace (e.g., Amazon's Mechanical Turk) is used to provide a conversational connections service. In one embodiment, seniors log on to their laptops and connect with their "friends" who they chat with about their problems and concerns. In one implementation, friends are contractors who are paid by the hour. This allows the friends to work from anywhere. This could be one to one in which a senior connects with friends like a "normal" chat. Or, it could be one to many in which friends describe their personal lives, like a soap opera, and use this as fodder to solicit input and make connections with seniors. That is, friends could intersperse comments directed to individual seniors in their one-to-many broadcasts (see Periscope app) and could follow that up with one-to-one conversations. This personalizes the experience that many seniors have with their soap operas on TV and introduces conversations with the actors. It also adapts the system to different personalities of seniors and friends.

This app has great potential for reducing loneliness but in some implementation could employ a sliding scale of charging or other means to limit the amount of time seniors spend using it. Think about the lonely seniors who can go on for hours at a time about their kids, their experiences growing up, their time in the Army, etc. Those folks need someone to listen to them. This would tie up friends for a long time. But it would be quite valuable time from the point of view of reducing loneliness. Other seniors are less talkative and would rather listen and react (or not) to the stories of others. That is, the system would need to adapt to a range of personality types.

In one embodiment, friends are provided training to identify the problems and issues experienced by seniors with certain medical conditions. In one embodiment, they would need a criminal records check and monitoring to ensure they are not exploiting the seniors (e.g., tricking them into sending them their life savings). In one embodiment, the IOT augmented system supplies the friends with a thumbnail background sketch of the seniors they are talking with and would be encouraged to reach out and make increasing levels of connection, not being too pushy.

The IOT augmented ssytem would have a unique ability to use IOT and caregivers to monitor the responses of the seniors to the interactions with their friends, perhaps by passively monitoring the voice assistant or actively prompting them for their reactions.

Caregivers could log the opinions of seniors about their friends; help seniors use the system, and direct seniors to certain categories of friends. Caregivers could also force feed the system to seniors. For example, make them use it six times with three different friends before giving up on it.

4. Virtual Reality social network—In one embodiment, a virtual reality system is trained with data from a spouse, before they die, so the senior can have conversations with the dead spouse.

In one embodiment, the system records training data from spouses for the VR system, well before they pass away. This could be done on an ongoing basis. The same thing could be done with other family members. For example, the spouse would sit down in front of an app on the day their son was born and describe his/her observations, reactions, and emotions on that day. That recording could be replayed 40 years later after the spouse has passed away, but it could also be used to train a VR bot that could answer questions about his deep feelings for his wife and children.

In one embodiment, caregivers help administer the service and monitor reactions of the senior. For example, after an argument with another senior during lunch in the assisted living facility, the CG could say, "let's ask Don (the dead spouse) what he'd say about it." The CG would turn on the VR system, adjust the hardware as needed, and walk the senior through the interaction. Don's image, synthesized from the previous recordings, would appear in the VR display and his bot would counsel Margaret the senior to be patient and say "remember back in 1957 when we were at Yosemite and you had an argument with Pam at lunch, we discussed it later and you agreed that the best thing to do was to apologize to Pam and listen to her problems. You two became great friends after that."

The recording and annotation of training data is key to the success of this approach. The advantage that the system has is the window into the experiences of seniors that can predict the future needs of today's baby boomers. Any VR system would need training data about the situations that seniors will encounter, rather than random general-purpose information. For example, seniors with advanced diabetes have restricted diets that need to be carefully adhered to. When the IOT system detects that the senior is about to eat a candy bar, the dead spouse's bot could admonish the senior in the way she was accustomed to. For example, this might include an argument such as "Margaret I told you to stop eating candy" and she might respond "forget it Don, I'm gonna eat this candy anyway and if you don't stop bothering me I'm gonna go get more." He could say "No you're not!" . . . . For a senior who deeply misses their spouse, this interaction could be quite comforting.

In one embodiment, the system identifies a set of the most common situations encountered by seniors as well as the guidance that might be needed in those circumstances. For example, the reassurance that might be needed when taking medications with certain side effects, the help needed when one is embarrassed about a personal problem, or advice about medical problems. The senior might say "Don, I'm feeling dizzy and confused every day" and the bot could respond "That's OK, don't worry about it, that's normal for someone who has Parkinson's disease. I will be here watching over you."

5. Physician-prescribed loneliness treatment—In one embodiment, if a physician detects that loneliness is a problem, he or she prescribes a selection of loneliness treatments, such as one voice assistant call per day and three-initiated social interactions per week for three months.

D. Individualized directed care based on personality and condition—In one embodiment, 24×7 monitoring of patients, augmented with caregiver observations and interventions, provides unique methods of detecting and predicting changes in emotional and medical conditions.

1. Personality/emotional state monitoring service. In one embodiment, the emotional state of seniors is assessed over time. Based on the personality of the patient, their medical conditions, their medications, the observations of caregivers, and the histories of other seniors with similar characteristics in the system, the system assesses the current emotional state of the senior. Part of this is an app that asks questions of the senior directly or through the CG. The application starts the day with voice conversations and prompts like "did you sleep well," "how do you feel today."

A senior's emotional state can also change dynamically throughout the day, depending on the patient's condition. Someone with dementia can be happy and rational one minute and weeping the next. In one implementation, the daily graph of emotional state is a powerful diagnostic and predictive tool that the system obtains automatically with IOT data, refined with input from caregivers.

The rate of emotional state change over time is also a side effect of specific medication and their dosage. This service can be used as part of fine tuning a senior's medications.

2. Personality/emotional state prediction service In one embodiment, based on the senior's current emotional state, including the IOT data and observations of caregivers, as described above, as well as the history of other seniors in the system database, the SC 110 predicts how the senior's emotional state, relative to their personality, might change. If the onset of depression is predicted, an appropriate intervention is prescribed such as increasing the amount of caregiver time for that patient.

3. Change in Condition detection service—In one embodiment, the SC 110 measures IOT data and responses to voice prompts, including the speed of responses, to detect a change in medical condition. This is powered by annotated training data derived from system's treatment of thousands of patients with similar conditions. This allows the SC 110 to alert the medical care provider that the senior is becoming increasingly infirm. A metric indicative of an infirmity risk can be determined, along with a triggering condition. For example, the speed of the senior's movement patterns and degree to which they move each day may be tracked, a decline in speed (or total daily movement) may be calculated, an alert generated when a triggering condition is reached. For example, the medical care provider could be alerted when the amount of time to get from their chair in front of the TV to the bathroom has steadily increased by 30% over the past ten days.

4. Change in Condition prediction service—In one embodiment, the SC 110 monitors IOT data and responses to voice prompts, including the speed of responses, detects a change in condition. This is powered by annotated training data derived from system's treatment of thousands of patients with similar conditions. This monitoring allows the system to predict a change in condition before it occurs and direct increased care such as a new walker or a motorized wheelchair because there is a 90% chance the senior will fall and break their hip in the next 60 days.

E. Geographically—based Caregiver Assignment (traveling salesman problem)—In one embodiment, one CG services N patients that are nearby one another. N CGs to M patients is another model.

1. Dynamic scheduling of one Caregiver—In one embodiment, individual caregivers are scheduled so that their seniors are within an N-mile radius of one another. This improves efficiency because the CG spends more of their time every day working with patients rather than driving from one patient to another. In one implementation, the system uses IOT data to dynamically reschedule caregivers during the day. For example, if a senior has failed to take their medications and not responded to other prompts, that senior's caregiver is sent an alert on their phone instructing them to go to that senior's home immediately and administer that medication. This is feasible because the caregiver is nearby and the transportation time is minimized. The system can prioritize the response so that the caregiver's current task is interrupted if the event needs an immediate response (e.g., senior has fallen down). Otherwise, the response could be performed after the caregiver is finished with the senior they're currently working with.

2. Dynamic scheduling of more than one Caregiver—In this model, more than one caregiver is familiar and qualified to work with each patient within an N-mile radius of one another. The schedules of those caregivers are dynamically shuffled throughout the day so that the needs of their seniors can be met. There can be multiple sets of overlapping caregivers. That is, for a given caregiver, each of their M patients may have a different set of C caregivers that could fill-in when needed. A parameter in this model is the preference of the senior for each caregiver. They may prefer one caregiver over another but will accept either of them. This is known to the scheduling algorithm. One result of this technique is a confirmation that the tasks that triggered the reshuffling of schedules have been successfully completed.

F. Payer—Related Services—

1. Future Prediction Service—In one embodiment, given the senior's DNA report from 23andMe, their EMR data, and the functional, social, and behavioral data from the time when the senior was in the system, match that to the system database of the past experiences of other seniors and predict the future course for this patient as well as how they can make changes that would improve their outlook. For example, a certain senior with a heart condition and type two diabetes at a given level has a 90% chance of having their right leg amputated in one year if they continue with their current lifestyle. Going to a vegetarian diet and walking 5000 steps per day will reduce that to 15%.

2. A/B Testing Service—In one embodiment, the system offers dynamic A/B testing of care strategies to clinical decision support providers (CDSPs). For example, a CDSP might wish to test whether a given exercise regime, e.g., walking ten minutes three times per day, has a beneficial effect on seniors with COPD who use a walker. The system would select the seniors who would be in the group that received the treatment and the group that didn't. Caregivers would ensure that the exercise routine was performed correctly and would record the results.

G. Food Farmacy—In one embodiment, support is provided for the design, delivery, and preparation meals customized for the care plan of the patient. Geisinger has results in Pennsylvania that show this technique can dramatically reduce health care costs for patients with type 2 diabetes.

1. Custom Meal Design Service (CMDS)—In one embodiment, CMDSs like Blue Apron, prepare tasty meals customized for each patient. Some people are picky about what they eat. They might eat one of ten different dishes and nothing else. Other people are open to new ideas and appreciate the high-quality meals arranged by Blue Apron, an Internet service that never uses the same recipe. Nevertheless, it's essential for the health of the patient that they eat the foods prescribed by their doctor. It's the job of the CMDS to maximize the chance that this will occur, especially for a population of cranky seniors who might be resistant to making changes.

The CMDS uses information from the system database about what's eaten by seniors with similar backgrounds and input from the caregiver, who has a specially designed phone app with the ability to input specialized preferences from the senior, to design a menu that will be acceptable to the senior. The meals are prepared and delivered to a staging area designated by the agency. Ingredients may need to be flown in or express shipped.

The system database records which meals were finished by each senior. That data is fed back into the meal design algorithm so that in the future a larger percentage of the meals are actually consumed.

2. Meal Delivery and Preparation Service—Caregivers or meal preparation technicians prepare meals for the senior, as determined by their care plan. The meals can be designed with ingredients from the local supermarket or they could be prepared from CMDS meals. However, they must be consistent with the senior's care plan.

There will be a problem if only caregivers are allowed to prepare meals because every senior will need their dinner at about the same time. It's easy to see that scheduling will be challenging. Therefore, we introduce a new category of caregiver, the meal preparation technician (MPT), who cooks the food that is delivered, by whatever means.

MPTs are scheduled based on geographic constraints so their clients are all within an N mile radius. In addition, the system chooses MPTs whose personality matches that of the senior. Uber could deliver the MPTs and/or the meals to the senior's home.

3. Nationwide Platform for Customized Meal Design, Delivery, and Preparation—The Geisinger experiment shows that this technique can be extremely valuable to payers. Health care costs can be dramatically reduced. The issue is how to scale the approach [ref. Blue Apron]. However, the system has the means to do that with their army of agencies and caregivers and their ability to add new categories of workers to their system (meal preparation technicians) who can participate in the process.

4. Voice prompted forms with physical action and verification—In one embodiment, Web forms include fields where the description of the field is a question that is answered by caregivers on the phone. An additional part of this embodiment is that, in the case of one embodiment, there are caregivers on the other end of the form who can perform and verify that the specified action was performed. For example, the question might be, "enter your blood pressure," and the caregiver takes the blood pressure with a BP cuff and reads the result back over the phone "120 over 90."

5. Voice prompted forms (horizontal version)—In one embodiment, in its horizontal version, a web form includes a widget that reads a web form and creates a voice form. Questions on the form are spoken using text to speech, with proper intonation, and the responses are transcribed with speech to text technology.

H. Voice Assistance for Caregivers and Recruiting—

1. Voice Assistant Application Specialized for Home Care Patient—In one embodiment, a VA, such as Alexa, is connected to the system database that includes information from the EMR about the patient and the conditions they are being treated for. Patients take Alexa home with them. The app reminds patients to take their meds on schedule, prepare appropriate meals, and in general adhere to their care plan.

2. Detection and Recruiting of Caregivers—In one embodiment the system uses a voice assistant or other IOT inputs to detect that someone is providing care to a senior. The mailing address where the voice assistant or IOT device is installed will be known from the voice assistant application, since users often tell it where it is, or can be inferred from the VA's IP address. Since in one embodiment the system knows the mailing addresses of all its agencies' patients, it can tell whether the caregiver works for an agency using the system.

If the caregiver works for an agency not associated with the system and (perhaps) the system detects that they are providing high quality care and if they've stayed on the job more than three months, showing they are not an early quitter, the system can recruit them. This can include prompts through the voice assistant when the patient is out of the room.

3. Passive Detection of Attributes of Long Term Caregivers—In one embodiment the system monitors the interactions between caregivers and seniors and after the caregiver has been there a while and they are executing a high-quality care plan, detect attributes exhibited by that caregiver that could be helpful in recruiting and retention, such as their ability to relate to the senior, their attitude over time, their tone of voice, etc.

4. Active Detection of Attributes of Long Term Caregivers—In one embodiment, after a caregiver has been on the job for a while and they are known to provide high quality care, the system occasionally asks questions about their background that could be helpful to the statistical model for evaluating caregiver candidates. For example, if statistics are needed about country of origin and time lived in the U.S., the system could ask that of all the caregivers both inside and outside the system who happen to be using the voice assistant application.

I. Convert Unpaid Non-Directed Care to Unpaid Directed Care

1. Voice Assistant Detection of Undirected Care—In one embodiment, the App is given away for free, perhaps activated by default by Amazon and Google, it's constantly monitoring everything said in the room, and interrupts when it detects care is being provided to a senior. It suggests best practice for the condition being treated. Amazon knows the purchase history of the household and whether it contains senior citizens. Google knows the web browsing history of the IP addresses associated with the household and can predict whether it contains seniors. That is, the app knows the a-priori probability that the household would contain seniors who might be receiving undirected care.

2. Insurance Company—Directed Detection of Undirected Care—In one embodiment, the senior's insurance company can require the patient to install and use a VA (e.g., Alexa) at home, either by threat of withdrawing coverage or by incentivizing with lower insurance costs. The presenting use case can be prescription reminders but the underlying benefit can be detection of undirected care.

3. Voice Assistant Conversion to Directed Care—In one embodiment, once non-directed care is detected, by whatever means, the voice assistant can help convert the care of that patient to best practice, consistently over time. This can be entirely through the use of the voice assistant interfaced to the system database. The system can build a profile for the patient over time. It can solicit permission to retrieve the health records for the patient from Kaiser and use that information to provide specialized advice.

4. Conversion of Directed Care by Family Members (uncompensated) to Telemedicine—In one embodiment, as caregivers become accustomed to using the voice assistant as part of providing care to their family member, they are introduced to the use of Telemedicine. When they ask questions that cannot be answered by a bot, they are prompted "Please standby for Nurse Nancy." Nancy immediately comes on the line and starts answering their questions. This care could be free to the patient and paid for by the insurance company since it would help reduce readmissions.

5. Conversion of Directed Care by Family Members (uncompensated) to Agency associated with system—As the free system is helping family members provide care to their senior, at some point there is something it can't do, even with telemedicine. For example, assistance getting in and out of the shower. At that point, the VA (e.g., Alexa) can ask "would you like me to send someone over to help?" The family member could verify that and pay for the care with their Prime account. The system would refer the contact to an agency that would fulfill the request.

6. Detection and Verification of Caregiver Behavior—In one embodiment, the system detects and verifies CG behavior. For example, caregivers are not supposed to be browsing Facebook at work. We detect that behavior with an app on the phone or software on the free W-Fi access point in the senior's living space. We should list desirable and undesirable behaviors by caregivers and determine methods of detecting them.

7. Detection and Verification of Senior Behavior—In one embodiment, the system detects and verifies senior behavior. For example, suppose the care plan specifies that the senior is supposed to walk around for ten minutes three times a day. A step counter on the phone can determine this. The system may list desirable and undesirable behaviors by seniors and determine methods of detecting them. Prohibited behaviors such as smoking could also be detected.

J. Workflow Builder—In one embodiment, a workflow builder includes predictive analytics, clinical decision support, plus activating a human and leveraging IOT information.

1. Dynamically change workflows based on IOT data, predictive analytics, clinical decision support and input from a caregiver. This inserts new steps into a customized workflow for a given patient so that everyone else on their care team knows that they are now walking for ten minutes every day at 10 AM, noon, and 4 PM. The success of that workflow element is from then on recorded in the system.

2. Automatic insertion of new steps in a patient's workflow. This occurs when the patient is prescribed a new medication that must be taken with food twice per day, for example. The caregivers for that patient will automatically be informed about those new requirements.

K. Data-Based Engine for Improving Patient Outcomes

1. Passive Identification of Cost of Care. In one embodiment, based on analysis of IOT data, clinical decision support information over time, and patient care history in the system database, the system identifies the cost of care per state of each major disease (diabetes, COPD, CHF, ESRD) for seniors who receive the range of care experienced across the system network. This is broken down by the care received by those patients, the regions they live in, their health care providers, etc. This system could be applied to a specific payer's population of patients.

2. Recommendation Engine for Improving Care. In one embodiment, based on the results of passive identification of cost of care, the system also identifies steps that have been executed by caregivers in the system that have been shown to improve outcomes and reduce cost. For example, in patients with advanced kidney disease, this could be ensuring they adhere to their dialysis appointment schedule. The system identifies those critical steps and couples them with interventions, such as the dispatch of Uber plus a caregiver, that make sure those steps are implemented.

3. Insurance Companies Send Patients, Authorizations and Interventions. In one embodiment, the system sends a patient to an agency in their network that executes the intervention. A recommendation is generated based on a statistical analysis that identifies the agency and caregivers, with available time in their schedules (we have dynamically updated desired utilization) who have a good record in executing the intervention. Also, the IOT data of those past patients on which the recommendation is based is analyzed as part of formulating the recommendation. Agencies are encouraged to use caregivers recommended system. Schedulers at the agencies are provided means to enter reasons why the systems recommendation should be followed or reasons why they chose not to follow the recommendation. Those inputs are used in tuning up the statistical model.

Other implementations of one or more of these aspects include corresponding methods, apparatus, and computer programs, configured to perform the actions of the system and methods encoded on computer storage devices.

Other Alternate Embodiments And Implementations

In the above description, for purposes of explanation, numerous specific details are set forth in order to provide a thorough understanding of the specification. It will be apparent, however, to one skilled in the art that the invention can be practiced without these specific details. In other instances, structures and devices are shown in block diagram form in order to avoid obscuring the description. For example, the present invention is described in one implementation below primarily with reference to user interfaces and particular hardware. However, the present invention applies to any type of computing system that can receive data and commands, and present information as part of a mobile device.

Reference in the specification to "one implementation" or "an implementation" means that a particular feature, structure, or characteristic described in connection with the implementation is included in at least one implementation of the description. The appearances of the phrase "in one implementation" in various places in the specification are not necessarily all referring to the same implementation.

Some portions of the detailed descriptions described above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared and otherwise manipulated. It has proven convenient at times, principally for reasons of common usage, to refer to these signals as bits, values, elements, symbols, characters, terms, numbers or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present specification also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD ROMs, and magnetic disks, read-only memories (ROMs), random access memories (RAMs), EPROMS, EEPROMs, magnetic or optical cards, flash memories including USB keys with non-volatile memory or any type of media suitable for storing electronic instructions, each coupled to a computer system bus.

The specification can take the form of an entirely hardware implementation, an entirely software implementation or an implementation containing both hardware and software elements. In one implementation, the specification is implemented in software, which includes but is not limited to firmware, resident software, microcode, etc.

Furthermore, the description can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modems and Ethernet cards are just a few of the currently available types of network adapters.

Finally, the algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the specification is not described with reference to any particular programming language. It will be appreciated that a variety of programming languages may be used to implement the teachings of the specification as described herein.

The foregoing description of the implementations of the present invention has been presented for the purposes of illustration and description. It is not intended to be exhaustive or to limit the present implementation of invention to the precise form disclosed. Many modifications and variations are possible in light of the above teaching. It is intended that the scope of the present implementation of invention be limited not by this detailed description, but rather by the claims of this application. As will be understood by those familiar with the art, the present implementation of invention may be embodied in other specific forms without departing from the spirit or essential characteristics thereof. Likewise, the particular naming and division of the modules, routines, features, attributes, methodologies and other aspects are not mandatory or significant, and the mechanisms that implement the present implementation of invention or its features may have different names, divisions and/or formats. Furthermore, as will be apparent to one of ordinary skill in the relevant art, the modules, routines, features, attributes, methodologies and other aspects of the present implementation of invention can be implemented as software, hardware, firmware or any combination of the three. Also, wherever a component, an example of which is a module, of the present implementation of invention is implemented as software, the component can be implemented as a standalone program, as part of a larger program, as a plurality of separate programs, as a statically or dynamically linked library, as a kernel loadable module, as a device driver, and/or in every and any other way known now or in the future to those of ordinary skill in the art of computer programming. Additionally, the present implementation of invention is in no way limited to implementation in any specific programming language, or for any specific operating system or environment. Accordingly, the specification of the present implementation of invention is intended to be illustrative, but not limiting, of the scope of the present implementation of invention, which is set forth in the following claims.

What is claimed is:

1. A system for providing in-home care for seniors, comprising:

a machine learning subsystem including a processor configured to:

generate a normalized feature vector from a set of sensor outputs from sensors disposed within a living area of a senior according to a sensor floorplan, including identifying a first relationship between symptoms of dementia and events, wherein the events are measurable physical or mental features associated with at least one of the symptoms of dementia, identifying a second relationship between the events and the set of sensor outputs based at least in part on a location of each sensor and a sensor type of each sensor; and identifying a third relationship of sensor transformations required to transform sensor data into a format indicative of events, wherein the first relationship, the second relationship, and the third relationship is used to generate the normalized feature vector;

input the normalized feature vector to a logistic regression classifier of a machine learning model, wherein the logistic regression classifier is trained to determine thresholds for identifying dementia based on a training data set of a set of seniors; and determine a likelihood that the senior has dementia.

2. The system of claim 1, wherein the machine learning subsystem is further configured to generate an alert in response to determining a risk the senior has dementia.

3. The system of claim 1, further comprising a sensor installation subsystem to determine a number of required sensors, associated sensor types and sensor locations of sensors disposed within a living area of a senior according to a sensor floorplan.

4. The system of claim 1, wherein at least one of the sensors is an Internet of Things (IOT) sensor device.

5. The system of claim 1, wherein the sensor data is selected from:

a voice assistant appliance;

a video assistant appliance;

a smart phone;

a tablet computer;

a smart watch;

a smart appliance;

a personal computer; or a home monitoring system.

6. A computer implemented method for providing in-home care for seniors, comprising:

generating a normalized feature vector from a set of sensor outputs from sensors disposed within a living area of a senior according to a sensor floorplan, including identifying a first relationship between symptoms of dementia and events, wherein the events are measurable physical or mental features associated with at least one of the symptoms of dementia, identifying a second relationship between the events and the set of sensor outputs based at least in part on a location of each sensor and a sensor type of each sensor; and identifying a third relationship of sensor transformations required to transform sensor data into a format indicative of events, wherein the first relationship, the second relationship, and the third relationship is used to generate the normalized feature vector;

inputting the normalized feature vector to a logistic regression classifier of a machine learning model, wherein the logistic regression classifier is trained to determine thresholds for identifying dementia based on a training data set of a set of seniors; and determining a likelihood that the senior has dementia.

7. A computer implemented method for providing in-home care for seniors, comprising:

mapping a set of sensor outputs from sensors disposed within a living area of a senior to events associated with features of symptoms of dementia for the senior to generate an event vector for the senior identifying a first relationship between symptoms of dementia and events, wherein the events are measurable physical or mental features associated with at least one of the symptoms of dementia, identifying a second relationship between the events and the set of sensor outputs based at least in part on a location of each sensor and a sensor type of each sensor; and identifying a third relationship of sensor transformations required to transform sensor data into a format indicative of events;

generating a normalized feature vector from the sensor outputs based on the first relationship, the second relationship, and the third relationship;

classifying the event vector into a likelihood that the senior has dementia using a classifier trained to determine thresholds for identifying dementia based on a training data set of a set of seniors; and generating an output indicative of a risk a senior has dementia.

8. The method of claim 7, wherein the sensors comprise sensors of user devices of the senior and Internet of Things (IOT) devices.

9. A system for providing in-home care for seniors, comprising:

a machine learning subsystem including a processor configured to:

generate a normalized feature vector from a set of sensor outputs from sensors disposed within a living area of a senior according to a sensor floorplan, including identifying a first relationship between symptoms of a medical condition and events, wherein the events are measurable physical or mental features associated with at least one of the symptoms of the medical condition, identifying a second relationship between the events and the set of sensor outputs based at least in part on a location of each sensor and a sensor type of each sensor; and identifying a third relationship of sensor transformations required to transform sensor data into a format indicative of events, wherein the first relationship, the second relationship, and the third relationship is used to generate the normalized feature vector;

input the normalized feature vector to a logistic regression classifier of a machine learning model, wherein the logistic regression classifier is trained to determine thresholds for identifying the medical condition based on a training data set of a set of seniors; and determine a likelihood that the senior has the medical condition.

10. The system of claim 9, wherein the machine learning subsystem is further configured to generate an alert in response to determining a risk the senior has the medical condition.

11. The system of claim 9, further comprising a sensor installation subsystem to determine a number of required sensors, associated sensor types and sensor locations of sensors disposed within a living area of a senior according to a sensor floorplan.

12. The system of claim 9, wherein at least one of the sensors is an Internet of Things (IOT) sensor device.

13. The system of claim 9, wherein the sensor data is selected from:

a voice assistant appliance;

a video assistant appliance;

a smart phone;

a tablet computer;

a smart watch;

a smart appliance;

a personal computer; or a home monitoring system.

14. A computer implemented method for providing in-home care for seniors, comprising:

generating a normalized feature vector from a set of sensor outputs from sensors disposed within a living area of a senior according to a sensor floorplan, including identifying a first relationship between symptoms of a medical condition and events, wherein the events are measurable physical or mental features associated with at least one of the symptoms of the medical condition, identifying a second relationship between the events and the set of sensor outputs based at least in part on a location of each sensor and a sensor type of each sensor; and identifying a third relationship of sensor transformations required to transform sensor data into a format indicative of events, wherein the first relationship, the second relationship, and the third relationship is used to generate the normalized feature vector;

inputting the normalized feature vector to a logistic regression classifier of a machine learning model, wherein the logistic regression classifier is trained to determine thresholds for identifying the medical condition based on a training data set of a set of seniors; and determining a likelihood that the senior has the medical condition.

15. A computer implemented method for providing in-home care for seniors, comprising:

mapping a set of sensor outputs from sensors disposed within a living area of a senior to events associated with features of symptoms of a medical condition for the senior to generate an event vector for the senior identifying a first relationship between symptoms of the medical condition and events, wherein the events are measurable physical or mental features associated with at least one of the symptoms of the medical condition, identifying a second relationship between the events and the set of sensor outputs based at least in part on a location of each sensor and a sensor type of each sensor; and identifying a third relationship of sensor transformations required to transform sensor data into a format indicative of events;

generating a normalized feature vector from the sensor outputs based on the first relationship, the second relationship, and the third relationship;

classifying the event vector into a likelihood that the senior has the medical condition using a classifier trained to determine thresholds for identifying the medical condition based on a training data set of a set of seniors; and generating an output indicative of a risk a senior has the medical condition.

16. The method of claim 15, wherein the sensors comprise sensors of user devices of the senior and Internet of Things (IOT) devices.

17. A system for providing in-home care for seniors, comprising:

a machine learning subsystem including a processor configured to:

generate a normalized feature vector from a set of sensor outputs from sensors disposed within a living area of a senior according to a sensor floorplan, including identifying a first relationship between symptoms of a psychological condition and events, wherein the events are measurable physical or mental features associated with at least one of the symptoms of the psychological condition, identifying a second relationship between the events and the set of sensor outputs based at least in part on a location of each sensor and a sensor type of each sensor; and identifying a third relationship of sensor transformations required to transform sensor data into a format indicative of events, wherein the first relationship, the second relationship, and the third relationship is used to generate the normalized feature vector;

input the normalized feature vector to a logistic regression classifier of a machine learning model, wherein the logistic regression classifier is trained to determine thresholds for identifying the psychological condition based on a training data set of a set of seniors; and determine a likelihood that the senior has the psychological condition.

18. The system of claim 17, wherein the machine learning subsystem is further configured to generate an alert in response to determining a risk the senior has the psychological condition.

19. The system of claim 17, further comprising a sensor installation subsystem to determine a number of required sensors, associated sensor types and sensor locations of sensors disposed within a living area of a senior according to a sensor floorplan.

20. The system of claim 17, wherein at least one of the sensors is an Internet of Things (IOT) sensor device.

21. The system of claim 17, wherein the sensor data is selected from:

a voice assistant appliance;

a video assistant appliance;

a smart phone;

a tablet computer;

a smart watch;

a smart appliance;

a personal computer; or a home monitoring system.

22. A computer implemented method for providing in-home care for seniors, comprising:

generating a normalized feature vector from a set of sensor outputs from sensors disposed within a living area of a senior according to a sensor floorplan, including identifying a first relationship between symptoms of a psychological condition and events, wherein the events are measurable physical or mental features associated with at least one of the symptoms of the psychological condition, identifying a second relationship between the events and the set of sensor outputs based at least in part on a location of each sensor and a sensor type of each sensor; and identifying a third relationship of sensor transformations required to transform sensor data into a format indicative of events, wherein the first relationship, the second relationship, and the third relationship is used to generate the normalized feature vector;

inputting the normalized feature vector to a logistic regression classifier of a machine learning model, wherein the logistic regression classifier is trained to determine thresholds for identifying the psychological condition based on a training data set of a set of seniors; and determining a likelihood that the senior has the psychological condition.

23. A computer implemented method for providing in-home care for seniors, comprising:

mapping a set of sensor outputs from sensors disposed within a living area of a senior to events associated with features of symptoms of a psychological condition for the senior to generate an event vector for the senior identifying a first relationship between symptoms of the psychological condition and events, wherein the events are measurable physical or mental features associated with at least one of the symptoms of the psychological condition, identifying a second relationship between the events and the set of sensor outputs based at least in part on a location of each sensor and a sensor type of each sensor; and identifying a third relationship of sensor transformations required to transform sensor data into a format indicative of events;

generating a normalized feature vector from the sensor outputs based on the first relationship, the second relationship, and the third relationship;

classifying the event vector into a likelihood that the senior has the psychological condition using a classifier trained to determine thresholds for identifying the psychological condition based on a training data set of a set of seniors; and generating an output indicative of a risk a senior has the psychological condition.

24. The method of claim 23, wherein the sensors comprise sensors of user devices of the senior and Internet of Things (IOT) devices.

* * * * *